US006713496B2

(12) United States Patent
Allerton et al.

(10) Patent No.: US 6,713,496 B2

(45) Date of Patent: Mar. 30, 2004

(54) 3-(IMIDAZOLYL)-2-ALKOXYPROPANOIC ACIDS

(75) Inventors: Charlotte Moira Norfor Allerton, Sandwich (GB); David John Bull, Sandwich (GB); Mark Edward Bunnage, Sandwich (GB); Robert John Maguire, East Lyme, CT (US); John Steele, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/348,881

(22) Filed: Jan. 22, 2003

(65) Prior Publication Data

US 2003/0199522 A1 Oct. 23, 2003

Related U.S. Application Data

(60) Provisional application No. 60/362,377, filed on Mar. 6, 2002.

(30) Foreign Application Priority Data

Jan. 22, 2002 (GB) ............................................ 0201389
Jan. 29, 2002 (GB) ............................................ 0202027

(51) Int. Cl.[7] ................ A61K 31/4164; A61K 31/4439; C07D 233/64; C07D 403/04

(52) U.S. Cl. ....................... 514/341; 514/397; 514/400; 546/274.1; 548/314.7; 548/339.5; 548/340.1

(58) Field of Search ........................... 548/340.1, 314.7, 548/339.5; 546/274.1; 514/397, 400, 341

(56) References Cited

U.S. PATENT DOCUMENTS 5,993,815 A 11/1999 Bajzar et al. ............ 424/145.1

FOREIGN PATENT DOCUMENTS

| | | | |
|---|---|---|---|
| WO | 0066152 | 11/2000 | .......... A61K/38/55 |
| WO | 0066550 | 11/2000 | ............ C07D/9/38 |
| WO | 0066557 | 11/2000 | ......... C07D/211/34 |
| WO | 0119836 | 3/2001 | ............. C07F/9/30 |
| WO | 0214285 | 2/2002 | ......... C07D/233/64 |

OTHER PUBLICATIONS

McKay et al., Biochemistry, 17(3), pp. 401–405 (1978).

Redlitz et al., J. Clin. Invest., 96, pp 2534–2538 (1995).

Boffa et al., J. Biol. Chem., 273(4), pp. 2127–2135 (1998).

*Primary Examiner*—Laura L. Stockton
(74) *Attorney, Agent, or Firm*—Peter C. Richardson; Garth Butterfield

(57) ABSTRACT

Compounds according to formula (I) wherein n is 0–3, $R^1$ is optionally substituted $C_{1-8}$ alkyl, $C_{2-6}$ alkenyl, or $C_{2-6}$ alkynyl, Heterocycle, Aromatic heterocycle, Aryl or hydrogen and $R^2$, $R^3$, $R^4$, $R^5$, $R^6$, $R^7$, $R^8$ and $R^9$ are each independently selected from hydrogen and optionally substituted $C_{1-6}$ alkyl, or $R^5$ and $R^8$ are an alkylene chain, are novel. They are useful in the treatment of thrombotic conditions and other pathologies associated with fibrin deposition.

(I)

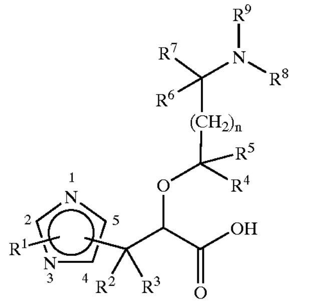

26 Claims, No Drawings

3-(IMIDAZOLYL)-2-ALKOXYPROPANOIC ACIDS

Priority is hereby claimed of previously filed foreign applications, UK 0201389.4, filed Jan. 22, 2002; UK 0202027.9, filed Jan. 29, 2002 (37 C.F.R. §1.55(a)), which was filed under the Paris Convention for the Protection of Industrial Property and was filed in the United Kingdom with, and received by The Patent Office, Cardiff Road, Newport, South Wales, NP10 8QQ; and U.S. Provisional Application No. 60/362,377, filed Mar. 6, 2002.

The present invention relates to a series of novel 3-(imidazolyl)-2-(ω-aminoalkyloxy)propanoic acid derivatives that are inhibitors of TAFIa inhibitors and are useful in the treatment of disease.

BACKGROUND

Sophisticated mechanisms have evolved in mammals to repair the body in the event of vascular injury and so maintain hemostasis. The injured blood vessel constricts to reduce the blood flow to the area, platelets aggregate to reduce the loss of blood from the area, and fibrinogen is cleaved to produce fibrin which then polymerises and forms a clot. This clot covers the area of vascular damage, preventing blood loss. Polymerised fibrin also provides a provisional matrix which enhances the subsequent repair process. Once the blood vessel has been repaired the clot dissolves. The process leading to the formation of the clot is the coagulation cascade, and the process leading to its dissolution is the fibrinolysis cascade. Imbalances in the blood coagulation process are thought to be at the origin of a large and disparate number of disease conditions, which are linked by an unwanted build up of fibrin. The scale of fibrin build up is determined by the delicate equilibrium between the two biochemical cascades in the human body. Agents that can modulate the balance between coagulation and fibrinolysis are therefore potentially valuable in the treatment of these disease conditions.

Studies have shown that coagulation and fibrinolysis are linked through the generation of α-thrombin. α-Thrombin is the final product of the blood coagulation cascade and is responsible for the conversion of fibrinogen into fibrin. In addition to mediating coagulation, α-thrombin also reduces the rate at which blood clots are broken down by the serine protease plasmin. The protein that mediates this antifibrinolytic effect of α-thrombin is TAFI (Thrombin Activatable Fibrinolysis Inhibitor).

TAFI is a 60 kDa glycoprotein found in human plasma. It is also known as procarboxypeptidase B, carboxypeptidase B, plasma carboxypeptidase B, carboxypeptidase U and carboxypeptidase R. Following initiation of the coagulation cascade it is transformed into an activated form, TAFIa, whereupon it acts upon the fibrin matrix of the developing blood clot to prevent its dissolution. TAFI circulates in normal plasma at a concentration of about 75 nM in an inactive form. Thrombin converts the inactive zymogen to the active TAFI (TAFIa), a reaction that is augmented about 1250-fold by thrombomodulin. Once activated, TAFIa cleaves both C-terminal arginine and lysine residues from the developing fibrin clot. The removal of these dibasic amino acids from the surface of the fibrin matrix attenuates clot lysis by inhibiting the binding of the key mediators of fibrinolysis: tissue plasminogen activator (tPA) and its substrate, plasminogen, which is the precursor of plasmin. Both tPA and plasminogen contain a structural motif called a kringle domain which binds tightly to C-terminal lysine residues. The removal of these binding sites prevents the formation of a ternary complex between tPA, plasminogen and fibrin and this inhibits the conversion of plasminogen to plasmin, thus protecting the clot from rapid degradation.

In the presence of a TAFIa inhibitor, TAFIa will not be able to act upon a developing fibrin clot as described above to inhibit fibrinolysis of the clot. Thus a TAFIa inhibitor should serve to enhance fibrinolysis.

It can be seen that, in pathologies where the normal equilibrium between coagulation and fibrinolysis is disturbed in favour of coagulation, there will be a larger amount of fibrin present than normal. This makes it more likely that the subjects will develop one or more of the conditions in which thrombus build up is implicated. Such subjects can be expected to benefit from treatment with a pro-fibrinolytic agent. McKay et al. (*Biochemistry* 1978, 17, 401) disclose the testing of a number of compounds as competitive inhibitors of bovine carboxypeptidase B of pancreatic origin. Inhibition was measured by the inhibitor's efficiency in protecting the active centre tyrosine and glutamic acid of bovine carboxypeptidase B from irreversible alkylation by bromoacetyl-D-arginine or bromoacetamidobutylguanidine. It is suggested that such inhibitors could act as bradykinin potentiators. Bovine enzymes of pancreatic origin are very different to those found in human plasma, so one would not expect inhibitors of one to inhibit the other. Moreover, such inhibitors are directed towards a very different utility. Accordingly this disclosure provides no teaching of TAFIa inhibitors or their utility.

Redlitz et al. (*J. Clin. Invest.* 1995, 96, 2534) teach the involvement of plasma carboxypeptidase B (pCPB, or TAFI) in the formation of clots. The lysis of blood clots was followed in the absence and presence of pCPB, whereupon it was found that the presence of pCPB slowed clot lysis. To confirm that pCPB was responsible two control reactions were run; one where the lysis experiment was repeated in the presence of pCPB and potato carboxypeptidase inhibitor, PCI, and a second where the lysis reaction was conducted in the presence of plasma from which pCPB was removed. In both cases lysis proceeded uninhibited.

Boffa et al. (*J. Biol. Chem.* 1998, 273, 2127) compare plasma and recombinant TAFI and TAFIa with respect to glycosylation, activation, thermal stability and enzymatic properties. Inhibition constants for three competitive inhibitors were determined: ε-aminocaproic acid ε-ACA), 2-guanidinoethylmercaptosuccinic acid (GEMSA) and potato carboxypeptidase inhibitor (PCI).

There are large numbers of carboxypeptidases (i.e. enzymes that cleave the C-terminal amino acid from a peptide). They may be classified as acidic, neutral or basic, depending on the type of amino acid they cleave. Basic carboxypeptidases cleave arginine, lysine and histidine. TAFIa is a member of a specific subset of the basic carboxypeptidases. In terms of the present invention, the inhibitors disclosed above by Redlitz et al. and Boffa et al. are too weak, non-specific or otherwise unsuitable to be considered as suitable TAFIa inhibitors for therapeutic application. Further, whilst the role of TAFIa in clot lysis is explained, there is no suggestion that TAFIa inhibitors can be used to treat disease.

U.S. Pat. No. 5,993,815 teaches the use of a peptide that binds to the TAFI zymogen, thereby inhibiting its activation, to treat those disorders where a C-terminal lysine or arginine is cleaved from an intact peptide. Suitable disorders are arthritis, sepsis, thrombosis, strokes, deep vein thrombosis and myocardial infarctions. The peptide used is an antibody or a functionally active fragment. The peptide should be used in an amount to promote fibrinolysis in vivo.

WO00/66550 and WO00/66557 disclose broad classes of compounds useful as inhibitors of carboxypeptidase U. Inhibitors of carboxypeptidase U are postulated to facilitate fibrinolysis and thus the compounds are taught as useful in the treatment of thrombotic conditions. There is no data to support this assertion, though details of a suitable assay are given.

WO00/66152 discloses formulations containing a carboxypeptidase U inhibitor and a thrombin inhibitor. Suitable carboxypeptidase U inhibitors are those of WO00/66550. The formulations are taught as primarily useful in treating thrombotic conditions.

WO01/19836 discloses a series of phosphonate esters and analogues thereof as carboxypeptidase B inhibitors that are suitable for the treatment or prevention of thrombotic diseases.

WO02/14285 discloses a series of α-imidazolylmethyl-ω-aminocarboxylic acids and $N^{\alpha}$-(ω-aminoalkyl)-histidine derivatives that are inhibitors of TAFIa. The compounds are considered to be potentially useful in the treatment of a number of conditions.

The present invention discloses a further class of TAFIa inhibitors.

DESCRIPTION OF THE INVENTION

In a first aspect, the present invention provides compounds according to general formula (I)

(I)

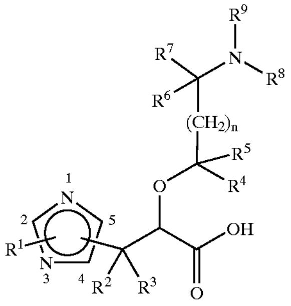

wherein:

n is 0, 1, 2 or 3;

$R^1$ is selected from (a) an optionally substituted straight chain or branched chain $C_{1-6}$ alkyl group, (b) an optionally substituted straight chain or branched chain $C_{2-6}$ alkenyl group, (c) an optionally substituted straight chain or branched chain $C_{2-6}$ alkynyl group, (d) Aryl, (e) Aromatic heterocycle, (f) Heterocycle, and (g) hydrogen;

where the optional substituents in groups (a), (b) and (c) above are selected from: $C_{3-7}$ cycloalkyl, Aryl, Aromatic heterocycle, Heterocycle, $OR^{10}$, $NR^{10}R^{11}$, $S(O)_pR^{10}$, $OC(O)R^{11}$, $CO_2R^{10}$, $CONR^{10}R^{11}$, $SO_2NR^{10}R^{11}$, halo and $NHSO_2R^{10}$, and where p is 0, 1 or 2;

$R^2$, $R^3$, $R^4$, $R^6$, $R^7$ and $R^9$ are each independently selected from hydrogen and straight chain or branched chain $C_{1-6}$ alkyl optionally substituted by $OR^{10}$ or halo;

$R^5$ and $R^8$ are each independently selected from hydrogen and straight chain or branched chain $C_{1-6}$ alkyl optionally substituted by $OR^{10}$ or halo, or together are a $C_{2-6}$ alkylene chain;

$R^{10}$ and $R^{11}$ are each independently selected from hydrogen and straight chain or branched chain $C_{1-6}$alkyl;

Aryl is a 6–14 membered aromatic monocyclic or fused polycyclic carbocyclic group optionally substituted with one or more groups selected from $R^{12}$, halo, $OR^{13}$, $NR^{13}R^{14}$, $NR^{13}CO_2R^{12}$, $CO_2R^{13}$, $NR^{13}SO_2R^{12}$, CN, haloalkyl, O(haloalkyl), $SR^{13}$, $S(O)R^{12}$, $SO_2R^{12}$, $OC(O)R^{13}$, $SO_2NR^{13}R^{14}$, $C(O)NR^{13}R^{14}$, $C_{3-7}$ cycloakyl, O($C_{3-7}$ cycloalkyl), $R^{15}$ and $OR^{15}$, where $R^{12}$ is straight chain or branched chain $C_{1-6}$ alkyl, $R^{13}$ and $R^{14}$ are each independently selected from hydrogen and straight chain or branched chain $C_{1-6}$ alkyl, and $R^{15}$ is phenyl optionally substituted by $R^{12}$, $OR^{13}$, halo or haloalkyl;

Aromatic heterocycle is a 5 to 7 membered aromatic ring containing from 1 to 3 heteroatoms, each independently selected from O, S and N, said ring being optionally substituted with one or more groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{13}$, $NR^{13}R^{14}$, $CO_2R^{13}$, $NR^{13}CO_2R^{14}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$, or a tautomer thereof, or a pharmaceutically acceptable salt or solvate of said compound or said tautomer.

As used herein:

i) Halo includes fluoro, chloro, bromo and iodo groups.

ii) Haloalkyl includes monohaloalkyl, polyhaloalkyl and perhaloalkyl, such as 2-bromoethyl, 2,2,2-trifluoroethyl, chlorodifluoromethyl and trichloromethyl.

iii) Unless otherwise indicated, alkyl includes straight chain and branched chain alkyl.

It will be understood that, in the compounds according to general formula (I), the $R^1$ group and $C(R^2)(R^3)$(amino acid) group may be attached at any atom of the imidazole ring that is available to form a covalent bond, and that it is not intended that the general formula should be interpreted as limiting the $R^1$ group to the $C^2$- and $N^3$-positions, nor the $C(R^2)(R^3)$(amino acid) group to the $C^4$- and $C^5$-positions. It will further be understood that the two groups cannot both be attached to the same atom of the imidazole ring, and that only one of the nitrogen atoms (by convention designated $N^1$) of the imidazole ring is available to form a covalent bond. Thus the possible substitution patterns are 1,2-; 1,4-; 1,5-; 2,4- and 2,5-. When the imidazole is 2,4- or 2,5-substituted then there is a hydrogen atom attached at the $N^1$-position.

Certain compounds according to formula (I) may exist in more than one tautomeric form. If the imidazole of general formula (I) is substituted at the 2- and 4-positions the 2,4-disubstituted imidazole can tautomerise to form the corresponding 2,5-disubstituted imidazole. Furthermore, where a compound includes an Aromatic heterocyle that is substituted with a hydroxyl group it may exist as the 'keto' tautomer. The tautomeric relationship between 2-hydroxypyridine and 2-pyridone is a well known example of this phenomenon. All such tautomers of compounds of formula (I), including mixtures thereof, are included in the scope of the present invention.

The compounds of formula (I) contain one or more asymmetric carbon atoms (chiral centers) and can therefore exist in two or more optical stereoisomeric forms such as enantiomers, diastereomers and epimers. Where the compounds of formula (I) contain a carbon-carbon double bond, cis (Z)/trans (E) stereoisomerism may also occur. All such individual stereoisomers of the compounds of formula (I) and mixtures thereof, including racemates, are included in the scope of the present invention.

Individual stereoisomers may be separated from mixtures by conventional techniques such as, for example, by fractional crystallization or by chromatography of the mixture of compounds or of a suitable salt or derivative thereof. In particular, individual enantiomers of the compounds of formula (I) may be prepared by resolution, such as by H.P.L.C. of the corresponding racemate using a suitable chiral support or by fractional crystallisation of the diastereoisomeric salts formed by reaction of the corresponding racemate with a suitable optically active acid or base, as appropriate. The individual enantiomers may also be obtained from a corresponding optically pure intermediate prepared by such a resolution method. These general principles are discussed in more detail by J. Jacques and A. Collet ("Enantiomers, Racemates and Resolutions", Wiley, N.Y., 1981) and by W. Liu ("Handbook of Chiral Chemicals", D. Ager (ed.), M. Dekker, N.Y., 1999; chapter 8).

It will be appreciated that the compounds of formula (I) have both acidic and basic functional groups. Therefore, in addition to the uncharged form depicted in the general formula, they may exist as internal salts (zwitterions). Furthermore, they may form pharmaceutically acceptable salts with acids and bases. Such zwitterions and salts are included within the scope of the invention.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent. Salts may also be prepared by ion exchange, such as by equilibrating a solution of a compound of formula (I) with an appropriate ion exchange resin. Ion exchange may also be used to convert one salt form of a compound of formula (I), such as a salt with an acid or base that is not pharmaceutically acceptable, to another salt form. These methods are generally well known in the art. Suitable acid addition salts are formed from acids which form non-toxic salts and examples are the hydrochloride, hydrobromide, hydroiodide, sulfate, bisulfate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts. For a review of pharmaceutically acceptable salts see Berge et al. (*J. Pharm. Sci.*, 1977, 66, 1).

The compounds of formula (I) may form pharmaceutically acceptable solvates (including hydrates). These solvates are also included in the scope of the present invention.

The compounds of formula (I) may exist in one or more crystalline forms. These polymorphs, including mixtures thereof are also included within the scope of the present invention.

The scope of the present invention further includes prodrugs of compounds of formula (I), i.e. pharmaceutically acceptable derivatives of the compounds in which one or more of the functional groups explicitly recited above have been modified such that they are converted to the parent compounds in vivo. Suitable prodrugs are discussed in *Drugs of Today* 1983, 19, 499–538 and *Annual Reports in Medicinal Chemistry* 1975, 10, 306–326.

The absolute stereochemistry of the compounds of formula (I) may be as depicted in formula (IA) or formula (IB) below. By convention the absolute stereochemistry at the chiral center of (IA) is designated as 'S' and that of (IB) is 'R'. The compounds of formula (IA) are particularly preferred.

(IA)

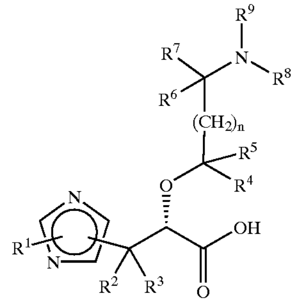

(IB)

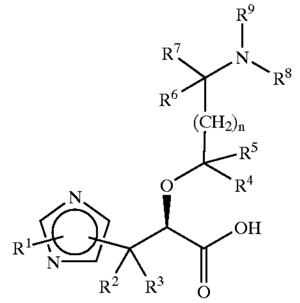

Preferred compounds of formula (I) include those where the imidazole is substituted at the $C^2$ or $C^4$ positions by the $C(R^2)(R^3)$(amino acid) group to give compounds of formulae (IC) and (ID) respectively. Particularly preferred are those compounds of formula (I) where $R^1$ is attached at the $C^4$ position of the imidazole moiety and the $C(R^2)(R^3)$(amino acid) group is attached at the $C^2$ position so as to give the 2,4-disubstituted imidazole of formula ($IC^1$) or where $R^1$ is attached at the $N^1$ position of the imidazole moiety and the $C(R^2)(R^3)$(amino acid) group is attached at the $C^4$ position so as to give the 1,4-disubstituted imidazole of formula ($ID^1$). Most preferred are those compounds of formula (I) where $R^1$ is attached at the $N^1$ position of the imidazole moiety and the $C(R^2)(R^3)$(amino acid) group is attached at the $C^4$ position so as to give the 1,4-disubstituted imidazole of formula ($ID^1$).

(IC)

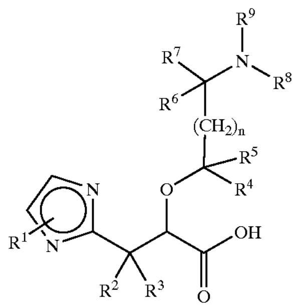

(ID)

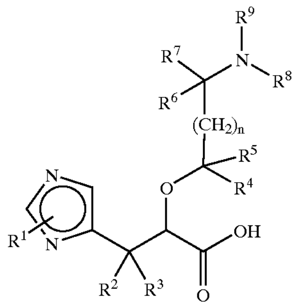

($IC^1$)

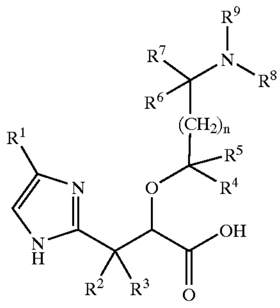

($ID^1$)

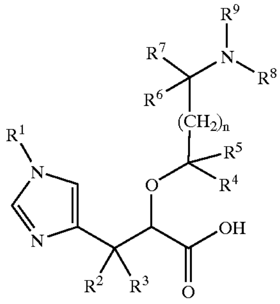

Preferably n is 0 or 1. More preferably n is 0.

Preferably $R^1$ is hydrogen, Aryl, or a $C_{1-6}$ alkyl or $C_{2-6}$ alkenyl group optionally substituted by one or more groups selected from $C_{3-7}$ cycloalkyl, Aryl, Aromatic heterocycle, Heterocycle, $OR^{10}$, $NR^{10}R^{11}$, $S(O)_pR^{10}$, $OC(O)R^{11}$, $CO_2R^{10}$, $CONR^{10}R^{11}$, $SO_2NR^{10}R^{11}$, halo and $NHSO_2R^{10}$. More preferably $R^1$ is hydrogen, Aryl, $C_{2-6}$ alkenyl or a $C_{1-6}$ alkyl group optionally substituted by one or more groups selected from $C_{3-7}$ cycloalkyl, Aryl, Aromatic heterocycle, $OR^{10}$, $CO_2R^{10}$, halo and $NHSO_2R^{10}$. Yet more preferably $R^1$ is hydrogen, Aryl or a $C_{1-6}$ alkyl group optionally substituted by a group selected from $C_{3-7}$ cycloalkyl, Aryl, Aromatic heterocycle, $OR^{10}$, $CO_2R^{10}$ and $NHSO_2R^{10}$. Yet more preferably $R^1$ is hydrogen, Aryl or a $C_{1-6}$ alkyl group optionally substituted by a group selected from cyclohexyl and Aryl. Yet more preferably $R^1$ is hydrogen or $C_{1-3}$ alkyl. Most preferably $R^1$ is hydrogen.

Preferably $R^2$ and $R^3$ are each independently selected from hydrogen and $C_{1-6}$ alkyl More preferably $R^2$ and $R^3$ are hydrogen.

Preferably $R^4$ is hydrogen or $C_{1-6}$ alkyl. More preferably $R^4$ is hydrogen.

Preferably $R^6$, $R^7$ and $R^9$ are each independently selected from hydrogen and $C_{1-6}$ alkyl. More preferably $R^6$, $R^7$ and $R^9$ are each independently selected from hydrogen and $C_{1-3}$ alkyl. Yet more preferably $R^6$, $R^7$ and $R^9$ are each independently selected from hydrogen and methyl. Most preferably $R^6$, $R^7$ and $R^9$ are all hydrogen.

When $R^5$ and $R^8$ do not constitute a $C_{2-6}$ alkylene link then $R^5$ is preferably hydrogen or $C_{1-6}$ alkyl, more preferably hydrogen or $C_{1-3}$ alkyl, yet more preferably hydrogen or methyl, and most preferably methyl, and $R^8$ is preferably hydrogen or $C_{1-6}$ alkyl, more preferably hydrogen or $C_{1-3}$ alkyl, yet more preferably hydrogen or methyl, and most preferably hydrogen.

When $R^5$ and $R^8$ constitute a $C_{2-6}$ alkylene link then the link is preferably a $C_{2-3}$ alkylene link and more preferably it is a $C_2$ alkylene link.

Preferably $R^{10}$ and $R^{11}$ are each independently selected from hydrogen and $C_{1-3}$ alkyl. More preferably $R^{10}$ and $R^{11}$ are each independently selected from hydrogen and methyl.

Aryl includes optionally substituted phenyl, naphthyl, anthracenyl and phenanthrenyl. Preferably Aryl is phenyl or naphthyl optionally substituted by 1–3 groups selected from $R^{12}$, halo, $OR^{13}$, $NR^{13}R^{14}$, $NR^{13}CO_2R^{12}$, $CO_2R^{13}$, $NR^{13}SO_2R^{12}$, CN, haloalkyl, O(haloalkyl), $SR^{13}$, $S(O)R^{12}$, $SO_2R^{12}$, $OC(O)R^{13}$, $SO_2NR^{13}R^{14}$, $C(O)NR^{13}R^{14}$, $C_{3-7}$ cycloakyl, $O(C_{3-7}$ cycloalkyl), $R^{15}$ and $OR^{15}$. More preferably Aryl is phenyl optionally substituted by $C_{1-6}$ alkyl, halo, $O(C_{1-6}$ alkyl), $CF_3$, $C_{3-7}$ cycloakyl, $O(C_{3-7}$ cycloalkyl), $R^{15}$ or $OR^{15}$ and $R^{15}$ is phenyl optionally substituted by $C_{1-6}$ alkyl, halo, $O(C_{1-6}$ alkyl) or $CF_3$. Yet more preferably Aryl is phenyl optionally substituted by $C_{1-6}$ alkyl, $CF_3$, cyclohexyl, O(cyclohexyl), $R^{15}$ or $OR^{15}$ and $R^{15}$ is phenyl optionally substituted by $C_{1-6}$ alkyl, Cl, F, $O(C_{1-6}$ alkyl) or $CF_3$. Most preferably Aryl is phenyl.

Preferably Aromatic heterocycle is a 5 or 6 membered aromatic ring containing 1 or 2 heteroatoms each independently selected from O, S and N, including optionally substituted furyl, thienyl, pyrrolyl, oxazolyl, isoxazolyl, thiazolyl, isothiazolyl, imidazolyl, oxadiazolyl, thiadiazolyl, triazolyl, pyridyl, pyridazinyl, pyrimidinyl, pyrazinyl and triazinyl, optionally substituted by 1–3 groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$, $C(O)NR^{13}R^{14}$. More preferably Aromatic heterocycle is a 5 or 6 membered aromatic ring containing from 1 to 3 heteroatoms, each independently selected from O, S and N, optionally substituted by 1–3 groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$, $C(O)NR^{13}R^{14}$. Most preferably Aromatic heterocycle is an unsubstituted 5 or 6 membered aromatic ring containing 1 or 2 heteroatoms, each independently selected from O, S and N.

Preferably, Heterocycle is a 3 to 8 membered ring containing 1 or 2 heteroatoms, each independently selected from O, S and N, said ring being saturated or partially saturated, optionally substituted by 1 to 3 groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$, $C(O)NR^{13}R^{14}$. More preferably, Heterocycle is a 5 or 6 membered ring containing 1 or 2 heteroatoms, each independently selected from O, S and N, said ring being saturated or partially saturated, optionally substituted by 1 to 3 groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$, $C(O)NR^{13}R^{14}$. Most preferably, Heterocycle is an unsubstituted 5 or 6 membered ring containing 1 or 2 heteroatoms, each independently selected from O, S and N, said ring being saturated or partially saturated, including oxiranyl, azetidinyl, tetrahydrofuranyl, thiolanyl, pyrrolidinyl, dioxolanyl, dihydropyranyl, tetrahydropyranyl, morpholinyl, piperidinyl and piperazinyl.

Preferred compounds of the present invention are:

(2S)-(−)-2-(2-aminoethoxy)-3-(1-phenyl-1H-imidazol-4-yl)propanoic acid (Example 6);

(2S)-2-{[(1R)-2-amino-1-methylethyl]oxy}-3-[1-(2-cyclohexylethyl)-1H-imidazol-4-yl]propanoic acid (Example 15);

(2S)-2-{[(1R)-2-amino-1-methylethyl]oxy}-3-(1-phenyl-1H-imidazol-4-yl)propanoic acid (Example 17);

(2S)-2-{[(2S)-2-aminopropyl]oxy}-3-[1-(2-cyclohexylethyl)-1H-imidazol-4-yl]propanoic acid (Example 34);

(2S)-2-(2-aminoethoxy)-3-(1H-imidazol-4-yl)propanoic acid (Example 50);

(2S)-2-{[(1R)-2-amino-1-methylethyl]oxy}-3-(1H-imidazol-4-yl)propanoic acid (Example 51); and (2S)-2-{[(1R)-2-amino-1-methylethyl]oxy}-3-[1-(2-pyridinyl)-1H-imidazol-4yl]propanoic acid (Example 52).

Particularly preferred is (2S)-2-{[(1R)-2-amino-1-methylethyl]oxy}-3-(1H-imidazol-4-yl)propanoic acid (Example 51).

The compounds of formula (I) are inhibitors of TAFIa. Inhibition of TAFIa can be demonstrated using an assay based on the method of Boffa et al. (*J. Biol. Chem.* 1998, 273, 2127) as further described below. The activity of the compounds is characterized by a calculated $K_i$ value. Generally the compounds of the present invention have a $K_i$ value of 10 $\mu$M or less. Better compounds have a $K_i$ value of 1 $\mu$M or less, or even 100 nM or less. The most potent compounds have a $K_i$ value of 25 nM or less.

The compounds of formula (I) are selective for TAFIa over other carboxypeptidases, and particularly carboxypeptidase N (CPN). Unwanted inhibition of CPN is considered to be the most likely cause of undesirable side effects in clinical use. Selectivity can be expressed as the ratio of the $K_i$ for TAFIa to the $K_i$ for CPN. Generally the compounds of the present invention have a selectivity ratio of at least 5. Better compounds have a selectivity ratio of at least 10. The most selective compounds have a selectivity ratio of at least 50.

The compounds of formula (I) may be prepared according to the general methods which are described below and in the Examples and Preparations section. These methods provide a further aspect of the present invention. Nevertheless, the skilled man will appreciate that the compounds of the invention could be made by methods other than those herein described, by adaptation of the methods herein described and/or adaptation of a plethora of methods known in the art. It is to be understood that the synthetic transformation methods specifically mentioned herein may be carried out in various different sequences in order that the desired substances can be efficiently assembled. The skilled chemist will exercise his judgement and skill as to the most efficient sequence of reactions for the synthesis of a given target substance.

It will be apparent to those skilled in the art that sensitive functional groups may need to be protected and deprotected during the synthesis of a substance of the invention. This may be achieved by conventional techniques, for example as described by T. W. Greene and P. G. M. Wuts ("Protective Groups in Organic Synthesis", $3^{RD}$ edition, Wiley-Interscience, N.Y., 1999).

Compounds of formula (I) may be prepared from the corresponding esters of formula (II) (wherein $P^1$ is a lower alkyl group, a benzyl group or any other carboxyl protecting group).

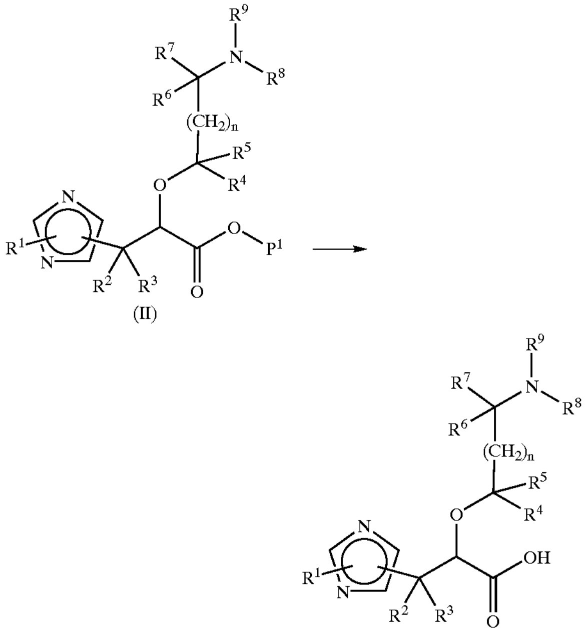

(II) → (I)

$P^1$ is preferably a lower alkyl group such as methyl or ethyl, in which case suitable conditions for this step include treatment with NaOH in dioxan for 1–3 days.

Compounds of formula (II) may be prepared from the corresponding protected amines of formula (III) (wherein $p^2$ is a tert-butyloxycarbonyl, benzyloxycarbonyl or fluorenylmethyloxycarbonyl group, or any other amine protecting group). Where $R^9$ is H then the preparation involves only a deprotection step. Where $R^9$ is other than H then a further step is necessary to introduce $R^9$, such as a reductive amination reaction.

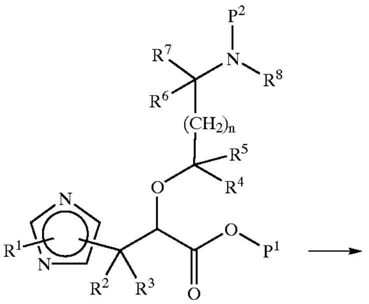

(III)

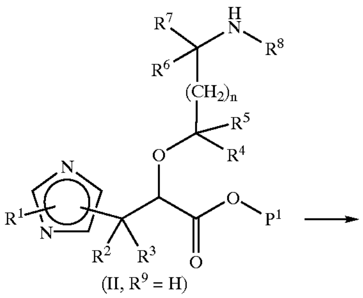

(II, $R^9$ = H)

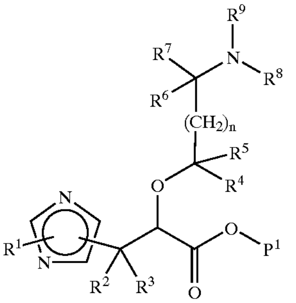

(II)

Alternatively, compounds of formula (III) may be converted to the corresponding acids (IV) prior to deprotecting the amine to give the compounds of formula (I).

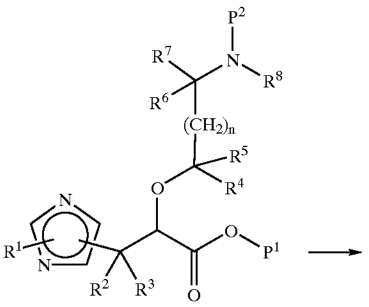

(III)

-continued

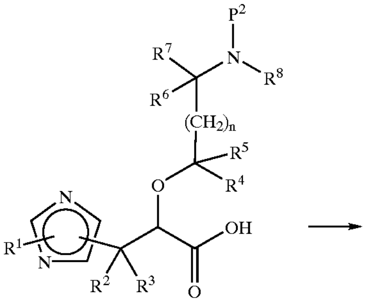

(IV)

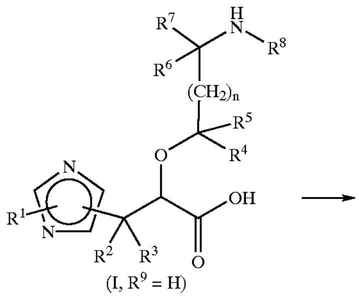

(I, $R^9$ = H)

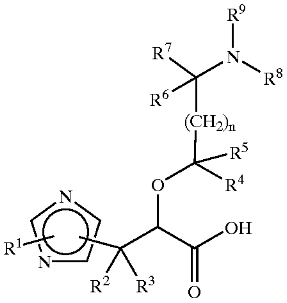

(I)

Compounds of formula (III) may be prepared from imidazoleacetic acid derivatives of formula (V), wherein X is a leaving group such as a chlorine, bromine or iodine atom, or a methanesulphonate or trifluoromethanesulphonate group, by reaction with a alcohol of formula (VI).

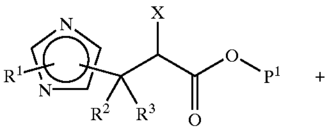

(V)

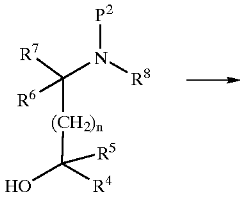

(VI)

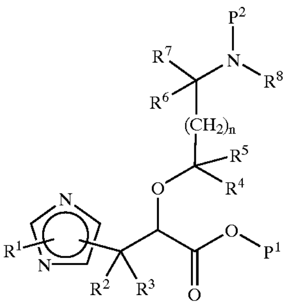

(III)

Compounds of formula (V) may be prepared from the corresponding hydroxyacid derivatives of formula (VII) or, where X is Br, by direct halogenation of the esters of formula (VIII).

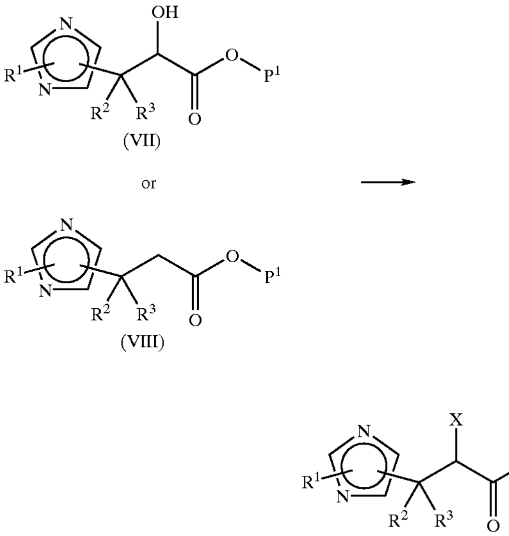

(VII) or (VIII) (V)

Compounds of formula (VI), (VII) and (VIII) are known or may be prepared by methods analogous to those used for the preparation of such known compounds.

Compounds of formula (III) may alternatively be prepared from α-hydroxyimidazole-acetic acid derivatives of formula (VII) by reaction with a compound of formula (IX) wherein Y is a leaving group such as a chlorine, bromine or iodine atom, or a methanesulphonate or trifluoromethanesulphonate group.

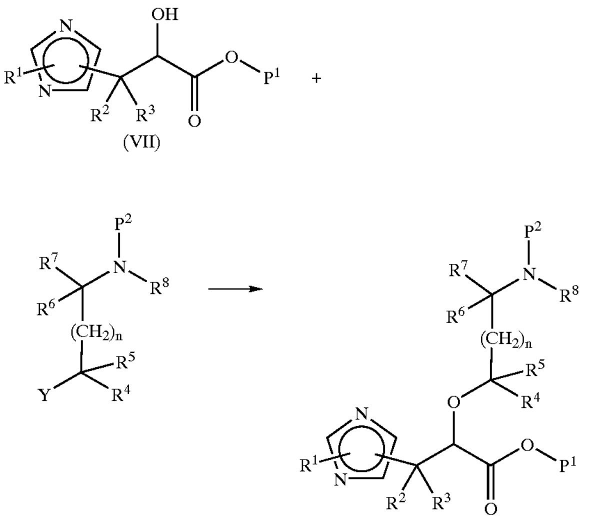

(VII) + (IX) (III)

Compounds of formula (II) where neither of $R^8$ and $R^9$ are hydrogen may also be prepared from compounds of formula (X). When $R^3$ is hydrogen the transformation may be accomplished by hydrogenation in the presence of a suitable catalyst. When $R^3$ is other than hydrogen the transformation may be accomplished using a reagent such as $R^3$-M, where M is a metal such as lithium or magnesium, in the presence of a copper(I) salt.

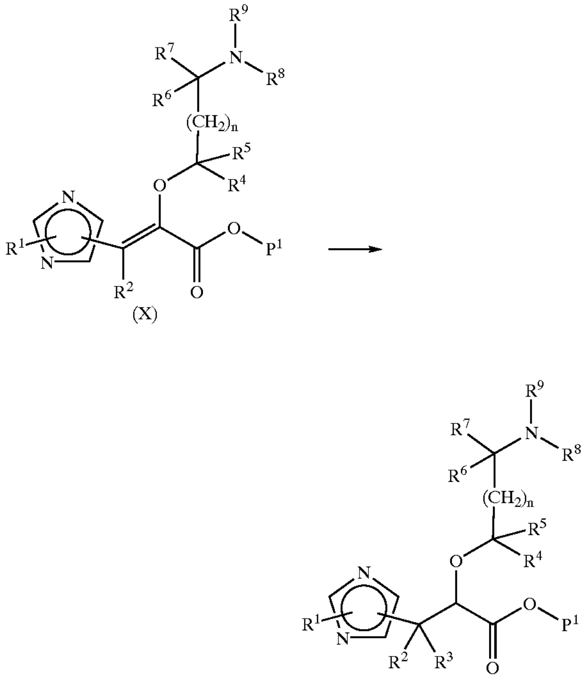

(X) (II)

Compounds of formula (X) may be prepared from compounds of formula (XI) by dehydration. The transformation may be accomplished using, for example, methanesulfonyl chloride and a tertiary amine.

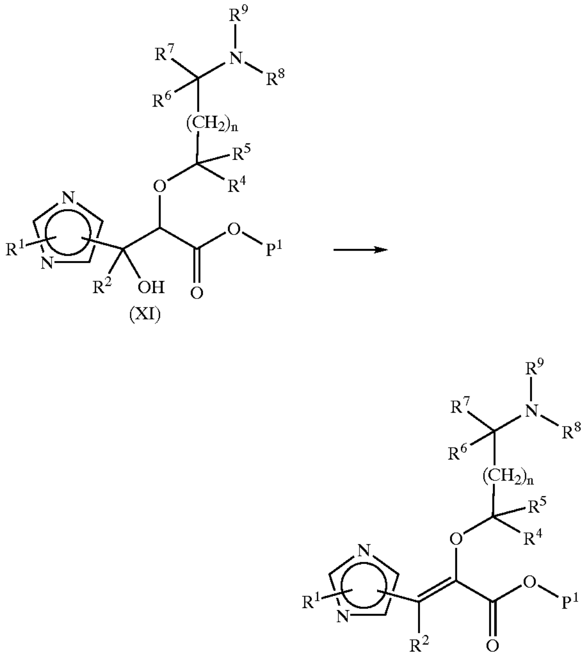

(XI) (X)

Compounds of formula (XI) may be prepared by an aldol-type reaction between alkoxy-esters of formula (XII) and aldehydes or ketones of formula (XIII) in the presence of a strong base, such as lithium diisopropylamide.

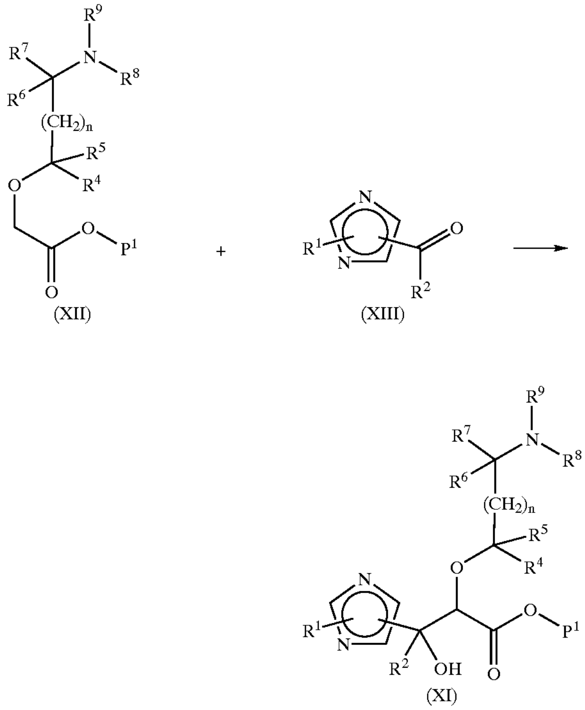

(XII) (XIII) (XI)

Compounds of formula (XIII) are generally known, or may be prepared by methods analogous to published methods. Compounds of formula (XII) may be prepared by reacting the corresponding amino-alcohols $R^8R^9NC(R^6)(R^7)(CH_2)_nC(R^4)(R^5)OH$ with a bromoacetate $BrCH_2CO_2P^1$ in the presence of a base such as sodium hydride.

Compounds of formula (I) wherein $R^9$ is hydrogen may alternatively be prepared by the hydrolysis of lactams of formula (XIV).

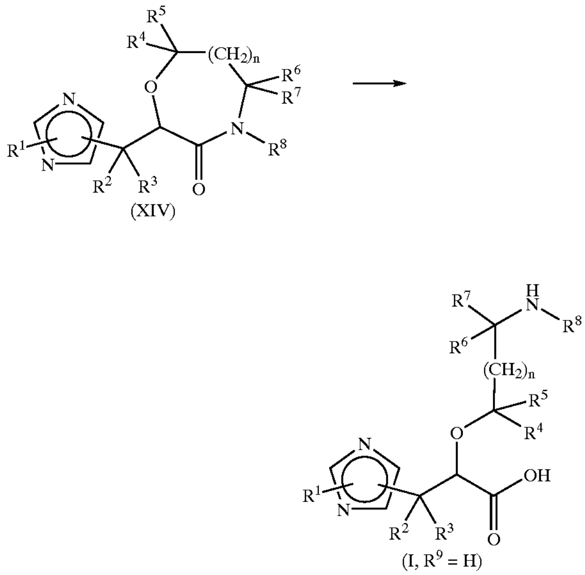

(XIV) (I, $R^9$ = H)

Compounds of formula (XIV) may be prepared from the corresponding unsaturated compounds of formula (XV). When $R^3$ is hydrogen the transformation may be accomplished by hydrogenation in the presence of a suitable catalyst. When $R^3$ is other than hydrogen the transformation may be accomplished using a reagent such as $R^3$—M, where M is a metal such as lithium or magnesium, in the presence of a copper(I) salt.

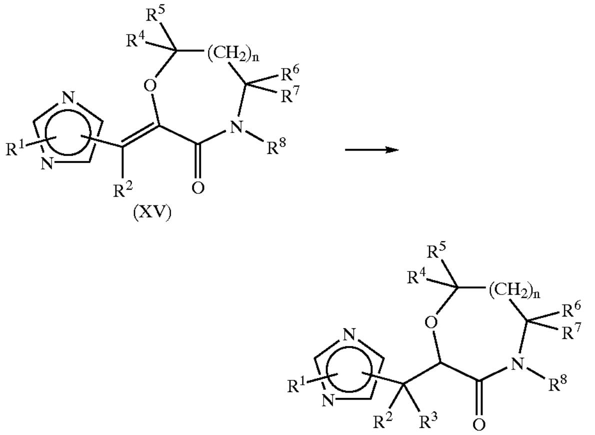

(XV) (XIV)

Compounds of formula (XV) may be prepared by dehydration of alcohols of formula (XVI).

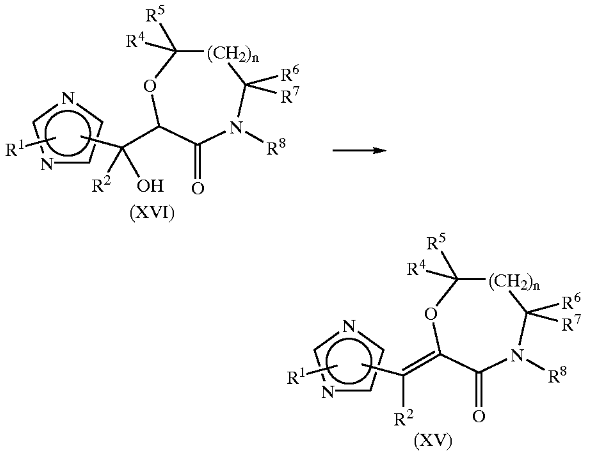

(XVI) (XV)

Compounds of formula (XVI) may be prepared by reacting an aldehyde or ketone of formula (XIII) with a lactam of formula (XVII) in the presence of a strong base, such as lithium diisopropylamide.

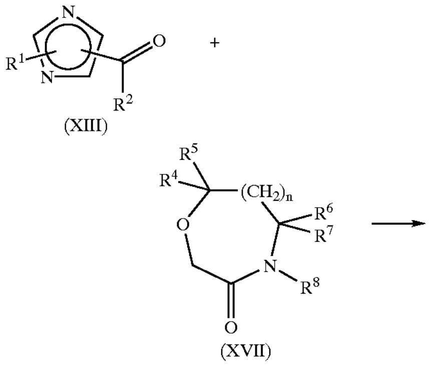

(XIII) (XVII)

-continued

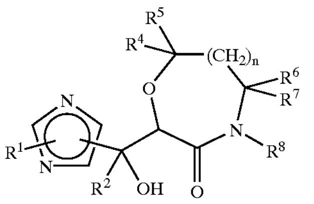

(XVI)

Compounds of formula (XVII) may be prepared from aminoalcohols of formula (XVIII) by reaction with chloroacetyl chloride. Compounds of formula (XVIII) are generally known, or may be prepared by adaptation of generally known methods.

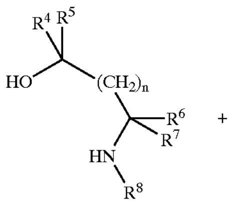

(XVIII)

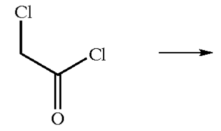

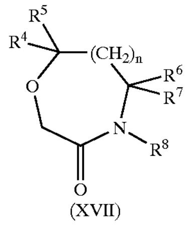

(XVII)

When $R^8$ is H, the foregoing method can be problematic, particularly at the step involving the reaction of compounds of formula (XIII) and (XVII). It is generally convenient in this case to use a protected aminoalcohol of formula (XVIIIa), where $P^3$ is a nitrogen protecting group. A particularly useful embodiment of $P^3$ is the 4-methoxybenzyl group. This may be removed following the elaboration of intermediate (XIVa) by treatment with ceric ammonium nitrate.

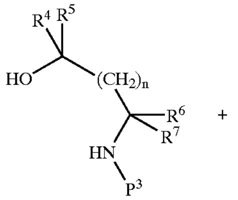

(XVIIIa)

-continued

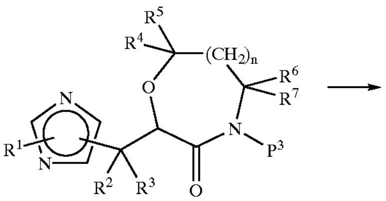

(XIVa)

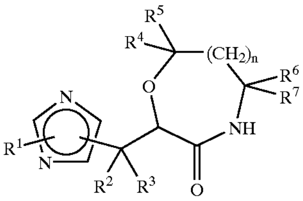

(XIV, $R^8$ = H)

When $R^1$ is H it may be necessary or convenient to protect the imidazole as its trityl derivative. Accordingly, when $R^1$ is H, compounds of formula (XIX), (XX) or (XXI) may be elaborated by the foregoing methods to provide compounds of formula (XXII) which, upon deprotection, give compounds of formula (III).

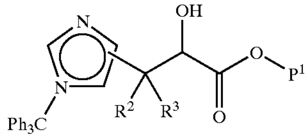

(XIX)

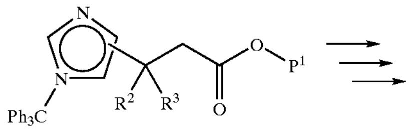

(XX)

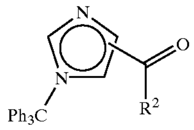

(XXI)

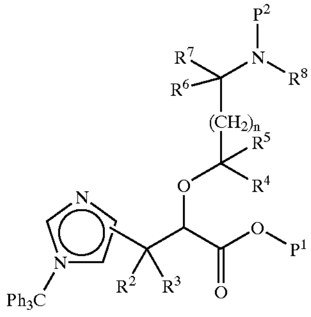

(XXII)

This route may also be useful for the preparation of certain compounds according to formula (I) wherein $R^1$ is attached at the $N^1$ position of the imidazole ring. Compounds of formula (III) wherein $R^1$ is H may be alkylated or arylated to give compounds of formula (III) wherein $R^1$ is other than H and is attached at the $N^1$ position.

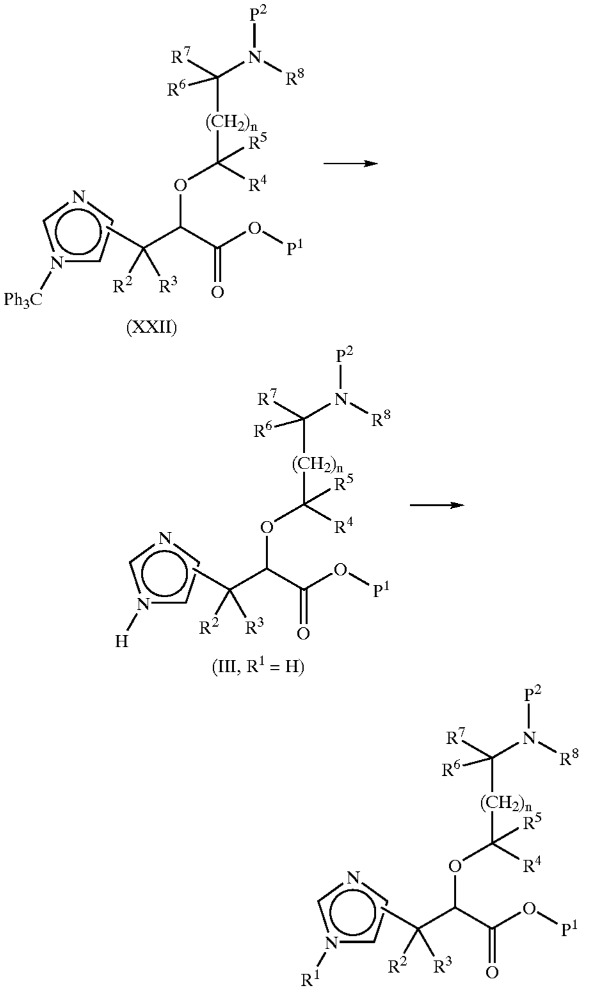

(XXII)

(III, $R^1$ = H)

(III, $R^1$ at $N^1$)

When $R^1$ is an alkyl, alkenyl or alkynyl group it may be introduced in an alkylation reaction. Suitable conditions for this step include treatment with 1.1 eq of cesium carbonate and 1.1 eq of an alkylating agent in N,N-dimethylformamide, or with sodium hydride and 1.1 eq of an alkylating agent in THF. Suitable alkylating reagents include $R^1$—Cl, $R^1$—Br, $R^1$—I, $R^1$—$OSO_2CH_3$ and $R^1$—$OSO_2CF_3$. When $R^1$ is Aryl or Aromatic heterocycle it may be introduced in an arylation reaction. Suitable conditions for this step include treatment with 2 eq of Aryl-B$(OH)_2$ or Aromatic heterocycle-B$(OH)_2$ in the presence of 1.5 eq of copper acetate, 2 eq of pyridine, air and 4 Å molecular sieves.

For the compounds of formula (I) wherein the imidazole is 2,4- or 2,5-disubstituted, it may also be convenient or necessary to use a protecting group at the $N^1$ position.

The compounds of formula (I) are useful as therapeutic agents. The compounds will generally be formulated so as to be amenable to administration to the subject by the chosen route. In a further aspect, therefore, the present invention provides for a pharmaceutical composition comprising a compound of formula (I) or a stereoisomer, tautomer or pharmaceutically acceptable salt, solvate or prodrug thereof and a pharmaceutically acceptable excipient, diluent or carrier selected with regard to the intended route of administration and standard pharmaceutical practice. For example, the compounds of formula (I) can be administered orally, buccally or sublingually in the form of tablets, capsules, ovules, elixirs, solutions or suspensions. These formulations may contain flavouring or colouring agents, and may be adapted for immediate-, delayed-, modified-, sustained-, pulsed- or controlled-release applications.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose and derivatives thereof, milk sugar and high molecular weight polyethylene glycols.

For solutions, suspensions and elixirs, the compounds of formula (I) may be combined with various sweetening or flavouring agents, colouring matter or dyes, with emulsifying and/or suspending agents, and with diluents such as water, ethanol, propylene glycol and glycerin, and combinations thereof.

The compounds of formula (I) may also be administered in the form of a solution- or suspension-filled soft or hard gelatin capsule. Such capsules are generally made of gelatin, glycerin, water and sorbitol. Hard capsules are distinguished from soft capsules by containing less water and thus having a correspondingly stronger shell. Additional excipients suitable for use in such capsules include propylene glycol, ethanol, water, glycerol and edible oils.

The compounds of formula (I) can also be administered parenterally, for example, intravenously, intra-arterially, intraperitoneally, intrathecally, intraventricularly, intraurethrally, intrasternally, intracranially, intramuscularly or subcutaneously. Such administration may be as a single bolus injection or as a short- or long-duration infusion. For such parenteral administration the compounds are preferably formulated as a sterile solution in water or another suitable solvent or mixture of solvents. The solution may contain other substances such as: salts, particularly sodium chloride, and sugars, particularly glucose or mannitol, to make the solution isotonic with blood; buffering agents such as acetic, citric and phosphoric acids and their sodium salts, such that the pH of the solution is preferably between 3 and 9; and preservatives. The preparation of suitable parenteral formulations under sterile conditions is readily accomplished by standard pharmaceutical techniques well known to those skilled in the art.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant such as dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Alternatively, the compounds of formula (I) can be administered by the vaginal or rectal routes in the form of a suppository or pessary, or The compounds of formula (I) may also be administered dermally or transdermally, for example, by the use of a skin patch.

Alternatively, the compounds of formula (I) can be applied topically in the form of a gel, hydrogel, lotion, solution, cream, ointment or dusting powder. Suitable ointments may contain the active compound suspended or dissolved in, for example, a mixture with one or more of the following: mineral oil, liquid petrolatum, white petrolatum, propylene glycol, polyoxyethylene polyoxypropylene compound, emulsifying wax and water. Suitable lotions or creams may contain the active compound suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Alternatively, the compounds of formula (I) may be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The compounds of formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

Because the compounds of formula (I) are inhibitors of TAFIa they are useful as therapeutic agents in pathologies in which inhibition of TAFIa is beneficial. In a further aspect, therefore, the present invention provides for a compound of formula (I) or a stereoisomer, tautomer, solvate, pharmaceutically acceptable salt or prodrug thereof for use as a medicament. In particular, the present invention provides for the use of a compound of formula (I) or a stereoisomer, tautomer, solvate, pharmaceutically acceptable salt or prodrug thereof in the preparation of a medicament for the treatment or prevention of a condition selected from thrombotic conditions, atherosclerosis, adhesions, dermal scarring, cancer, fibrotic conditions, inflammatory diseases and those conditions which benefit from maintaining or enhancing bradykinin levels in the body. The utility of TAFIa inhibitors for the treatment of thrombotic conditions derives from their potential to promote fibrinolysis while not interfering with coagulation. In most clinically relevant situations thrombus formation is sub-acute, i.e. the thrombus forms slowly. Conventional anti-thrombotic agents block the coagulation pathway and so prevent thrombus growth, but as an unavoidable consequence they also block the clotting response to vascular damage, which results in an increased incidence of hemorrhaging. By promoting fibrinolysis, TAFIa inhibitors accelerate the dissolution of the developing thrombus without interfering with the clotting response. Accordingly, one preferred embodiment of the present invention provides for the use of a compound of formula (I) or a pharmaceutically acceptable salt, solvate or prodrug thereof in the preparation of a medicament for the treatment of a thrombotic condition selected from myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events following surgical revascularisation or intervention, or for improving the outcome of organ transplantation by reducing blood clotting and so preserving organ function. Cardiovascular events following intervention surgery include conditions such as restenosis or reocclusion following interventions such as percutaneous transluminal coronary angioplasty, grafting, stent in-placement, coronary bypass surgery or any other forms of surgical revascularisation or intervention. Disseminated intravascular coagulation includes all conditions resulting from intravascular activation of the coagulation process. This might occur acutely through the release of procoagulant substances (eg. obstetric emergencies, snakebite, crush injury malignancy), by abnormal contact of the blood (eg. infections, burns, extracorporeal circulation, grafts) or though generation of procoagulants in the blood (transfusion reactions, leukemia); or chronically, (eg. toxemia, malignant hypertension, severe liver cirrhosis). Deep vein thrombosis also encompasses what is known as 'economy class syndrome', where clots form in subjects forced to endure cramped conditions for a period of time, such as those sitting in the economy class seats of an aeroplane.

A role for thrombus formation in the pathophysiology of atherosclerosis has recently been highlighted by several independent groups. Non-occlusive thrombi not only restrict blood flow leading to myocardial ischemia and angina pectoris but also, due to incomplete endogenous lysis, may be incorporated into the arterial wall as solidified plaque material enhancing the atherosclerotic process. Long-term administration of a TAFIa inhibitor promotes the lysis of developing thrombi and therefore provides a safe and efficacious treatment which alleviates the symptoms of angina pectoris while impairing the progression of the underlying disease. Conventional treatment of myocardial ischaemia in clinically stable coronary artery disease is predominately designed to reduce cardiac workload and enhance blood flow. Such approaches clearly reduce myocardial ischaemia thus increasing quality of life. However, these strategies have little effect on the pathogenesis of coronary atherosclerosis which is a chronic process of continuous remodeling of the vascular tree in response to varying degrees of vascular injury. Accordingly, another preferred embodiment of the present invention provides for the use of compounds of formula (I) and pharmaceutically acceptable salts, solvates and prodrugs thereof in the preparation of a medicament for the treatment or prevention of atherosclerosis, including atherosclerosis as a consequence of peripheral vascular disease, insulin resistance and Syndrome X, and further including myocardial ischaemia and angina pectoris resulting from atherosclerosis. Atherosclerosis is taken to include both primary and secondary coronary artery disease, in which atherosclerosis restricts the blood supply to the heart. Primary prevention of coronary artery disease means preventing the onset of ischemic complications such as myocardial infarction in patients with no history of coronary artery disease but who have one or more risk factors. Secondary prevention of coronary artery disease means preventing ischemic complications in patients with established coronary artery disease, such as patients who have had a previous myocardial infarction. Syndrome X is a term often used to group together a number of interrelated diseases. The first stage of syndrome X consists of insulin resistance, abnormal cholesterol and triglyceride levels, obesity and hypertension. Any one of these conditions may be used to diagnose the start of Syndrome X. The disease may then progress with one condition leading to the development of another in the group. For example insulin resistance is associated with high lipid levels, hypertension and obesity. The disease then cascades, with the development of each additional condition increasing the risk of developing more serious diseases. This can progress to the development of diabetes, kidney disease and heart disease. These diseases may lead to stroke, myocardial infarction and organ failure. Atherosclerosis is common in patients with Syndrome X.

TAFIa inhibitors are also effective in preventing the formation of adhesions in the body. Most surgical procedures and physical traumas result in bleeding into the cavities between tissues. The blood which collects at these sites then clots forming fibrin-rich thrombi. These thrombi bridge the gaps between adjacent tissues and act as foci for the accumulation of inflammatory cells and fibroblasts. Invading fibroblasts lay down a collagen-rich extracellular matrix which strengthens the adhesion of the tissues producing a firm bond which may then restrict movement. Adhesions have been characterised according to their location and may result following any surgery, e.g. abdominal, orthopaedic, neurological, cardiovascular and ocular surgery. This inappropriate adhesion of tissues post-surgery or trauma is a major issue which can lead to various outcomes, e.g. "aches and pains", "twinges", local inflammation, restriction in mobility, pain, intestinal obstruction and sometimes, in the most severe cases, death. In the case of gynaecological surgery, infertility may result. Additionally clots forming fibrin-rich thrombi are implicated in dermal scarring and restenosis. Without being bound by any theory, it is believed that adhesion formation may be enhanced when a deficiency in fibrinolysis results in enhanced and maintained clot formation. Treatment with a TAFIa inhibitor around and/or after surgical intervention may enhance fibrinolysis of the fibrin-rich thrombi and hence inhibit thrombus formation, accretion and stabilization, thereby inhibiting adhesion formation. A TAFIa inhibitor given either locally as a topical application or systemically may be seen to be of benefit in a range of surgical procedures. In addition, administration of a TAFIa inhibitor may be used to treat adhesions resulting from other forms of non-surgical physical trauma where this has caused internal bleeding. Examples of such trauma might include sporting injuries or anything else resulting in a tear, cut, bruise or induration of the body. Accordingly, another preferred embodiment of the present invention provides for the use of compounds of formula (I) and pharmaceutically acceptable salts, solvates and prodrugs thereof in the preparation of a medicament for the treatment or prevention of a medicament for the treatment or prevention of adhesions or dermal scarring.

TAFIa inhibitors are also effective in inhibiting tumour maturation, progression and metastasis. Without being bound by any theory, it is believed that the hemostatic system is involved at several levels of cancer pathology, including neovascularisation, shedding of cells from the primary tumour, invasion of the blood supply, adherence to the vessel wall and growth at the metastatic site. It is thought that the efficacy of TAFIa inhibitors stems from an ability to reduce fibrin deposition around solid tumours and thereby inhibit the above processes. Accordingly, another preferred embodiment of the present invention provides for the use of compounds of formula (I) and pharmaceutically acceptable salts, solvates and prodrugs thereof in the preparation of a medicament for the treatment or prevention of cancer.

TAFIa inhibitors are efficacious in treatment of any condition in which fibrosis is a contributing factor. Suitable fibrotic conditions include cystic fibrosis, pulmonary fibrotic diseases such as chronic obstructive pulmonary disease (COPD), adult respiratory distress syndrome (ARDS), fibromuscular dysplasia and fibrotic lung disease, and fibrin deposition in the eye during opthalmic surgery. Accordingly, another preferred embodiment of the present invention provides for the use of compounds of formula (I) and pharmaceutically acceptable salts, solvates and prodrugs thereof in the preparation of a medicament for the treatment or prevention of fibrotic disease, and in particular for the treatment or prevention of a fibrotic condition selected from cystic fibrosis, pulmonary fibrotic diseases, chronic obstructive pulmonary disease (COPD), adult respiratory distress syndrome (ARDS), fibromuscular dysplasia, fibrotic lung disease and fibrin deposition in the eye during opthalmic surgery.

TAFIa inhibitors are efficacious in the treatment of inflammation, inflammatory diseases such as asthma, arthritis, endometriosis, inflammatory bowel diseases, psoriasis and atopic dermatitis and neurodegenerative diseases such as Alzheimer's disease and Parkinson's disease. Accordingly, another preferred embodiment of the present invention provides for the use of compounds of formula (I) and pharmaceutically acceptable salts, solvates and prodrugs thereof in the preparation of a medicament for the treatment or prevention of inflammation, inflammatory diseases such as asthma, arthritis, endometriosis, inflammatory bowel diseases, psoriasis and atopic dermatitis and neurodegenerative diseases such as Alzheimer's disease and Parkinson's disease.

TAFIa binds to and breaks down bradykinin (Tan et al., *Biochemistry* 1995, 34, 5811). There are many conditions which are known to benefit from maintaining or enhancing levels of bradykinin such as hypertension, angina, heart failure, pulmonary hypertension, renal failure and organ failure. Accordingly, another preferred embodiment of the present invention provides for the use of compounds of formula (I) and pharmaceutically acceptable salts, solvates and prodrugs thereof in the preparation of a medicament for the treatment or prevention of conditions which benefit from maintaining or enhancing levels of bradykinin.

In a further aspect, the present invention provides a method of treating or preventing thrombotic conditions, atherosclerosis, adhesions, dermal scarring, cancer, fibrotic conditions, inflammatory diseases and those conditions which benefit from maintaining or enhancing bradykinin levels in the body which comprises administering a therapeutically effective amount of a compound of formula (I) or a stereoisomer, tautomer or pharmaceutically acceptable salt, solvate or prodrug thereof to a patient in need of such treatment.

One preferred embodiment of the present invention provides for a method of treating or preventing thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and preventing cardiovascular events following intervention surgery which comprises administering a therapeutically effective amount of a compound of formula (I) or a stereoisomer, tautomer or pharmaceutically acceptable salt, solvate or prodrug thereof to a patient in need of such treatment. Subjects with thrombotic conditions who are suitable for treatment by the present invention include those having conditions associated with hypercoagulability, such as factor V mutation, antithrombin III deficiency, heparin cofactor II deficiency, protein C deficiency, protein S deficiency and polycythemia vera, and those exhibiting homocystinaemia or homocystinuria.

Another preferred embodiment of the present invention provides for a method of treating or preventing atherosclerosis which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing adhesions or dermal scarring which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing cancer which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing a fibrotic condition such as cystic fibrosis, pulmonary fibrotic diseases, chronic obstructive pulmonary disease (COPD), adult respiratory distress syndrome (ARDS), fibromuscular dysplasia, fibrotic lung disease and fibrin deposition in the eye during ophthalmic surgery which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing an inflammatory disease such as asthma, arthritis, endometriosis, inflammatory bowel diseases, psoriasis or atopic dermatitis or a neurodegenerative disease such as Alzheimer's disease or Parkinson's disease which comprises administering a therapeutically effective amount of a compound of formula (I) or a stereoisomer, tautomer or pharmaceutically acceptable salt, solvate or prodrug thereof to a patient in need of such treatment.

Another preferred embodiment of the present invention provides for a method of treating or preventing conditions which benefit from maintaining or enhancing levels of bradykinin which comprises administering a therapeutically effective amount of a compound of formula (I) or a stereoisomer, tautomer or pharmaceutically acceptable salt, solvate or prodrug thereof to a patient in need of such treatment.

It is to be appreciated that all references herein to treatment include curative, palliative and prophylactic treatment. The amount of compound administered and the frequency of administration will be determined by the attending physician taking into account the characteristics of the patient, such as age, weight and state of health, and the degree of inhibition of TAFIa desired. The total daily dose for a typical 70 kg adult will generally be between 1 mg and 5 g, preferably between 10 mg and 1 g, more preferably between 50 mg and 750 mg. The total dose may be given as a single or divided dose.

The compounds of the present invention may be used alone or in combination with other therapeutic agents. When used in combination with another therapeutic agent the administration of the two agents may be simultaneous or sequential. Simultaneous administration includes the administration of a single dosage form that comprises both agents and the administration of the two agents in separate dosage forms at substantially the same time. Sequential administration includes the administration of the two agents according to different schedules provided that there is an overlap in the periods during which the treatment is provided. Suitable agents with which the compounds of formula (I) can be co-administered include antithrombotics, including antiplatelet agents, anticoagulants and profibrinolytics. Suitable antithrombotics include: aspirin, Plavix™, ticlopidine, warfarin (Coumadin™), unfractionated heparin, hirudin (Lepirudin™), streptokinase, urokinase, recombinant tissue plasminogen activator (tPA), dipyridamole, Reopro™, Aggrastat™, and Integrilin™. The compounds of formula (I) can also be administered together with antihypertensive agents and with agents to treat dyslipidaemia such as statins eg Lipitor™. Further suitable drug classes for co-administration include Factor X inhibitors and antiarrhythmics such as amiodarone or digoxin. Accordingly, in a further aspect, the present invention provides for the use of a compound of formula (I) or a stereoisomer, tautomer or pharmaceutically acceptable salt, solvate or prodrug thereof in combination with an antithrombotic agent for the preparation of a medicament for the treatment of thrombosis. In a preferred embodiment the antithrombotic is an profibrinolytic. In a more preferred embodiment the antithrombotic is recombinant tissue plasminogen activator (tPA).

In a further aspect, the present invention provides for a method of treating or preventing thrombosis, which comprises administering a therapeutically effective amount of a compound of formula (I) or a stereoisomer, tautomer or pharmaceutically acceptable salt, solvate or prodrug thereof in combination with an antithrombotic to a patient in need of such treatment. In a preferred embodiment the antithrombotic is a profibrinolytic. In a more preferred embodiment the antithrombotic is recombinant tissue plasminogen activator (tPA).

In a further aspect, the present invention provides for a kit comprising:

a) a composition comprising a compound of formula (I) or a stereoisomer, tautomer or pharmaceutically acceptable salt, solvate or prodrug thereof as disclosed herein and a pharmaceutically acceptable diluent or carrier;

b) a composition comprising an antithrombotic and a pharmaceutically acceptable diluent or carrier; and c) a container The components of this kit may be administered separately, simultaneously or sequentially.

The present invention also provides for the use a compound of formula (I) or a stereoisomer, tautomer or pharmaceutically acceptable salt, solvate or prodrug thereof as a coating on intravascular devices such as indwelling catheters for dialysis, replacement heart valves or arterial stents; and as a coating on extra-corporeal blood circulation devices such as heart, lung and kidney dialysis machines, to prevent thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events such as restenosis following intervention surgery such as percutaneous transluminal coronary angioplasty, grafting, stent in-placement, coronary bypass surgery or any other forms of surgical revascularisation or intervention.

The invention provides for intravascular devices, of which the intravascular portion is coated with a compound of formula (I) or a stereoisomer, tautomer or pharmaceutically acceptable salt, solvate or prodrug thereof; and extra corporeal blood circulation devices such as heart, lung and kidney dialysis machines, where the portion coming into contact with the subjects blood is coated with a compound of formula (I) or a stereoisomer, tautomer or pharmaceutically acceptable salt, solvate or prodrug thereof.

The compounds of the present invention are TAFIa inhibitors, whose utility is based upon preventing the reaction between a developing thrombus and TAFIa. It has been found that the compounds of the present invention are also capable of binding to the unactivated TAFI molecule, at the site implicated in the reaction between TAFIa and the developing clot. The use of TAFIa inhibitors as described above in terms of scope and utility, includes such TAFIa inhibitors which bind to TAFI.

The invention is further illustrated by the following, non-limiting examples.

Melting points were determined on a Gallenkamp melting point apparatus using glass capillary tubes and are uncorrected. Unless otherwise indicated all reactions were carried out under a nitrogen atmosphere, using commercially available anhydrous solvents. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40–63 μm silica gel (Merck silica gel 60). Ion exchange chromatography was performed using with the specified ion exchange resin which had been pre-washed with deionised water. Proton NMR spectra were measured on a Varian Inova 300, Varian Inova 400, or Varian Mercury 400 spectrometer in the solvents specified. In the NMR spectra, only non-exchangeable protons which appeared distinct from the solvent peaks are reported. Low resolution mass spectra were recorded on either a Fisons Trio 1000, using thermospray positive ionisation, or a Finnigan Navigator, using electrospray positive or negative ionisation. High resolution mass spectra were recorded on a Bruker Apex II FT-MS using electrospray positive ionisation. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in a suitable solvent.

Abbreviations and Definitions

Arbocel™ Filtration agent, from J. Rettenmaier & Sohne, Germany

Amberlyst® Ion exchange resin, available from Aldrich Chemical Company

15 atm Pressure in atmospheres (1 atm=760 Torr=101.3 kPa)

Biotage™ Chromatography performed using Flash 75 silica gel cartridge, from Biotage, UK BOC tert-Butyloxycarbonyl group br Broad c Concentration used for optical rotation measurements in g per 100 ml (1 mg/ml is c 0.10)

cat Catalytic d Doublet dd Doublet of doublets

Degussa® 10 wt % palladium on activated carbon, Degussa type E101 available from 101 Aldrich Chemical Company Dowex® Ion exchange resin, from Aldrich Chemical Company ee Enantiomeric excess HRMS High Resolution Mass Spectrocopy (electrospray ionisation positive scan)

Hyflo™ Hyflo supercel®, from Aldrich Chemical Company liq liquid

LRMS Low Resolution Mass Spectroscopy (electrospray or thermospray ionisation positive scan)

LRMS ($ES^-$) Low Resolution Mass Spectroscopy (electrospray ionisation negative scan)

m Multiplet m/z Mass spectrum peak

MCI™ gel High porous polymer, CHP20P 75–150 μm, from Mitsubishi Chemical Corporation psi Pounds per square inch (1 psi=6.9 kPa)

q Quartet $R_f$ Retention factor on TLC s Singlet

Sep-Pak® Reverse phase $C_{18}$ silica gel cartridge, Waters Corporation t Triplet TLC Thin Layer Chromatography δ Chemical shift

EXAMPLE 1

(2S)-(−)-2-(2-Aminoethoxy)-3-(1-propyl-1H-imidazol-4-yl)propanoic acid

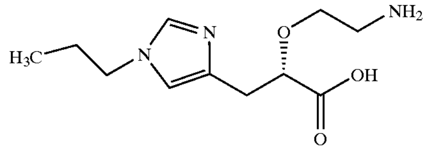

A solution of the compound of Preparation 88 (437 mg, 1.96 mmol) in 6M hydrochloric acid (35 ml) was heated at reflux for 72 hours, then allowed to cool and concentrated under reduced pressure. The residue was dissolved in water (2 ml) and the solution was purified by column chromatography on Dowex® 50WX8-200 ion exchange resin using an elution gradient of water:0.88 ammonia (100:0 to 98:2). The product containing fractions were combined and evaporated under reduced pressure, and the product was freeze-dried to afford the title compound, 456 mg. $^1$H-NMR ($CDCl_3$, 400 MHz) δ: 0.82 (t, 3H), 1.70 (m, 2H), 2.80 (m, 1H), 3.01 (m, 3H), 3.44 (m, 1H), 3.78 (m, 3H), 3.89 (dd, 1H), 6.70 (s, 1H), 7.35 (s, 1H). LRMS: m/z ($ES^+$) 264 [$MNa^+$]. Microanalysis found: C, 49.04; H, 8.17; N, 15.51. $C_{11}H_{19}N_3O_3$; $1.6H_2O$ requires C, 49.04; H, 8.28; N, 15.60%. $[\alpha]_D$=−33.43 (c=0.193, methanol).

EXAMPLES 2 to 4

The following compounds of general formula

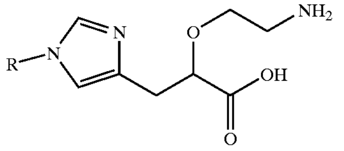

were prepared from the corresponding morpholinone compounds following the procedure of Example 1.

| Ex | R | Yield (%) | Data |
|---|---|---|---|
| 2 | 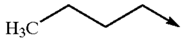 | 37 sticky solid | $^1$H-NMR($D_2O$, 400MHz) δ: 0.76(t, 3H), 1.10(m, 2H), 1.60(m, 2H), 2.75(dd, 1H), 2.82(dd, 1H), 3.00(m, 2H), 3.55(m, 2H), 3.62(t, 2H), 3.90(dd, 1H), 6.83(s, 1H), 7.48(s, 1H). LRMS: m/z(TSP$^+$) 256.2[MH$^+$]. Microanalysis found: C, 53.59; H, 8.35; N, 15.57. $C_{12}H_{21}N_3O_3$; 0.75$H_2O$ requires C, 53.62; H, 8.44; N, 15.63%. |
| 3 | 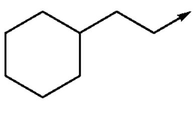 | 48 sticky gum | $^1$H-NMR($D_2O$, 300MHz) δ: 0.82(m, 2H), 1.05(m, 4H), 1.57(m, 7H), 2.77–2.97(m, 2H), 3.05(m, 2H), 3.59(m, 2H), 3.95(m, 3H), 6.94(s, 1H), 7.59(s, 1H). LRMS: m/z(ES$^+$) 310[MH$^+$]. |
| 4 | 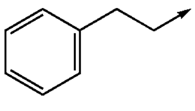 | 61 | $^1$H-NMR($CDCl_3$, 400MHz) δ: 2.80(dd, 1H), 2.99(m, 5H), 3.42(m, 1H), 3.80(m, 1H), 3.92(m, 1H), 4.02(t, 2H), 6.64(s, 1H), 7.01(d, 2H), 7.20(m, 4H). LRMS: m/z(ES$^+$) 304[MH$^+$]. Microanalysis found: C, 58.93; H, 7.17; N, 12.82. $C_{16}H_{21}N_3O_3$; 1.27$H_2O$ requires C, 58.91; H, 7.27; N, 12.88%. |

EXAMPLE 5

(2S)-(−)-2-(2-Aminoethoxy)-3-[1-(2-cyclohexylethyl)-1H-imidazol-4-yl]propanoic acid

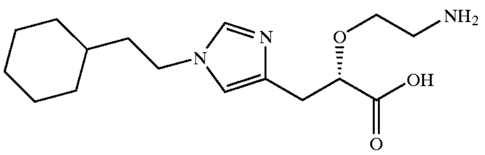

A solution of the compound of Preparation 133 (72 mg, 0.25 mmol) in concentrated hydrochloric acid (5 ml) was heated at 110° C. for 18 hours, then allowed to cool and concentrated under reduced pressure. The residue was dissolved in water and the solution was purified by column chromatography on Dowex® 50WX8-200 ion exchange resin using an elution gradient of water:0.88 ammonia:methanol (95:5:0 to 90:5:5). The product was dissolved in water (5 ml) and freeze-dried to afford the title compound as a sticky gum, 45 mg. $^1$H-NMR ($CD_3OD$, 400 MHz) δ: 0.99 (m, 2H), 1.21 (m, 4H), 1.61–1.78 (m, 7H), 2.86 (dd, 1H), 3.02 (m, 3H), 3.58–3.70 (m, 2H), 3.98 (m, 3H), 6.93 (s, 1H), 7.50 (s, 1H). LRMS: m/z (ES$^+$) 310 [MH$^+$]. Microanalysis found: C, 59.56; H, 8.76; N, 12.91. $C_{16}H_{27}N_3O_3$; 0.75$H_2O$ requires C, 59.51; H, 8.90; N, 13.01%. $[\alpha]_D$=−23.34 (c=0.102, methanol).

EXAMPLE 6

(2S)-(−)-2-(2-Aminoethoxy)-3-(1-phenyl-1H-imidazol-4-yl)propanoic acid

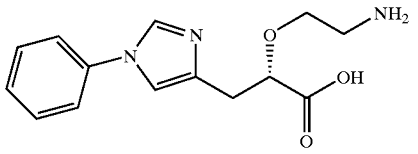

The title compound was obtained as a fawn solid in 87% yield from the morpholinone of Preparation 104, following the procedure of Example 5. $^1$H-NMR ($D_2O$, 400 MHz) 67 : 2.88 (dd, 1H), 3.00 (dd, 1H), 3.10 (t, 2H), 3.62 (t, 2H), 4.02 (m, 1H), 7.30 (s, 1H), 7.39 (m, 1H), 7.45 (m, 4H), 7.98 (s, 1H). LRMS: m/z (ES$^+$) 298 [MNa$^+$]. Microanalysis found: C, 59.15; H, 6.39; N, 14.71. $C_{14}H_{17}N_3O_3$; 0.5$H_2O$ requires C, 59.14; H, 6.38; N, 14.78%. $[\alpha]_D$=−16.8 (c=0.10, methanol).

EXAMPLE 7

(2S)-2-(2-Aminoethoxy)-3-{1-[3,5-bis(trifluoromethyl)phenyl]-1H-imidazol-4-yl}-propanoic acid

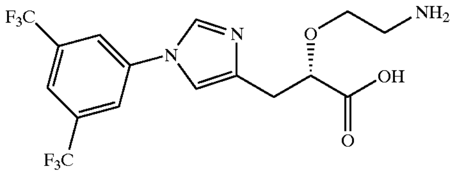

The title compound was obtained as a white solid in 45% yield from the morpholinone of Preparation 106, following the procedure of Example 5. $^1$H-NMR ($CD_3OD$, 400 MHz) δ: 3.00–3.18 (m, 3H), 3.65 (m, 1H), 3.75 (m, 1H), 4.04 (m, 2H), 7.58 (s, 1H), 7.98 (s, 1H), 8.22 (s, 2H), 8.30 (s, 1H). LRMS: m/z (ES$^-$) 410 [M−H]. Microanalysis found: C, 43.95; H, 3.79; N, 9.99. $C_{16}H_{15}F_6N_3O_3$; 1.25$H_2O$ requires C, 44.30; H, 4.07; N, 9.69%.

EXAMPLE 8

(2RS)-2-[(2-(Methylamino)ethoxy]-3-(1-propyl-1H-imidazol-4-yl)propanoic acid

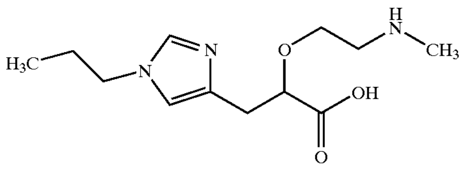

The title compound was obtained from the morpholinone of Preparation 51, following the procedure of Example 1. $^1$H-NMR ($D_2O$, 400 MHz) δ: 0.70 (t, 3H), 1.62 (m, 2H), 2.56 (s, 3H), 2.76 (dd, 1H), 2.84 (dd, 1H), 3.05 (m, 2H), 3.53–3.63 (m, 2H), 3.80 (t, 2H), 3.94 (dd, 1H), 6.84 (s, 1H), 7.50 (s, 1H). LRMS: m/z (TSP$^+$) 256.2 [MH$^+$].

EXAMPLE 9

(2RS)-2-[(2-(Dimethylamino)ethoxy]-3-(1-propyl-1H-imidazol-4-yl)propanoic acid

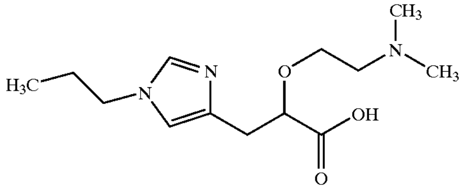

A solution of the protected acid of Preparation 142 (200 mg, 0.62 mmol) in trifluoroacetic acid (5 ml) and dichloromethane (5 ml) was stirred at room temperature for 18 hours, then concentrated under reduced pressure. The residue was dissolved in water and the solution was purified by column chromatography on Dowex® 50WX8-200 ion exchange resin using water:0.88 ammonia (96:4) as eluant. The product containing fractions were concentrated under reduced pressure and the residue was dissolved in water and freeze-dried to afford the title compound as a sticky gum, 100 mg. $^1$H-NMR ($D_2O$, 400 MHz) δ: 0.66 (t, 3H), 1.60 (m, 2H), 2.60–2.78 (m, 7H), 2.82 (dd, 1H), 3.14 (m, 2H), 3.57 (m, 1H), 3.61 (m, 1H), 3.78 (t, 2H), 3.92 (m, 1H), 6.82 (s, 1H), 7.48 (s, 1H). LRMS: m/z ($TSP^+$) 270.2 [$MH^+$]. Microanalysis found: C, 54.41; H, 8.72; N, 14.58. $C_{13}H_{23}N_3O_3$;$H_2O$ requires C, 54.34; H, 8.77; N, 14.62%.

EXAMPLE 10

(2RS)-3-(1-Propyl-1H-imidazol-4-yl )-2-[(3R)-pyrrolidin-3-yloxy]propanoic acid

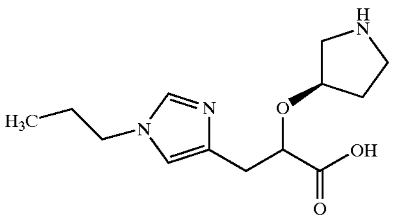

Concentrated hydrochloric acid (3 ml) was added to a solution of the protected amino acid of Preparation 143 (232 mg, 0.55 mmol) in dioxan (2 ml), and the mixture was stirred at room temperature for 18 hours, then concentrated under reduced pressure. The residue was dissolved in water (1 ml) and the solution was purified by column chromatography on Dowex® 50WX8-200 ion exchange resin using an elution gradient of water:0.88 ammonia (100:0 to 98:2). The product was freeze-dried to afford the title compound as a white solid, 67 mg. $^1$H-NMR ($D_2O$, 400 MHz) (mixture of diastereoisomers) δ: 0.72 (m, 3H), 1.63 (m, 2H), 1.80, 1.98, 2.08 (3×m, 2H), 2.65, 2.84 (2×m, 3H), 3.03–3.38 (m, 3H), 3.81 (m, 2H), 3.94 (m, 1H), 4.14 (m, 1H), 6.89 (m, 1H), 7.53 (m, 1H). LRMS: m/z ($ES^+$) 290 [$MNa^+$].

EXAMPLE 11

(2RS)-2-(2-Aminoethoxy)-3-{1-[2-(4'-ethyl[1,1'-biphenyl]-4-yl)ethyl]-1H-imidazol-4-yl}-propanoic acid

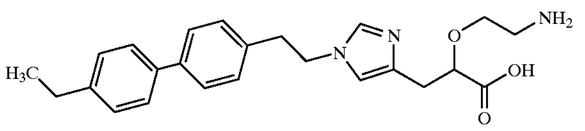

A mixture of the compound of Preparation 121 (170 mg, 0.43 mmol) and concentrated hydrochloric acid (2 ml) was heated at 110° C. for 18 hours, then allowed to cool and concentrated under reduced pressure. The residue was azeotroped with ethanol, methanol and dichloromethane, then purified by column chromatography on Dowex® 50WX8-200 ion exchange resin using an elution gradient of water:0.88 ammonia (100:0 to 98:2) to afford the title compound, 15 mg. $^1$H-NMR ($CD_3OD$, 400 MHz) δ: 1.22 (t, 3H), 2.62 (q, 2H), 2.82 (m, 1H), 2.98 (m, 3H), 3.02 (t, 2H), 3.50–3.62 (m, 2H), 3.90 (m, 1H), 4.18 (t, 2H), 6.86 (s, 1H), 7.14 (d, 2H), 7.20 (d, 2H), 7.30 (s, 1H), 7.43 (m, 4H). Microanalysis found: C, 64.05; H, 6.99; N, 9.35. $C_{25}H_{29}N_3O_3$; 2.7$H_2O$ requires C, 64.28; H, 7.21; N, 8.99%.

EXAMPLES 12 to 14

The following compounds of general formula

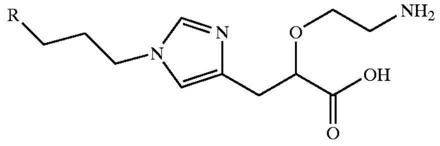

were prepared from the corresponding morpholinones following the procedure of Example 11.

| Ex | R | Yield (%) | Data |
|---|---|---|---|
| 12 | 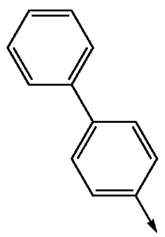 | 35 white solid | $^1$H-NMR($CD_3OD$, 400MHz) δ: 2.15(m, 2H), 2.62(t, 2H), 2.90(dd, 1H), 3.02(m, 3H), 3.60(m, 1H), 3.66(m, 1H), 3.98(m, 3H), 6.96(s, 1H), 7.25(m, 3H), 7.40(m, 2H), 7.54(m, 3H), 7.58(d, 2H). LRMS: m/z($ES^-$) 392[M - $H^-$]. |
| 13 | 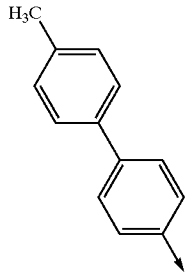 | 17 white foam | $^1$H-NMR($CD_3OD$, 400MHz) δ: 2.09(m, 2H), 2.34(s, 3H), 2.59(m, 2H), 2.86(m, 1H), 3.00(m, 3H), 3.60(m, 2H), 3.97(m, 3H), 6.96(s, 1H), 7.19(m, 4H), 7.40–7.60(m, 5H). LRMS: m/z($ES^+$) 430[$MNa^+$]. |
| 14 | 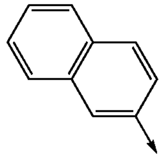 | 21 yellow solid | $^1$H-NMR($CD_3OD$, 400MHz) δ: 2.18(m, 2H), 2.78(t, 2H), 2.88(dd, 1H), 3.02(m, 3H), 3.58–3.72(m, 2H), 3.97(m, 3H), 6.95(s, 1H), 7.40(m, 2H), 7.50(s, 1H), 7.60(s, 1H), 7.78(m, 3H). LRMS: m/z($ES^-$) 366[M - $H^-$]. |

EXAMPLE 15

(2S)-2-{[(1R)-2-Amino-1-methylethyl]oxy}-3-[1-(2-cyclohexylethyl)-1H-imidazol-4-yl]-propanoic acid

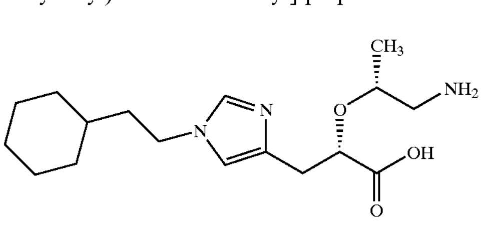

The title compound was obtained in 45% yield from the morpholinone of Preparation 92, following the procedure of Example 11. $^1$H-NMR ($CD_3OD$, 400 MHz) δ: 0.94 (m, 4H), 1.18 (m, 4H), 1.59–1.76 (m, 7H), 2.72 (m, 2H), 2.96 (m, 1H), 3.03 (m, 1H), 3.26 (m, 1H), 3.55 (m, 1H), 3.98 (m, 3H), 6.88 (s, 1H), 7.48 (s, 1H). LRMS: m/z ($ES^+$) 324 [$MNa^+$]. Microanalysis found: C, 58.97; H, 9.01; N, 11.85. $C_{17}H_{29}N_3O_3$; 1.2$H_2O$ requires C, 59.18; H, 9.17; N, 12.18%.

EXAMPLE 16

(2RS)-2-(2-Aminoethoxy)-3-(1-phenyl-1H-imidazol-4-yl) propanoic acid

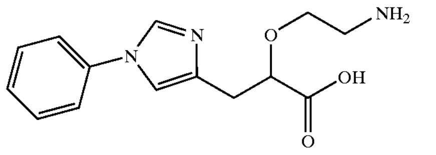

A solution of the compound of Preparation 99 (70 mg, 0.27 mmol) in concentrated hydrochloric acid (2 ml) was heated at 110° C. for 18 hours, then allowed to cool and concentrated under reduced pressure. The residue was azeotroped with water, then purified by column chromatography on Dowex® 50WX8-200 ion exchange resin using water:0.88 ammonia (95:5) as eluant to afford the title compound as a pale yellow solid, 50 mg. $^1$H-NMR ($CD_3OD$, 400MHz) δ: 2.93–3.14 (m, 3H), 3.24 (m, 1H), 3.59–3.73 (m, 2H), 4.00 (m, 1H), 7.35 (m, 2H), 7.45 (m, 4H), 7.98 (s, 1H). LRMS: m/z ($ES^+$) 298 [$MNa^+$].

EXAMPLE 17

(2S)-2-{[(1R)-2-Amino-1-methylethyl]oxy}-3-(1-phenyl-1H-imidazol-4-yl)propanoic acid

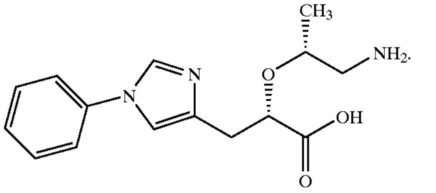

The title compound was obtained in 75% yield from the morpholinone of Preparation 109, following the procedure of Example 16, except that an elution gradient of methanol: water:0.88 ammonia (20:80:5 to 30:65:5) was used for the ion exchange chromatography. $^1$H-NMR ($D_2O$, 400 MHz) δ: 0.90 (d, 3H), 2.80 (m, 2H), 3.00 (m, 2H), 3.59 (m, 1H), 4.14 (dd, 1H), 7.26 (s, 1H), 7.37 (m, 1H), 7.42 (m, 4H), 7.96 (s, 1H). LRMS: m/z ($ES^-$) 288 [M−H]. Microanalysis found: C, 58.76; H, 6.72; N, 13.37. $C_{15}H_{19}N_3O_3$;$H_2O$ requires C, 58.63; H, 6.89; N, 13.67%. $[\alpha]_D$=−83.0 (c=0.1, methanol).

EXAMPLE 18

(2S)-2-{[(1R)-2-Amino-1-methylethyl]oxy}-3-[1-(3',4'-dichloro[1,1'-biphenyl]-3-yl)-1H-imidazol-4-yl)propanoic acid

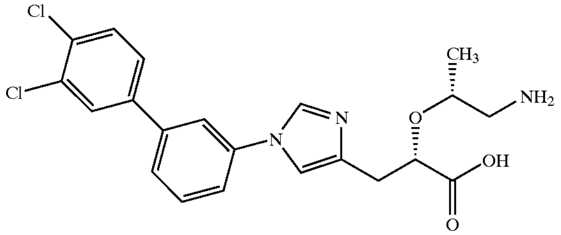

The title compound was obtained as a white foam from the morpholinone of Preparation 115, following the procedure of Example 17, except that an elution gradient of water:methanol:0.88 ammonia (75:20:5 to 15:80:5) was used for the ion exchange chromatography. $^1$H-NMR ($CD_3OD$, 400 MHz) δ: 1.00 (d, 3H), 2.77 (dd, 1H), 2.92 (m, 2H), 3.15 (dd, 1H), 3.59 (m, 1H), 4.10 (m, 1H), 7.42 (s, 1H), 7.50–7.627 (m, 5H), 7.78 (s, 1H), 7.86 (s, 1H), 8.10 (s, 1H). LRMS: m/z ($ES^+$) 434, 436 [$MH^+$].

EXAMPLE 19

(2S)-2-{[(1R)-2-Amino-1-methylethyl]oxy}-3-[1-(4-phenoxyphenyl)-1H-imidazol-4-yl]-propanoic acid

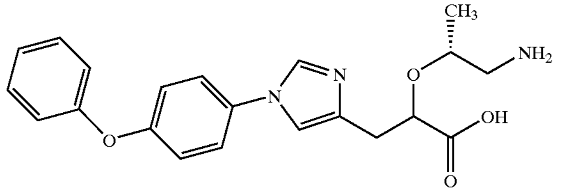

A solution of the morpholinone of Preparation 111 (130 mg, 0.36 mmol) in concentrated hydrochloric acid (10 ml) was heated at 110° C. for 18 hours, then allowed to cool and concentrated under reduced pressure. The residue was purified by column chromatography on Dowex® 50WX8-200 ion exchange resin using water:methanol:0.88 ammonia (70:30:5) as eluant. The product was dissolved in water and freeze-dried to afford the title compound as an off-white powder, 70 mg. $^1$H-NMR ($CD_3OD$, 400 MHz) δ: 1.00 (d, 3H), 2.78 (dd, 1H), 2.86–3.00 (m, 2H), 3.17 (dd, 1H), 3.60 (m, 1H), 4.15 (dd, 1H), 7.02 (d, 2H), 7.08 (d, 2H), 7.17 (m, 1H), 7.30 (s, 1H), 7.39 (m, 2H), 7.50 (d, 2H), 7.95 (s, 1H). LRMS: m/z ($ES^+$) 404 [$MNa^+$]. Microanalysis found: C, 62.70; H, 6.22; N, 10.30. $C_{21}H_{23}N_3O_4$; 1.2$H_2O$ requires C, 62.58; H, 6.35; N, 10.43%. $[\alpha]_D$=−50.9 (c=0.117, methanol).

EXAMPLES 20 to 31

The following compounds of general formula

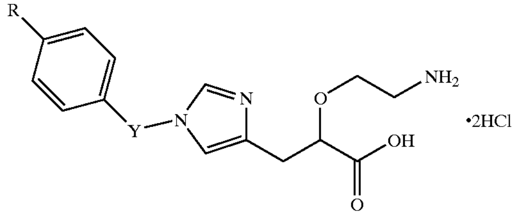

were prepared by heating a solution of the corresponding morpholinone (0.2 to 0.4 mmol) in concentrated hydrochloric acid (2 ml) at reflux for 18 hours, concentrating the cooled solution, and azeotroping the residue with ethanol, ethyl acetate and dichloromethane.

| Ex | R | Y | Data |
|---|---|---|---|
| 20 | 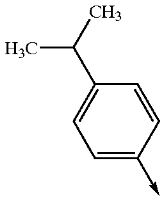 | —$(CH_2)_2$— | $^1$H-NMR($CD_3OD$, 400MHz) δ: 1.22(d, 6H), 2.90(m, 1H), 3.10–3.22(m, 6H), 3.78(m, 2H), 4.36(m, 1H), 4.45(t, 2H), 7.18(d, 2H), 7.24(d, 2H), 7.44(m, 3H), 7.52(d, 2H), 8.62(s, 1H). Microanalysis found: C, 56.65; H, 7.03; N, 7.92. $C_{25}H_{31}N_3O_4$; 2HCl; $2H_2O$ requires C, 56.60; H, 7.03; N, 7.92%. |
| 21 | 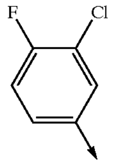 | —$(CH_2)_2$— | $^1$H-NMR($CD_3OD$, 400MHz) δ: 3.18(m, 5H), 3.78(m, 3H), 4.15–4.38(m, 1H), 4.44(m, 2H), 7.21(m, 3H), 7.50(m, 4H), 7.63(m, 1H), 8.58–8.65(m, 1H). LRMS: m/z($ES^+$) 432, 434 [$MH^+$]. |
| 22 | 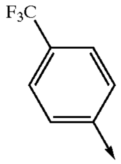 | —$(CH_2)_2$— | $^1$H-NMR($CD_3OD$, 400MHz) δ: 3.10–3.30(m, 4H), 3.78(m, 4H), 4.30(m, 1H), 4.46(m, 2H), 7.24(m, 2H), 7.50(m, 1H), 7.60(m, 2H), 7.74 (m, 4H), 8.62(m, 1H). Microanalysis found: C, 50.27; H, 5.39; N, 7.34. $C_{23}H_{24}F_3N_3O_3$; 2HCl; $1.7H_2O$ requires C, 50.14; H, 5.38; N, 7.63%. |
| 23 | 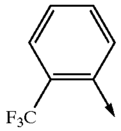 | —$(CH_2)_2$— | $^1$H-NMR($CD_3OD$, 400MHz) δ: 3.18(m, 3H), 3.21(m, 2H), 3.76(m, 0.5H), 3.80(m, 2H), 4.20 (m, 0.5H), 4.32(m, 1H), 4.48(m, 2H), 7.20(m, 4H), 7.30(d, 1H), 7.50(m, 2H), 7.60(m, 1H), 7.76(m, 1H), 8.60(m, 1H). HRMS: m/z($ES^+$) 448.1842[$MH^+$]. |
| 24 | 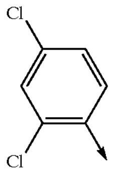 | —$(CH_2)_2$— | $^1$H-NMR($CD_3OD$, 400MHz) δ: 3.18(m, 2H), 3.20(m, 2H), 3.74(m, 1H), 3.80(m, 2H), 4.20 (m, 1H), 4.35(m, 1H), 4.48(t, 2H), 7.21(m, 2H), 7.26–7.40(m, 4H), 7.48(m, 1H), 7.52(m, 1H), 8.59–8.65(m, 1H). Microanalysis found: C, 50.18; H, 5.15; N, 7.32. $C_{22}H_{23}Cl_2N_3O_3$; 2HCl; $H_2O$ requires C, 50.02; H, 5.11; N, 7.61%. |
| 25 | 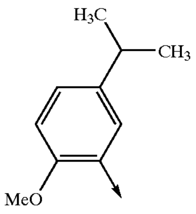 | —$(CH_2)_2$— | $^1$H-NMR($CD_3OD$, 400MHz) δ: 1.20(m, 6H), 2.81(m, 1H), 3.17(m, 6H), 3.70(m, 2H), 3.78 (m, 2H), 4.18(m, 1H), 4.30(m, 1H), 4.46(m, 2H), 6.78–7.16(m, 5H), 7.39(d, 1H), 7.44(m, 2H), 8.60(m, 1H). |
| 26 | 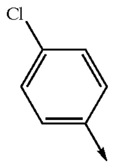 | —$(CH_2)_2$— | $^1$H-NMR($CD_3OD$, 400MHz) δ: 3.17(m, 4H), 3.78(m, 3H), 4.18(m, 1H), 4.30(m, 1H), 4.45 (m, 2H), 7.20(m, 2H), 7.40(m, 2H), 7.56(m, 5H), 8.61(m, 1H). Microanalysis found: C, 52.64; H, 5.82; N, 7.91. $C_{22}H_{24}ClN_3O_3$; 2HCl; $H_2O$ requires C, 52.34; H, 5.59; N, 8.32%. |
| 27 | 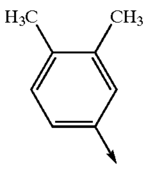 | —$(CH_2)_2$— | $^1$H-NMR($CD_3OD$, 400MHz) δ: 2.24(d, 6H), 3.07–3.22(m, 5H), 3.77(m, 3H), 4.30(m, 1H), 4.42(m, 2H), 7.23(d, 1H), 7.30(s, 1H), 7.45 (m, 3H), 8.60(2xs, 1H). Microanalysis found: C, 57.44; H, 6.74; N, 8.02. $C_{24}H_{29}N_3O_3$; 2HCl;-$1.3H_2O$ requires C, 57.21; H, 6.72; N, 8.34%. |

-continued

| Ex | R | Y | Data |
| --- | --- | --- | --- |
| 28 | 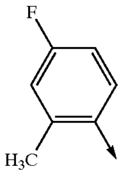 | $—(CH_2)_2—$ | $^1$H-NMR($CD_3OD$, 400MHz) δ: 3.12–3.23(m, 8H), 3.75(m, 1H), 3.80(m, 2H), 4.32(m, 1H), 4.45(m, 2H), 6.90(m, 1H), 6.99(m, 1H), 7.10 (m, 1H), 7.19(m, 4H), 7.50(s, 1H), 8.61(m, 1H). Microanalysis found: C, 54.72; H, 6.14; N, 7.96. $C_{23}H_{26}FN_3O_3$; 2HCl; $1.2H_2O$ requires C, 54.59; H, 6.06; N, 8.30%. |
| 29 | 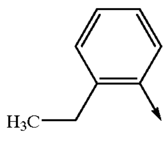 | $—(CH_2)_2—$ | $^1$H-NMR($CD_3OD$, 400MHz) δ: 1.00(t, 3H), 2.56 (q, 2H), 3.19(m, 5H), 3.80(m, 2H), 4.19(m, 1H), 4.30(m, 1H), 4.46(m, 2H), 7.04(d, 1H), 7.19(m, 7H), 7.50(m, 1H), 8.62(2xs, 1H) |
| 30 | 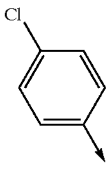 | $—(CH_2)_3—$ | $^1$H-NMR($CD_3OD$, 400MHz) δ: 2.23(m, 2H), 2.70(t, 2H), 3.17(m, 3H), 3.21(m, 1H), 3.80(t, 2H), 4.22(m, 2H), 4.30(m, 1H), 7.25(m, 2H), 7.40(d, 2H), 7.48–7.64(m, 5H0, 8.62(m, 1H). Microanalysis found: C, 51.77; H, 5.72; N, 7.61. $C_{23}H_{26}ClN_3O_3$; 2HCl; $2H_2O$ requires C, 51.46; H, 6.01; N, 7.83%. |
| 31 | 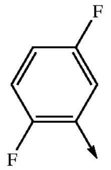 | $—(CH_2)_3—$ | $^1$H-NMR($CD_3OD$, 400MHz) δ: 2.23(m, 2H), 2.74(m, 2H), 3.17(m, 4H), 3.80(m, 2H), 4.22 (m, 3H), 7.05(m, 1H), 7.18(m, 2H), 7.29(m, 2H), 7.44(m, 2H), 7.58–7.70(m, 1H), 8.82(s, 1H). Microanalysis found: C, 50.15; H, 5.38; N, 7.39. $C_{23}H_{25}F_2N_3O_3$; 2HCl; $2.5H_2O$ requires C, 50.46; H, 5.89; N, 7.68%. |

EXAMPLE 32

(2RS)-2-(2-Aminoethoxy)-3-[1-(3-[1,1'-biphenyl]-3-ylpropyl)-1H-imidazol-4-yl]-propanoic acid dihydrochloride

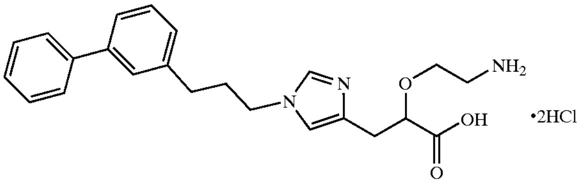

•2HCl

The title compound was obtained as an off-white foam from the compound of Preparation 145, following the procedure of Example 20. $^1$H-NMR ($CD_3OD$, 400 MHz) δ: 2.25 (m, 2H), 2.75 (m, 2H), 3.14 (m, 2H), 3.27 (m, 1H), 3.74 (m, 1H), 3.78 (m, 2H), 4.22 (m, 3H), 7.18 (m, 1H), 7.25–7.42 (m, 6H), 7.45 (s, 1H), 7.58 (d, 2H), 8.80 (s, 1H). LRMS: m/z ($ES^+$) 394 [$MH^+$]. Microanalysis found: C, 54.03; H, 6.73; N, 8.09. $C_{23}H_{27}N_3O_3$; 2HCl; $2.4H_2O$ requires C, 54.21; H, 6.68; N, 8.24%.

EXAMPLE 33

(2RS)-2-(2-Aminoethoxy)-3-[1-(3-[1,1'-biphenyl]-2-ylpropyl)-1H-imidazol-4-yl]-propanoic acid dihydrochloride

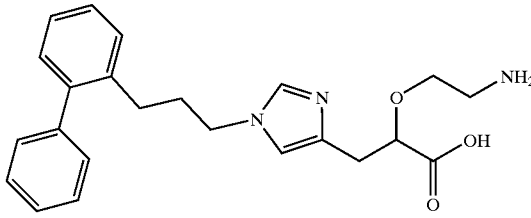

•2HCl

The title compound was obtained as an off-white foam in 30% yield from the compound of Preparation 146, following the procedure of Example 20. $^1$H-NMR ($CD_3OD$, 400 MHz) δ: 1.96 (m, 2H), 2.60 (t, 2H), 3.05–3.23 (m, 4H), 3.79 (m, 2H), 4.02 (t, 2H), 4.48 (m, 1H), 7.14 (d, 1H), 7.19–7.30 (m, 6H), 7.36 (m, 3H), 8.62 (s, 1H). Microanalysis found: C, 54.89; H, 6.24; N, 8.35. $C_{23}H_{27}N_3O_3$; 2HCl; $2H_2O$ requires C, 54.98; H, 6.62; N, 8.36%.

EXAMPLE 34

(2S)-2-{[(2S)-Aminopropyl]oxy}-3-[1-(2-cyclohexylethyl)-1H-imidazol-4-yl]propanoic acid dihydrochloride

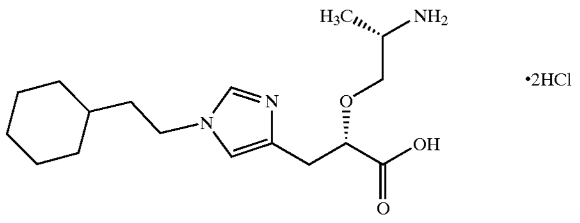

The title compound was obtained in 64% yield from the morpholinone of Preparation 95, following the procedure of Example 20. $^1$H-NMR ($CD_3OD$, 400 MHz) δ: 0.80–1.32 (m, 9H), 1.60–1.80 (m, 7H), 3.20 (m, 1H), 3.57 (m, 3H), 3.80 (m, 1H), 4.20 (m, 2H), 4.35 (m, 1H), 7.48 (s, 1H), 8.86 (s, 1H). HRMS: m/z (ESI) 324.2280 [$MH^+$].

EXAMPLE 35

(2R)-2-{[(2R)-Aminopropyl]oxy}-3-[1-(2-cyclohexylethyl)-1H-imidazol-4-yl]propanoic acid dihydrochloride

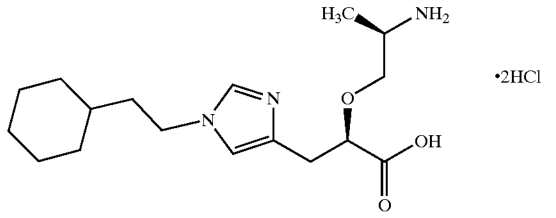

The title compound was obtained from the morpholinone of Preparation 96, following the procedure of Example 20. $^1$H-NMR ($CD_3OD$, 400 MHz) δ: 0.80–1.32 (m, 9H), 1.60–1.80 (m, 7H), 3.20 (m, 1H), 3.57 (m, 3H), 3.80 (m, 1H), 4.20 (m, 2H), 4.35 (m, 1H), 7.48 (s, 1H), 8.86 (s, 1H). HRMS: m/z (ESI) 324.2275 [$MH^+$].

EXAMPLE 36

(2RS)-2-(2-Aminoethoxy)-3-[1-(2-methylphenyl)-1H-imidazol-4-yl]propanoic acid dihydrochloride

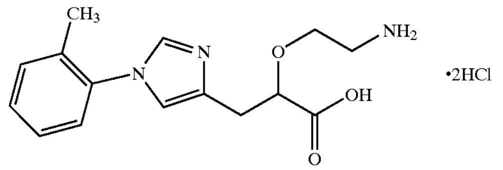

A solution of the morpholinone of Preparation 100 (100 mg, 0.37 mmol) in concentrated hydrochloric acid (2 ml) was heated at 110° C. for 36 hours, then cooled and concentrated under reduced pressure. The residue was azeotroped with methanol and dichloromethane to afford the title compound. $^1$H-NMR ($CD_3OD$, 400 MHz) δ: 2.10 (s, 3H), 3.19 (m, 2H), 3.26 (m, 1H), 3.39 (m, 1H), 3.82 (t, 2H), 4.42 (m, 1H), 7.40 (m, 2H), 7.46 (m, 2H), 7.62 (s, 1H), 9.14 (s,1H). HRMS: m/z 290.1502 [$MH^+$].

EXAMPLE 37

(2R)-2-{[(1S)-2-Amino-1-methylethyl]oxy}-3-[1-(2-cyclohexylethyl)-1H-imidazol-4-yl]-propanoic acid dihydrochloride

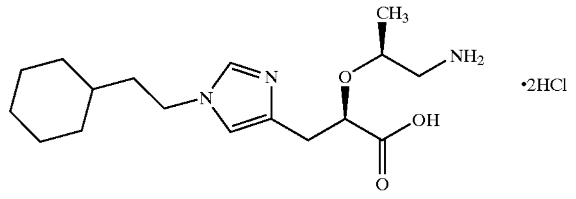

The title compound was obtained from the morpholinone of Preparation 91, following the procedure of Example 20. $^1$H-NMR ($CD_3OD$, 400 MHz) δ: 1.01 (m, 5H), 1.21 (m, 4H), 1.74 (m, 7H), 2.93–3.14 (m, 3H), 3.25 (m, 1H), 3.79 (m, 1H), 4.21 (t, 2H), 4.38 (m, 1H), 7.55 (s, 1H), 8.90 (s, 1H). LRMS: m/z ($ES^-$) 322 [M–H]. Microanalysis found: C, 47.73; H, 7.85; N, 9.66. $C_{17}H_{29}N_3O_3$; 2HCl; $1.6H_2O$ requires C, 48.02; H, 8.11; N, 9.88%.

EXAMPLE 38

(2S)-2-{[(1R)-2-Amino-1-methylethyl]oxy}-3-{1-[2-(4,4-dimethylcyclohexyl)ethyl]-1H-imidazol-4-yl}propanoic acid dihydrochloride

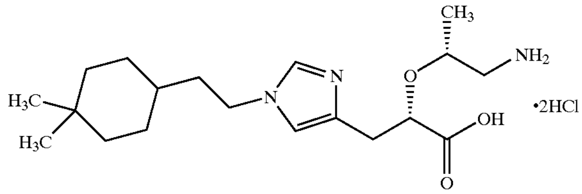

The title compound was obtained in 83% yield from the morpholinone of Preparation 93, following the procedure of Example 20. $^1$H-NMR ($CD_3OD$, 400 MHz) δ: 0.88 (s, 6H), 1.04 (d, 3H), 1.17–1.34 (m, 5H), 1.40 (m, 2H), 1.60 (m, 2H), 2.97–3.18 (m, 3H), 3.30 (m, 1H), 3.81 (m, 1H), 4.24 (m, 2H), 4.40 (m, 1H), 7.58 (s, 1H), 8.94 (s, 1H). HRMS: m/z ($ES^+$) 374.2484 [$MNa^+$].

EXAMPLE 39

(2S)-2-{[(1R)-2-Amino-1-methylethyl]oxy}-3-[1-(3-cyclohexyl-3-methylbutyl)-1H-imidazol-4-yl]propanoic acid dihydrochloride

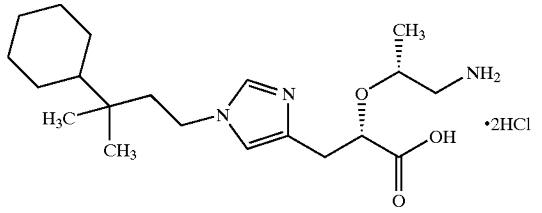

The title compound was obtained from the morpholinone of Preparation 94, following the procedure of Example 20. $^1$H-NMR ($CD_3OD$, 400 MHz) δ: 0.94 (s, 6H), 0.98–1.30 (m, 10H), 1.62 (m, 1H), 1.78 (m, 6H), 2.90–3.15 (m, 3H), 3.78 (m, 1H), 4.20 (m, 2H), 4.38 (m, 1H), 7.52 (s, 1H), 8.90 (s, 1H). LRMS: m/z ($ES^+$) 366 [$MH^+$].

EXAMPLE 40

2-(2-Aminoethoxy)-3-[1-(3-phenoxyphenyl)-1H-imidazol-4-yl]propanoic acid dihydrochloride

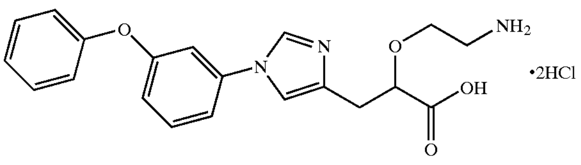

A solution of the morpholinone of Preparation 102 (25 mg, 0.07 mmol) in concentrated hydrochloric acid (5 ml) was heated at 110° C. for 18 hours, then cooled and concentrated under reduced pressure. The residue was dissolved in water and freeze-dried to afford the title compound as a fawn solid, 35 mg. $^{1}$H-NMR ($D_2O$, 400 MHz) δ: 3.04 (m, 3H), 3.18 (dd, 1H), 3.63 (t, 2H), 4.19 (m, 1H), 6.98 (d, 2H), 7.06 (m, 3H), 7.19 (d, 1H), 7.46 (dd, 2H), 7.50 (dd, 1H), 7.54 (s, 1H), 8.87 (s, 1H). LRMS: m/z ($ES^+$) 368 [$MH^+$].

EXAMPLES 41 to 44

The following compounds of general formula

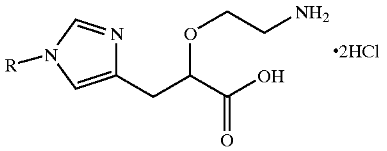

were prepared from the corresponding morpholinones following the procedure of Example 40

| Ex | R | Data |
|---|---|---|
| 41 | 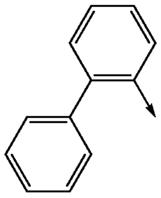 | $^{1}$H-NMR($D_2O$, 400MHz) δ: 3.01–3.20(m, 4H), 3.65(m, 2H), 4.21(m, 1H), 7.10(m, 2H), 7.25(s, 1H), 7.32(m, 3H), 7.54(m, 3H), 7.61(m, 1H), 8.59(s, 1H). LRMS: m/z($ES^+$) 352[$MH^+$]; 374[$MNa^+$]. |
| 42 | 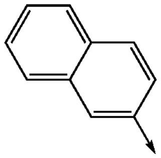 | $^{1}$H-NMR($D_2O$, 400MHz) δ: 3.18–3.35(m, 4H), 3.80(t, 2H), 4.30(dd, 1H), 7.60(m, 3H), 7.77(s, 1H), 7.98(m, 2H), 8.04(m, 2H), 9.06(s, 1H). LRMS: m/z($ES^+$) 348[$MNa^+$]. Microanalysis found: C, 49.16; H, 5.60; N, 9.54. $C_{18}H_{19}N_3O_3$; 2HCl; $2.3H_2O$ requires C, 49.18; H, 5.65; N, 9.58%. |
| 43 | 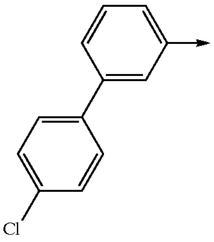 | $^{1}$H-NMR($D_2O$, 400MHz) δ: 3.17–3.35(m, 4H), 3.79(m, 2H), 4.30(m, 1H), 7.40(m, 2H), 7.52(m, 2H), 7.60(m, 2H), 7.70(m, 3H), 9.02(s, 1H). LRMS: m/z($ES^+$) 386[$MH^+$]. |

-continued

| Ex | R | Data |
|---|---|---|
| 44 | 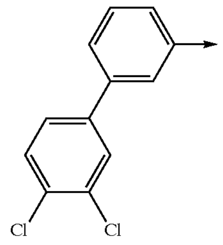 | $^{1}$H-NMR($D_2O$, 400MHz) δ: 3.20–3.35(m, 4H), 3.80(m, 2H), 4.30(t, 1H), 7.42–7.75(m, 8H), 9.05(s, 1H). LRMS: m/z($ES^+$) 420, 422[$MH^+$]. |

EXAMPLE 45

(2S)-(−)-2-(2-Aminoethoxy)-3-[1-(4-tert-butylphenyl)-1H-imidazol-4-yl]propanoic acid dihydrochloride

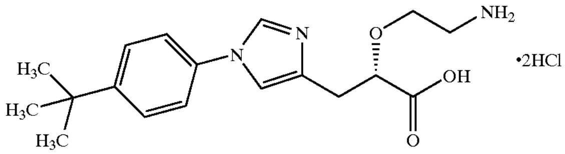

The title compound was obtained as a fawn solid from the morpholinone of Preparation 105, following the procedure of Example 40. $^{1}$H-NMR ($D_2O$, 400 MHz) δ: 1.20 (s, 9H), 3.04–3.35 (m, 4H), 3.78 (m, 2H), 4.38 (m, 1H), 7.41 (m, 2H), 7.58 (m, 2H), 7.61 (s, 1H), 8.98 (s, 1H). LRMS: m/z ($ES^+$) 332 [$MH^+$]. Microanalysis found: C, 49.58; H, 6.75; N, 9.84. $C_{18}H_{25}N_3O_3$; 2HCl; $1.75H_2O$ requires C, 49.58; H, 7.06; N, 9.64%. $[\alpha]_D$=−2.00 (c=0.30, methanol).

EXAMPLES 46 to 48

The following compounds of general formula

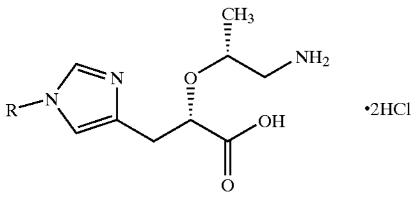

were prepared from the corresponding morpholinones following the procedure of Example 40

| Ex | R | Data |
|---|---|---|
| 46 | 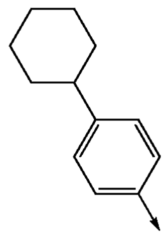 | $^{1}$H-NMR($D_2O$, 400MHz) δ: 1.00(d, 3H), 1.16–1.42(m, 6H), 1.64(m, 1H), 1.78(m, 3H), 2.59(m, 1H), 2.89–3.17(m, 4H), 3.68(m, 1H), 4.30(m, 1H), 7.44(m, 4H), 7.66(s, 1H), 8.98(s, 1H). LRMS: m/z ($ES^+$) 372[$MH^+$]. Microanalysis found: C, 52.74; H, 7.27; N, 8.54. $C_{21}H_{29}N_3O_3$; 2HCl; $2H_2O$ requires C, 52.50; H, 7.34; N, 8.75%. |

-continued

| Ex | R | Data |
| --- | --- | --- |
| 47 | 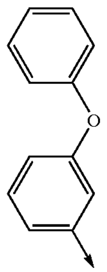 | $^1$H-NMR($D_2O$, 400MHz) δ: 0.98(d, 3H), 2.90(m, 1H), 3.05(m, 2H), 3.24(m, 1H), 3.78(m, 1H), 4.38(m, 1H), 7.02(d, 2H), 7.15(m, 3H), 7.26(d, 1H), 7.38(m, 2H), 7.48(m, 1H), 7.62(s, 1H), 8.99(s, 1H). LRMS: m/z ($ES^+$) 382[$MH^+$]. $[\alpha]_D$ = −72.0(c = 0.05, methanol) |
| 48 | 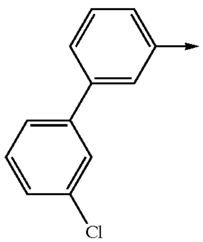 | $^1$H-NMR($D_2O$, 400MHz) δ: 1.01(d, 3H0, 2.98(m, 1H), 3.15(m, 2H), 3.29(m, 1H), 3.79(m, 1H), 4.37(m, 1H), 7.40(m, 2H), 7.58(d, 2H), 7.62(m, 2H), 7.75(m, 3H), 9.05(s, 1H). LRMS: m/z($TSP^+$) 400.2[$MH^+$]. Microanalysis found: C, 47.90; H, 5.48; N, 7.90. $C_{21}H_{22}ClN_3O_3$; 2HCl; $3H_2O$ requires C, 47.88; H, 5.74; N, 7.98%. |

EXAMPLE 49

(2S)-2-{[(1R)-2-Amino-1-methylethyl]oxy}-3-{1-[4-(cyclohexyloxy)phenyl]-1H-imidazol-4-yl}propanoic acid

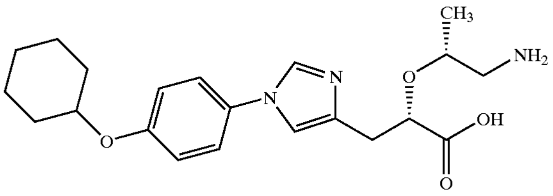

A solution of the protected amino acid of Preparation 120 in a mixture of 2N hydrochloric acid (1 ml), water (1 ml) and dioxan (1 ml) was stirred at room temperature for 2 hours, then concentrated under reduced pressure. The residue was dissolved in water and purified by column chromatography on Dowex® 50WX8-200 ion exchange resin using water: methanol:0.88 ammonia (48:48:4) as eluant. The product was dissolved in water and freeze-dried to afford the title compound, 25 mg. $^1$H-NMR ($D_2O$, 400 MHz) δ: 0.94 (d, 3H), 1.35 (m, 4H), 1.55 (m, 3H), 1.72–2.01 (m, 3H), 2.78–2.97 (m, 2H), 3.10 (m, 2H), 3.60 (m, 1H), 4.01 (m, 1H), 4.21 (m, 1H), 6.92 (d, 2H), 7.01 (s, 1H), 7.20 (d, 2H), 7.62 (s, 1H). LRMS: m/z ($ES^+$) 388 [$MH^+$]. Microanalysis found: C, 59.33; H, 7.65; N, 9.80. $C_{21}H_{29}N_3O_4$; $2H_2O$ requires C, 59.56; H, 7.85; N, 9.92%.

EXAMPLE 50

(2S)-2-(2-Aminoethoxy)-3-(1H-imidazol-4-y)}propanoic acid dihydrochloride

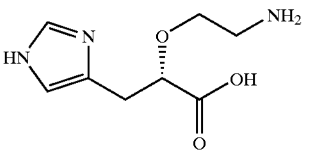 •2HCl

A suspension of the morpholinone of Preparation 118 (90 mg, 0.24 mmol) and lithium hydroxide (32 mg, 1.33 mmol) in a mixture of water (2 ml) and tetrahydrofuran (1 ml) was stirred at room temperature for 18 hours, then concentrated under reduced pressure. The residue was suspended in concentrated hydrochloric acid (3 ml) and the mixture was heated at 110° C. for 18 hours, then cooled and concentrated under reduced pressure. The residue was triturated with acetone and the resulting solid was collected and dried, then recrystallised from methanol/acetone to afford the title compound as a white solid, 12 mg. $^1$H-NMR ($CD_3OD$, 400 MHz) δ: 3.20 (m, 2H), 3.30 (m, 2H), 3.83 (m, 2H), 4.37 (m, 0.5H), 4.41 (m, 0.5H), 7.41 (s, 1H), 8.81 (s, 1H). LRMS: m/z ($ES^-$) 198 [M−H].

EXAMPLE 51

(2S)-2-{[(1R)-2-Amino-1-methylethyl]oxy}-3-(1H-imidazol-4-yl )propanoic acid

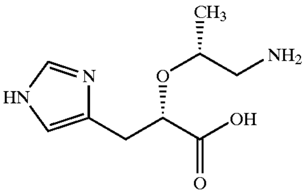

A solution of the morpholinone of Preparation 105 (320 mg, 1.64 mmol) in concentrated hydrochloric acid (5 ml) was heated at 110° C. for 18 hours, then allowed to cool and diluted with water (80 ml). The resulting solution was purified by column chromatography on Dowex® 50WX8-200 ion exchange resin using an elution gradient of water:0.88 ammonia (100:0 to 95:5). The product was dissolved in water and freeze-dried to afford the title compound as a colourless foam, 290 mg. $^1$H-NMR ($D_2O$, 400 MHz) δ: 0.90 (d, 3H), 2.80 (dd, 2H), 2.98 (dd, 2H), 3.57 (m, 1H), 4.04 (m, 1H), 6.84 (s, 1H), 7.60 (s, 1H). LRMS: m/z ($ES^+$) 236 [$MNa^+$]. Microanalysis found: C, 46.00; H, 7.41; N, 17.81. $C_9H_{15}N_3O_4$; $1.25H_2O$ requires C, 45.85; H, 7.48; N, 17.82%. $[\alpha]_D$=−94.62 (c=1.72, water).

Alternative Synthesis

A mixture of the protected lactone of Preparation 55a (1.58 g, 4.42 mmol) and methanesulphonic acid (6.5 ml) was heated at 70° C. for 2.5 hours. The cooled solution was diluted with ether (40 ml), the mixture was stirred, and the ether was decanted off. This process was repeated twice. Water was added and the mixture was stirred vigorously then filtered. The filtrate was allowed to stand at room temperature for 24 hours then purified by column chromatography on Dowex® 50WX8-200 ion exchange resin using water:0.88 ammonia (95:5) as eluant, and the fractions obtained were evaporated under reduced pressure (with water-bath temperature below 33° C.). The product obtained was dissolved in concentrated hydrochloric acid (5 ml), and the solution was heated at 100° C. for 18 hours, then cooled and diluted with water (30 ml). This solution was purified by column chromatography on Dowex® 50WX8-200 ion exchange resin using water:0.88 ammonia (95:5) as eluant. The product was stirred in acetonitrile (10 ml) for 1 hour, filtered and dried in vacuo for 18 hours. Microanalysis found: C, 46.58; H, 7.50; N, 17.98. $C_9H_{15}N_3.1H_2O$ requires C, 46.75; H, 7.41; N. 18.17%.

EXAMPLE 52

(2S)-2-{[(1R)-2-Amino-1-methylethyl]oxy}-3-[1-(2-pyridinyl)-1H-imidazol-4-yl]-propanoic acid dihydrochloride

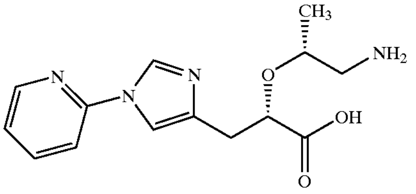

•2HCl

A solution of the morpholinone of Preparation 152 (72 mg, 0.26 mmol) in concentrated hydrochloric acid (3 ml) was heated at 100° C. for 18 hours, then allowed to cool, diluted with water, and concentrated under reduced pressure. The residue was purified by column chromatography on Dowex® 50WX8-200 ion exchange resin using an elution gradient of water:0.88 ammonia (100:0 to 95:5). The product was dissolved in 2N hydrochloric acid and the resulting solution was concentrated under reduced pressure. The residue was dissolved in water (10 ml) and freeze-dried to afford the title compound as a solid, 58 mg. $^1$H-NMR ($D_2O$, 400 MHz) (mixture of imidazole regioisomers) δ: 0.79, 0.99 (2×d, 3H), 2.56, 2.92 (2×m, 1H), 3.02–3.44 (m, 3H), 3.58, 3.78 (2×m, 1H), 7.55 (m, 1H), 7.71 (m, 1H), 7.96–8.19 (m, 2H), 8.52, 8.61 (2×m, 1H), 9.03, 9.38 (2×s, 1H). LRMS: m/z ($ES^+$) 291 [$MH^+$].

EXAMPLE 53

(2S)-2-{[(1R)-2-Amino-1-methylethyl]oxy}-3-(1-propyl-1H-imidazol-4-yl)propanoic acid

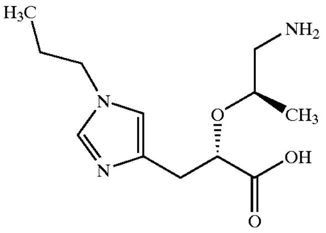

A solution of the compound of Preparation 157 (560 mg, 2.36 mmol) in concentrated hydrochloric acid (10 ml) was stirred at 110° C. for 18 hours. The cooled solution was concentrated under reduced pressure and the residue was purified by column chromatography on ion-exchange resin (Dowex® 50WX8-200) using an elution gradient of water:0.88 ammonia (100:0 to 95:5) to afford the title compound as a foam, 350 mg. $^1$H-NMR ($D_2O$, 400 MHz) δ: 0.66 (t, 3H), 0.81 (d, 3H), 1.60 (m, 2H), 2.60–2.78 (m, 2H), 2.80–2.98 (m, 2H), 3.45 (m, 1H), 3.78 (t, 2H), 3.98 (dd, 1H), 6.82 (s, 1H), 7.43 (s, 1H). LRMS: m/z ($ES^+$) 278 [$MNa^+$]. Microanalysis found: C, 53.44; H, 8.13; N, 15.40 $C_{12}H_{21}N_3O_3$; $0.8H_2O$ requires C, 53.44; H, 8.45; N, 15.58%. $[\alpha]_D$=−86.93° (c=0.11, methanol)

EXAMPLE 54

(2R)-2-{[(1R)-2-Amino-1-methylethyl]oxy}-3-(1H-imidazol-4-yl)propanoic acid

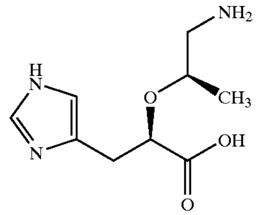

A mixture of the lactam of Preparation 158 (80 mg, 0.50 mmol) and 2N hydrochloric acid (2 ml) was heated at 110° C. for 16 hours, then allowed to cool and diluted with water (10 ml). This solution was purified by column chromatography on Dowex® 50WX8 resin, using water:0.88 ammonia (95:5) as eluant. The product was triturated with acetone and the resulting solid was dried in vacuo to afford the title compound as a brown solid, 68 mg. $^1$H-NMR ($D_2O$, 400 MHz) δ: 1.00 (d, 3H), 2.76 (dd, 2H), 2.83 (m, 2H), 3.60 (m, 1H), 3.86 (m, 1H), 6.79 (s, 1H), 7.57 (s, 1H).

Preparation 1

1-n-Propyl-1H-imidazole-4-carboxaldehyde

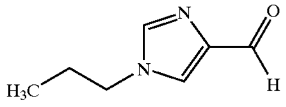

Imidazole-4-carboxaldehyde (30 g, 0.31 mol) was added portionwise to a solution of sodium hydride (13.9 g, 60% dispersion in mineral oil, 0.348 mol) in tetrahydrofuran (450 ml), and the solution was stirred for 45 minutes. n-Propyl bromide (31.2 ml, 0.344 mol) was then added portionwise, followed by 18-crown-6 (150 mg), and the mixture was heated under reflux for 18 hours. Aqueous ammonium chloride solution was added to the cooled solution, and the mixture was extracted with ethyl acetate (2×) and dichloromethane (2×). The combined organic extracts were dried ($MgSO_4$), filtered, and concentrated under reduced pressure. The crude product was purified by column chromatography on silica gel, eluting with ethyl acetate: pentane (40:60), to give the title compound, 20.2 g, 47% yield. $^1$H-NMR (DMSO-$d_6$, 400 MHz) δ: 0.80 (t, 3H), 1.76 (m, 2H), 3.98 (t, 2H), 7.84 (s, 1H), 8.04 (s, 1H), 9.70 (s, 1H). LRMS: m/z ($TSP^+$) 277.3 $[2M+H]^+$ Preparation 2

1-n-Butyl-1H-imidazole-4-carboxaldehyde

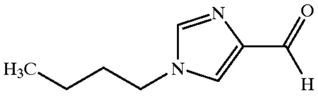

The title compound was obtained in 28% yield from imidazole-4-carboxaldehyde and n-butyl bromide, following a similar procedure to that described in Preparation 1. $^1$H-NMR ($CDCl_3$, 300 MHz) δ: 0.97 (t, 3H), 1.37 (m, 2H), 1.80 (m, 2H), 4.00 (t, 2H), 7.55 (s, 1H), 7.62 (s, 1H), 9.88 (s, 1H). LRMS: m/z ($TSP^+$) 153.3 [$MH^+$].

Preparation 3

1-(2-Cyclohexylethyl)-1H-imidazole-4-carboxaldehyde

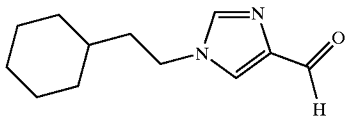

Imidazole-4-carboxaldehyde (4.8 g, 50 mmol) was added portionwise to a suspension of sodium hydride (2.20 g, 60% dispersion in mineral oil, 55 mmol) in tetrahydrofuran (150 ml), and the mixture was then stirred at room temperature for 1 hour. 2-Cyclohexylethyl bromide (8.6 ml, 55 mmol) was added, and the mixture was heated under reflux for 18 hours. The cooled mixture was evaporated under reduced pressure and the residue was partitioned between water (500 ml) and dichloromethane (500 ml). The layers were separated, and the organic phase was dried ($MgSO_4$) and evaporated under reduced pressure. The crude product was purified by column chromatography on silica gel using an elution gradient of toluene:ethyl acetate (100:0 to 96:4) to afford the title compound, 1.78 g. $^1$H-NMR ($CDCl_3$, 400 MHz) δ: 0.98 (m, 2H), 1.20 (m, 4H), 1.68 (m, 7H), 4.00 (t, 2H), 7.4 (s, 1H), 7.60 (s, 1H), 9.80 (s, 1H). LRMS: m/z ($TSP^+$) 207.2 [$MH^+$].

Preparation 4

1-(2-Phenylethyl)-1H-imidazole-4-carboxaldehyde

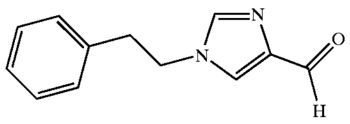

Imidazole-4-carboxaldehyde (6.73 g, 70 mmol) was added portionwise to a suspension of sodium hydride (1.68 g, 60% dispersion in mineral oil, 70 mmol) in tetrahydrofuran (280 ml), and the mixture was then stirred at room temperature for 30 minutes. (2-Bromoethyl)benzene (9.56 ml, 70 mmol) was added, and the mixture was stirred at room temperature for 72 hours. The mixture was evaporated under reduced pressure and the residue was partitioned between water (300 ml) and dichloromethane (500 ml), and the layers were separated. The organic phase was dried ($MgSO_4$) and evaporated under reduced pressure. The crude product was pre-adsorbed onto silica gel, and purified by column chromatography on silica gel using an elution gradient of ethyl acetate:pentane (50:50 to 100:0) to afford the title compound, 1.44 g. $^1$H-NMR ($CDCl_3$, 400 MHz) δ: 3.16 (t, 2H), 4.23 (t, 2H), 7.02 (d, 2H), 7.28 (m, 3H), 7.36 (s, 1H), 7.50 (s, 1H), 9.83 (s, 1H). LRMS: m/z ($ES^+$) 223 [$MNa^+$].

Preparation 5

1-Trityl-1H-imidazole-4-carboxaldehyde

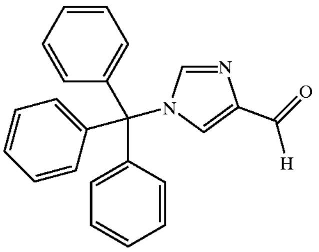

A solution of trityl chloride (9.5 g, 34.3 mmol) in N,N-dimethylformamide (50 ml) was added dropwise to an ice-cooled solution of imidazole-4-carboxaldehyde (3 g, 31.2 mmol) and triethylamine (17 ml, 125 mmol) in N,N-dimethylformamide (30 ml) and the solution was stirred for 2 hours. The reaction was then allowed to warm to room temperature, and was stirred for a further 18 hours. Water (200 ml) was added, and the resulting pink solid was collected and dried, then dissolved in dichloromethane (200 ml). The resulting solution was washed with water (2×100 ml), dried ($MgSO_4$) and evaporated under reduced pressure. The product was recrystallised from ethanol to afford the title compound as a solid, 7.8 g. $^1$H-NMR ($CDCl_3$, 400 MHz) δ: 7.06 (m, 6H), 7.32 (m, 9H), 7.48 (s, 1H), 7.58 (s, 1H), 9.82 (s, 1H). Microanalysis found: C, 81.54; H, 5.37; N, 8.24. $C_{23}H_{18}N_2O$ requires C, 81.63; H, 5.36; N, 8.28%.

Preparation 6

2-[(4-Methoxybenzyl)amino]ethanol

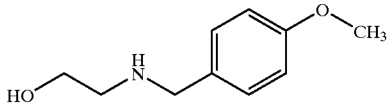

Acetic acid (ca. 150 ml) was added to a solution of p-anisaldehyde (58.2 g, 0.42 mol) and ethanolamine (152 ml, 2.52 mol) in methanol (1L), to achieve a pH of 6. Sodium triacetoxyborohydride (100 g, 0.47 mol) was added portionwise, and once addition was complete, the mixture was stirred at room temperature for 72 hours. The mixture was concentrated under reduced pressure, basified using 1N sodium hydroxide solution and extracted with dichloromethane (10×300 ml). The combined extracts were evaporated and the crude product was purified by column chromatography on silica gel using an elution gradient of dichloromethane:methanol (98:2 to 90:10) to afford the title compound, 42 g. $^1$H-NMR ($CDCl_3$, 400 MHz) δ: 2.78 (t, 2H), 3.62 (t, 2H), 3.75 (m, 5H), 4.24 (s, 2H), 6.81 (d, 2H), 7.22 (d, 2H). LRMS: m/z ($ES^+$) 182 [$MH^+$].

Preparation 7

(2R)-1-[(4-Methoxybenzyl)amino]-2-propanol

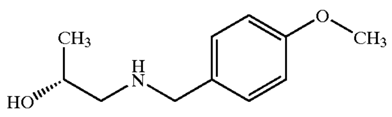

A solution of (R)-(−)-1-amino-2-propanol (9.00 g, 0.12 mol) in tetrahydrofuran (40 ml) and acetic acid (5 ml) was added dropwise to a solution of p-anisaldehyde (5.45 g, 0.04 mol) in tetrahydrofuran (40 ml), and once addition was complete, the solution was stirred at room temperature for 2 hours. The solution was cooled in an ice-bath, and sodium triacetoxyborohydride (9.50 g, 0.0.045 mol) was added portionwise, and then the mixture was stirred at room temperature for 18 hours. The reaction mixture was concentrated under reduced pressure and the residue was partitioned between dichloromethane (150 ml) and sodium hydroxide solution (150 ml, 0.5N). The layers were separated and the aqueous phase was saturated with sodium chloride, then extracted with further dichloromethane (3×30 ml). The combined organic solutions were dried ($MgSO_4$) and evaporated under reduced pressure. The residue was purified by chromatography on silica gel (gradient elution 98:2:0.2 to 97:3:0.3 dichloromethane:methanol:0.88 $NH_3$) to afford an orange oil (4.9 g). $^1$H-NMR ($CDCl_3$, 400 MHz) δ: 1.12 (d, 3H), 2.39 (dd, 1H), 2.70 (dd, 1H), 3.62–3.79 (m, 6H), 6.82 (d, 2H), 7.19 (d, 2H). LRMS: m/z ($ES^+$) 196 [$MH^+$].

Preparation 8

(2S)-1-[(4-Methoxybenzyl)amino]-2-propanol

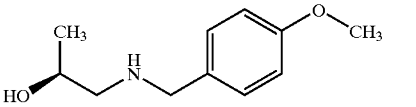

A mixture of (S)-(+)-1-amino-2-propanol (9 g, 0.12 mol), p-anisaldehyde (5.45 g, 0.04 mol), acetic acid (5 ml), and sodium triacetoxyborohydride (9.5 g, 0.045 mol) in methanol (80 ml) was stirred at room temperature for 72 hours. The reaction mixture was concentrated under reduced pressure and the residue was partitioned between dichloromethane (150 ml) and sodium hydroxide solution (100 ml, 0.5N). The layers were separated, and the aqueous phase was extracted with further dichloromethane (4×30 ml). The combined organic solutions were dried ($MgSO_4$) and concentrated under reduced pressure. The residual yellow oil was purified by column chromatography on silica gel using an elution gradient of dichloromethane:methanol:0.88 ammonia (98:2:0.2 to 95:5:0.5) to afford the title compound, 6.2 g. $^1$H-NMR ($CDCl_3$, 400 MHz) δ: 1.10 (d, 3H), 2.24–2.40 (m, 2H), 2.65 (dd, 1H), 3.62–3.80 (m, 6H), 6.82 (d, 2H), 7.19 (d, 2H). LRMS: m/z ($ES^+$) 218 [$MNa^+$]

Preparation 9

(2R)-2-[(4-Methoxybenzyl)amino]-1-propanol

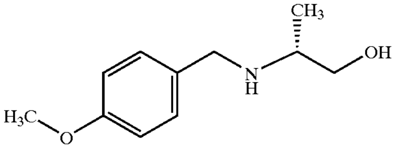

(R)-(−)-2-Amino-1-propanol (10.36 ml, 133 mmol) was added dropwise to a solution of p-anisaldehyde (5.85 g, 42.9 mmol) in methanol (90 ml), and the solution was cooled in an ice-bath. Acetic acid (2.5 ml) and sodium triacetoxyborohydride (10.0 g, 47.2 mmol) were added and the reaction mixture was allowed to warm to room temperature over an hour. The solution was warmed to 40° C. and stirred for a further 48 hours then concentrated under reduced pressure. The residue was partitioned between saturated sodium bicarbonate solution (50 ml) and dichloromethane (100 ml) and the layers were separated. The aqueous phase was extracted with further dichloromethane (10×50 ml), and the combined organic solutions were dried ($MgSO_4$) and evaporated under reduced pressure. The residue was purified twice by column chromatography on silica gel using an elution gradient of dichloromethane:methanol:0.88 ammonia (97:3:0.3 to 90:10:1) to afford the title compound, 6.0 g. $^1$H-NMR ($CDCl_3$, 400 MHz) δ: 1.04 (d, 3H), 2.80 (m, 1H), 322 (dd, 1H), 3.58 (dd, 1H), 3.62 (d, 1H), 3.78 (m, 4H), 6.82 (d, 2H), 7.20 (d, 2H). LRMS: m/z ($ES^+$) 196 [$MH^+$]. $[\alpha]_D$=−34.85 (c=0.137, methanol)

Preparation 10

(2S)-2-[(4-Methoxybenzyl)amino]-1-propanol

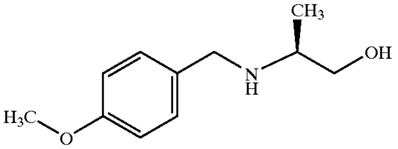

The title compound was obtained in 67% yield from (S)-(+)-2-amino-1-propanol and p-anisaldehyde, following the procedure described in Preparation 9. $^1$H-NMR ($CDCl_3$, 400 MHz) δ: 1.08 (d, 3H), 2.83 (m, 1H), 3.30 (dd, 1H), 3.59 (dd, 1H), 3.66 (d, 1H), 3.77 (s, 3H), 3.82 (d, 1H), 4.08 (bs, 2H), 6.82 (d, 2H), 7.22 (d, 2H). $[\alpha]_D$=+39.19 (c=0.146, methanol)

Preparation 11

4-(4-Methoxybenzyl)-3-morpholinone

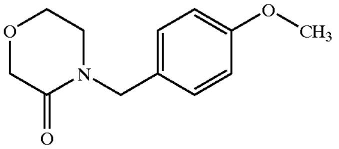

A solution of sodium hydroxide (7.08 g, 0.177 mol) in water (150 ml) was added to a solution of the amino alcohol of Preparation 6 (32 g, 0.177 mol) in dichloromethane (250 ml), and the mixture was cooled to 0° C. A solution of chloroacetyl chloride (14.3 ml, 0.177 mol) in dichloromethane (50 ml) was added dropwise over 30 minutes, and the mixture was stirred at room temperature for 18 hours. The phases were separated, and the organic layer was washed with sodium hydroxide (2N, 150 ml), 2N hydrochloric acid (150 ml), and brine (50 ml), then dried ($MgSO_4$) and concentrated under reduced pressure. The residual oil was dissolved in ethanol (200 ml), a solution of potassium hydroxide (9.93 g, 0.177 mol) in ethanol (200 ml) was added and the mixture was stirred at room temperature for 18 hours. The mixture was filtered, the filtrate was evaporated under reduced pressure, and the residue was triturated with diethyl ether/pentane to afford the title compound as a white powder, 26 g. $^1$H-NMR ($CDCl_3$, 400 MHz) δ: 3.20 (t, 2H), 3.78 (m, 5H), 4.19 (s, 2H), 4.54 (s, 2H), 6.82 (d, 2H), 7.18 (d, 2H). LRMS: m/z ($ES^+$) 244 [$MNa^+$].

Preparation 12

(6R)-4-(4-Methoxybenzyl)-6-methyl-3-morpholinone

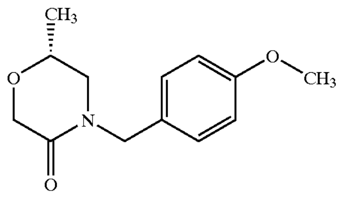

The title compound was obtained in 76% yield from the alcohol of Preparation 7 and chloroacetyl chloride, following a similar procedure to that described in Preparation 11, except, the compound was additionally purified by column chromatography on silica gel using dichloromethane:methanol:0.88 ammonia (98:2:0.2) as eluant. $^1$H-NMR ($CDCl_3$, 400 MHz) δ: 1.18 (d, 3H), 2.99–3.14 (m, 2H), 3.79 (m, 4H), 4.17 (d, 1H), 4.25 (d, 1H), 4.38 (d, 1H), 4.61 (d, 1H), 6.82 (d, 2H), 7.17 (d, 2H). LRMS: m/z ($ES^+$) 258 [$MNa^+$]

Preparation 13

(6S)-4-(4-Methoxybenzyl)-6-methyl-3-morpholinone

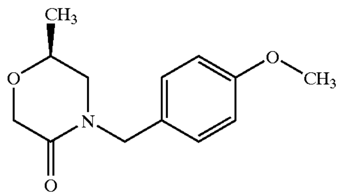

The title compound was obtained as a yellow oil in 61% yield from the amino alcohol of Preparation 8, following the procedure described in Preparation 11. $^1$H-NMR ($CDCl_3$, 400 MHz) δ: 1.18 (d, 3H), 2.98–3.10 (m, 2H), 3.78 (m, 4H), 4.18 (d, 1H), 4.25 (d, 1H), 4.38 (d, 1H), 4.60 (d, 1H), 6.61 (d, 2H), 7.17 (d, 2H). LRMS: m/z ($ES^+$) 258 [$MNa^+$]

Preparation 14

(5S)-4-(4-Methoxybenzyl)-5-methyl-3-morpholinone

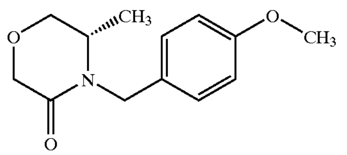

A solution of chloroacetyl chloride (2.34 ml, 29 mmol) in dichloromethane (25 ml) was added dropwise over 10 minutes to a stirred ice-cooled mixture of the amino alcohol of Preparation 10 (5.6 g, 28.7 mmol) in sodium hydroxide solution (1.16 g, 29 mmol in water (20 ml)) and dichloromethane (50 ml). The mixture was stirred at room temperature for 18 hours, and then the layers were separated. The organic phase was washed with 1N sodium hydroxide solution (25 ml), 2M hydrochloric acid (20 ml) and brine (20 ml), then dried ($MgSO_4$) and evaporated under reduced pressure. The residue was dissolved in ethanol (40 ml) the solution was cooled in an ice-bath, and a solution of potassium hydroxide (1.63 g, 29 mmol) in ethanol (40 ml) was added dropwise over 5 minutes. The mixture was then allowed to warm to room temperature and was stirred for a further 18 hours. The resulting precipitate was filtered off, the filtrate was concentrated under reduced pressure, and the residue was dissolved in dichloromethane (150 ml). This solution was dried ($MgSO_4$) and evaporated under reduced pressure. The crude product was purified by column chromatography on silica gel using an elution gradient of dichloromethane:methanol:0.88 ammonia (97:3:0.3 to 95:5:0.5) to afford the title compound, 4 g. $^1$H-NMR ($CDCl_3$, 400 MHz) δ: 1.26 (d, 3H), 3.37 (m, 1H), 3.62 (dd, 1H), 3.70 (dd, 1H), 3.80 (s, 3H), 3.90 (d, 1H), 4.20 (d, 1H), 4.24 (d, 1H), 5.33 (d, 1H), 6.83 (d, 2H), 7.19 (d, 2H). $[\alpha]_D$=−109.66 (c=0.139, methanol)

Preparation 15

(5R)-4-(4-Methoxybenzyl)-5-methyl-3-morpholinone

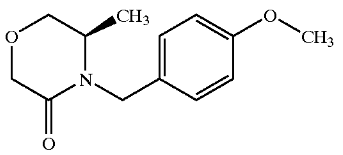

The title compound was obtained in 49% yield from the alcohol of Preparation 9 following a similar procedure to that described in Preparation 14. $^1$H-NMR ($CDCl_3$, 400 MHz) δ: 1.24 (d, 3H), 3.30 (m, 1H), 3.60 (dd, 1H), 3.70 (dd, 1H), 3.78 (s, 3H), 3.85 (d, 1H), 4.18 (d, 1H), 4.22 (d, 1H), 5.28 (d, 1H), 6.81 (d, 2H), 7.18 (d, 2H).

Preparation 16

4-Methyl-3-morpholinone

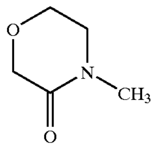

A solution of chloroacetyl chloride (3.81 ml, 50 mmol) in dichloromethane (100 ml) was added dropwise over 30 minutes to a suspension of 2-(methylamino)ethanol (4 ml, 50 mmol) and sodium hydroxide (2 g, 50 mmol) in dichloromethane (50 ml) and water (50 ml), and the mixture was stirred at room temperature for 72 hours then evaporated under reduced pressure. The residue was dissolved in ethanol (100 ml), potassium hydroxide (2.8 g, 50 mmol) was added, and the mixture was stirred at 40° C. for 18 hours then filtered, and the filtrate was concentrated under reduced pressure. The crude product was purified by column chromatography on silica gel using an elution gradient of pentane:ethyl acetate (100:0 to 50:50 to 0:100), to afford the title compound, 3.42 g. $^1$H-NMR ($CDCl_3$, 400 MHz) δ: 2.98 (s, 3H), 3.34 (t, 2H), 3.84 (t, 2H), 4.14 (s, 2H). Found: C, 51.55; H, 8.02; N, 12.01. $C_5H_9NO_2$; $0.1H_2O$ requires C, 51.36; H, 7.93; N, 11.98%.

Preparation 17 tert-Butyl [2-(dimethylamino)ethoxy]acetate

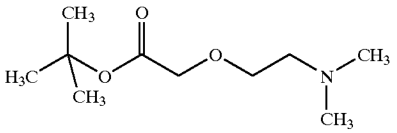

N,N-Dimethylethanolamine (5.02 ml, 50 mmol) was added dropwise over 5 minutes to an ice-cooled suspension of sodium hydride (2.2 g, 60% dispersion in mineral oil, 55 mmol) in tetrahydrofuran (100 ml), and the solution was stirred for 30 minutes. tert-Butyl bromoacetate (7.38 ml, 50 mmol) was added dropwise over 5 minutes, then the mixture was allowed to warm to room temperature and stirred for a further 18 hours. The mixture was pre-adsorbed onto silica gel, and purified by column chromatography on silica gel using an elution gradient of pentane:ethyl acetate:methanol (50:50:0 to 0:100:0 to 0:80:20) to afford the title compound as a yellow oil, 1.46 g. $^{1}$H-NMR ($CDCl_3$, 400 MHz) δ: 1.50 (s, 9H), 2.30 (s, 6H), 2.59 (t, 2H), 3.64 (t, 2H) 4.00 (s, 2H). LRMS: m/z ($ES^+$) 204 [$MH^+$]

Preparation 18 tert-Butyl (3R)-3-(2-tert-butoxy-2-oxoethoxy) pyrrolidine-1-carboxylate

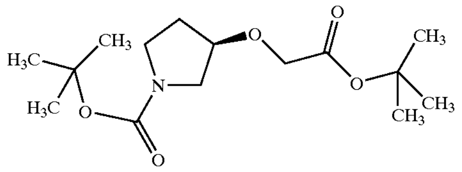

Sodium hydride (704 mg, 60% in mineral oil, 17.6 mmol) was added to an ice-cooled solution of tert-butyl (3R)-3-hydroxypyrrolidine-1-carboxylate (*J. Med. Chem.* 1998, 41(25), 4983) (5 g, 26.7 mmol) in tetrahydrofuran (100 ml), and the mixture was allowed to warm to room temperature and stirred for 20 minutes. tert-Butyl bromoacetate (5.2 g, 26.7 mmol) was added and the mixture was heated under reflux for 18 hours, then cooled and concentrated under reduced pressure. The residue was partitioned between ethyl acetate and water and the phases separated. The organic layer was dried ($MgSO_4$) and evaporated under reduced pressure. The crude product was purified by column chromatography on silica gel using an elution gradient of ethyl acetate:pentane (0:100 to 20:80) to afford the title compound, 1.95 g.

$^{1}$H-NMR ($CDCl_3$, 400 MHz) δ: 1.42 (s, 9H), 1.44 (s, 9H), 1.85–2.05 (m, 2H), 3.40 (m, 4H), 3.94 (m, 2H), 4.10 (m, 1H). LRMS: m/z ($ES^+$) 324 [$MNa^+$]

Preparation 19

Ethyl 3-cyclohexyl-3-methylbutanoate

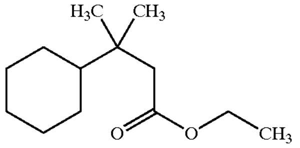

Trimethylsilyl chloride (1.3 ml, 10.2 mmol), copper (I) chloride (30 mg, 0.3 mmol) and cyclohexylmagnesium chloride (4.6 ml, 2N in diethyl ether, 9.2 mmol) were added slowly to an ice-cooled solution of ethyl 3,3-dimethylacrylate (1 g, 8.5 mmol) in tetrahydrofuran (10 ml). The solution was stirred for 10 minutes, then allowed to warm to room temperature and stirred for an hour. Saturated aqueous ammonium chloride solution (10 ml) was added and the mixture was partitioned between water (10 ml) and diethyl ether (20 ml). The layers were separated and the aqueous phase was extracted with diethyl ether (2×10 ml). The combined organic extracts were dried ($MgSO_4$) and concentrated under reduced pressure. The crude product was purified by column chromatography on silica gel using ethyl acetate:pentane(5:95) as eluant to afford the title compound, 1.2 g. $^{1}$H-NMR ($CDCl_3$, 400 MHz) δ: 0.75 (m, 8H), 1.05–1.28 (m, 7H), 1.62 (m, 1H), 1.78 (m, 4H), 2.20 (s, 2H), 4.10 (q, 2H).

Preparation 20

3-Cyclohexyl-3-methyl-1-butanol

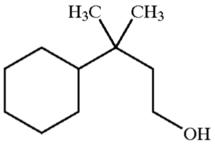

Lithium borohydride (1.23 g, 56.6 mmol) was added to a solution of the ester of Preparation 19 (4 g, 18.9 mmol) in tetrahydrofuran (30 ml), and the mixture was stirred at 50° C. for 18 hours. Aqueous ammonium chloride solution (15 ml) was added carefully to the cooled solution, and the mixture was extracted with ethyl acetate (3×30 ml). The combined organic extracts were washed with brine, dried ($MgSO_4$) and evaporated under reduced pressure. The crude product was purified by column chromatography on silica gel using ethyl acetate:pentane (20:80) as eluant to afford the title compound, 1 g. $^{1}$H-NMR ($CDCl_3$, 400 MHz) δ: 0.80 (s, 6H), 0.88–1.18 (m, 6H), 1.50 (t, 2H), 1.60 (m, 1H), 1.70 (m, 4H), 3.64 (m, 2H).

Preparation 21

(3-Bromo-1,1-dimethylpropyl)cyclohexane

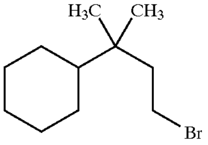

Triphenylphosphine (1.8 g, 7.1 mmol) was added portionwise to an ice-cooled solution of the alcohol of Preparation 20 (1 g, 5.9 mmol) and carbon tetrabromide (2.9 g, 8.8 mmol) in dichloromethane (15 ml), and once addition was complete, the mixture was stirred at room temperature for 72 hours. The solution was concentrated under reduced pressure and the residue was suspended in a mixture of pentane:ethyl acetate (5:1, by volume). The resulting precipitate was filtered off through a pad of silica gel and washed with pentane:ethyl acetate (5:1, by volume, 300 ml). The combined filtrates were concentrated under reduced pressure, and the product was purified by column chromatography on silica gel using pentane as eluant to afford the title compound, 1.1 g. $^{1}$H-NMR ($CDCl_3$, 400 MHz) δ: 0.80 (2xs, 6H), 0.90–1.20 (m, 6H), 1.62 (m, 3H), 1.75 (m, 2H), 1.81 (m, 2H), 3.36 (m, 2H).

Preparation 22

4-(2-Bromoethyl)-1,1-dimethylcyclohexane

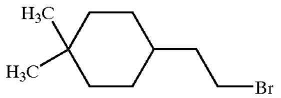

A mixture of 2-(4,4-dimethylcyclohexyl)ethanol (WO99/59971) (2 g, 12.8 mmol), concentrated sulphuric acid (750 μl) and 48% hydrobromic acid (3 ml) was stirred at 90° C. for 7 hours. The cooled mixture was then carefully quenched by the addition of water (25 ml), and the mixture was extracted with dichloromethane (3x30 ml). The combined organic extracts were washed with 2M sodium carbonate solution and brine (30 ml), then dried ($MgSO_4$) and concentrated under reduced pressure. The residual black gum was purified by distillation to afford the title compound, 330 mg. $^{1}$H-NMR ($CDCl_3$, 400 MHz) δ: 0.82 (2xs, 6H), 1.02–1.20 (m, 4H), 1.35 (m, 3H), 1.50 (m, 2H), 1.78 (m, 2H), 3.40 (t, 2H).

Preparation 23

2-[Hydroxy(1-propyl-1H-imidazol-4-yl)methyl]-4-(4-methoxybenzyl)-3-morpholinone

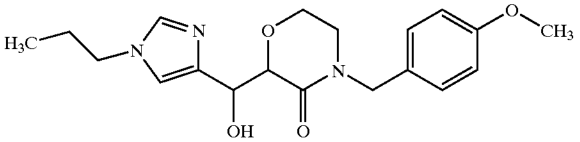

A solution of the compound of Preparation 11 (13 g, 58.7 mmol) in tetrahydrofuran (100 ml) was added dropwise to a solution of lithium diisopropylamide (35.3 ml, 2M in tetrahydrofuran/heptane/ethylbenzene, 70.5 mmol) at −78° C., and the solution was stirred at −78° C. for 20 minutes. The aldehyde of Preparation 1 (9.75 g, 70.5 mmol) was added dropwise and the mixture was allowed to warm to room temperature, then stirred for 1.5 hours. Ammonium chloride solution (100 ml) was added and the mixture was diluted with water (100 ml) and tetrahydrofuran (300 ml). The layers were separated, the aqueous phase was extracted with tetrahydrofuran (250 ml), and the combined organic solutions were dried ($MgSO_4$) and evaporated under reduced pressure. The crude product was purified by column chromatography on silica gel using an elution gradient of ethyl acetate:dichloromethane:methanol:0.88 ammonia (100:0:0:0 to 0:95:5:0.5) to afford the title compound, 14 g. $^{1}$H-NMR ($CDCl_3$, 400 MHz) (mixture of diastereoisomers) δ: 0.90 (t, 3H), 1.76 (m, 2H), 3.00 (m, 1H), 3.32–3.43 (m, 1H), 3.61–3.81 (m, 6H), 3.98 (m, 1H), 4.75 (m, 0.5H), 5.03 (m, 0.5H), 6.81 (m, 3H), 7.15 (m, 2H), 7.38 (s, 1H). LRMS: m/z ($ES^+$) 360.0 [$MH^+$]

Preparation 24

2-[Hydroxy(1-propyl-1H-imidazol-4-yl)methyl]-4-methyl-3-morpholinone

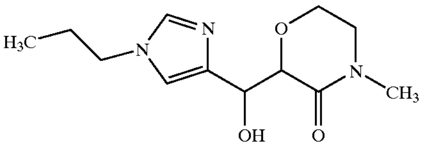

Lithium diisopropylamide (17.4 ml, 2M in heptane/tetrahydrofuran/ethylbenzene, 34.8 mmol) was added over 10 minutes to a cooled (−78° C.) solution of the compound of Preparation 10 (3.42 g, 29 mmol) in tetrahydrofuran (100 ml), and the resulting solution was stirred for 20 minutes. The aldehyde of Preparation 1 (4.81 g, 34.8 mmol) was added and the mixture was allowed to warm slowly to room temperature, then stirred for 18 hours. Aqueous ammonium chloride solution (20 ml) was added, and the mixture was evaporated under reduced pressure. The residue was purified by column chromatography on silica gel using an elution gradient of pentane:ethyl acetate:methanol:diethylamine (50:50:0:0 to 0:100:0:0 to 0:90:5:5) to afford the title compound as a yellow gum, 5.47 g. $^{1}$H-NMR ($CDCl_3$, 400 MHz) (mixture of diastereoisomers) δ: 0.90 (t, 3H), 1.78 (m, 2H), 2.98 (2xs, 3H), 3.10 (m, 1H), 3.57 (m, 2H), 3.80 (m, 3H), 3.98–4.08 (m, 1H), 4.39, 4.49, 4.86, 4.98, 5.22 (5xm, 2H), 6.88 (s, 1H), 7.38 (s, 1H). LRMS: m/z ($TSP^+$) 254.2 [$MH^+$]

Preparation 25

2-[(1-Butyl-1H-imidazol-4-yl)(hydroxy)methyl]-4-(4-methoxybenzyl)-3-morpholinone

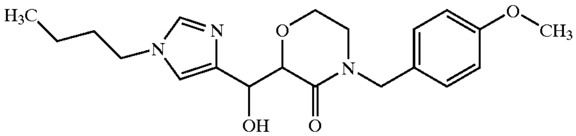

A solution of the compound of Preparation 11 (3.63 g, 16.4 mmol) in tetrahydrofuran (40 ml) was added dropwise over 5 minutes to a solution of lithium diisopropylamide (9.8 ml, 2M in tetrahydrofuran/heptane/ethylbenzene, 19.7 mmol) at −78° C., and the solution was stirred at −78° C. for 30 minutes. The aldehyde of Preparation 2 (3.0 g, 19.7 mmol) was added dropwise and the mixture was allowed to warm to room temperature, then stirred for 18 hours. The mixture was partitioned between ammonium chloride solution and ethyl acetate (300 ml). The layers were separated, and the organic solution was dried ($MgSO_4$) and evaporated under reduced pressure. The crude product was purified by column chromatography on silica gel using an elution gradient of ethyl acetate:methanol: (100:0 to 90:10) to afford the title compound, 4.35 g. $^{1}$H-NMR ($CDCl_3$, 400 MHz) (mixture of diastereoisomers) δ: 0.96 (t, 3H), 1.35 (m, 2H), 1.78 (m, 2H), 3.03 (m, 1H), 3.42 (m, 1H), 3.66–3.80 (m, 5H), 3.87 (m, 2H), 4.00 (m, 1H), 4.50 (m, 0.5H), 4.57 (m, 2.5H), 4.83 (m, 0.5H), 5.06 (m, 0.5H), 6.90 (m, 3H), 7.20 (m, 2H), 7.41 (s, 1H). LRMS: m/z ($TSP^+$) 374.0 [$MH^+$]

Preparation 26

2-[[1-(2-Cyclohexylethyl)-1H-imidazol-4-yl](hydroxy)methyl]-4-(4-methoxybenzyl)-3-morpholinone

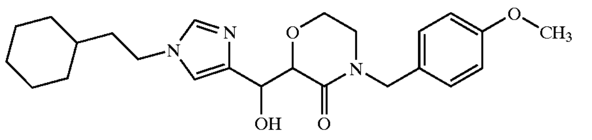

The title compound was obtained as a sticky gum in 66% yield from the compound of Preparation 11 and the aldehyde of Preparation 3, following a similar procedure to that described in Preparation 25. $^1$H-NMR ($CDCl_3$, 400 MHz) (mixture of diastereoisomers) □: 0.98 (m, 2H), 1.22 (m, 4H), 1.58–1.78 (m, 7H), 3.03 (m, 1H), 3.38–3.50 (m, 1H), 3.70–3.82 (m, 4H), 3.90 (m, 2H), 4.01 (m, 1H), 4.50 (d, 0.5H), 4.58 (m, 2.5H), 4.87 (m, 0.5H), 5.08 (m, 0.5H), 6.82–6.95 (m, 3H), 7.19 (m, 2H), 7.41 (s, 1H). LRMS: m/z ($TSP^+$) 428.1 [$MH^+$]

Preparation 27

2-{Hydroxy[1-(2-phenylethyl)-1H-imidazol-4-yl]methyl}-4-(4-methoxybenzyl)-3-morpholinone

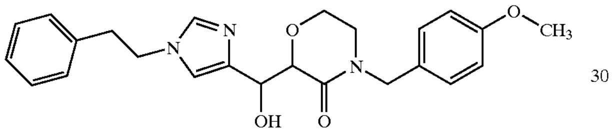

The title compound was obtained in 54% yield from the compound of Preparation 11 and the aldehyde of Preparation 4, following a similar procedure to that described in Preparation 25, except pentane:ethyl acetate:methanol (50:50:0 to 0:100:0 to 0:87:13) was used as the elution gradient. $^1$H-NMR ($CDCl_3$, 400 MHz) (mixture of diastereoisomers) δ: 3.02 (m, 3H), 3.42 (m, 1H), 3.74 (m, 4H), 3.95–4.05 (m, 1H), 4.12 (m, 2H), 4.45 (m, 0.5H), 4.58 (m, 2.5H), 4.81 (m, 0.5H), 5.06 (d, 0.5H), 6.84 (m, 3H), 7.07 (d, 2H), 7.19 (m, 2H), 7.27 (m, 4H). LRMS: m/z ($ES^+$) 422 [$MH^+$]

Preparation 28

2-[Hydroxy(1-trityl-1H-imidazol-4-yl)methyl]-4-(4-methoxybenzyl)-3-morpholinone

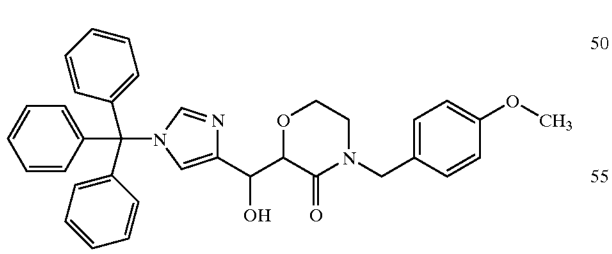

A solution of lithium diisopropylamide (88.5 ml, 1.5M in cyclohexane, 133 mmol) and tetrahydrofuran (100 ml) was cooled to −78° C. A solution of the compound of Preparation 11 (26 g, 118 mmol) in tetrahydrofuran (100 ml) was added dropwise, and the solution was stirred for 30 minutes. A solution of the imidazole of Preparation 5 (39.9 g, 118 mmol) in tetrahydrofuran (350 ml) was added dropwise over 1 hour, and once addition was complete, the reaction was allowed to warm slowly to room temperature with stirring, over 3 hours. Saturated ammonium chloride solution (200 ml) and water (100 ml) were added, the phases were separated, and the aqueous layer was extracted with ethyl acetate (100 ml). The combined organic solutions were dried ($MgSO_4$) and evaporated under reduced pressure. The residual orange oil was dissolved in ethyl acetate/methanol, the solution was sonicated, and the resulting white precipitate was filtered off, washed with diethyl ether and dried, to give the title compound, 21 g. The filtrate was evaporated under reduced pressure and the residue was purified by column chromatography on silica gel using ethyl acetate: methanol (96:4) as eluant to afford additional product, 28 g. $^1$H-NMR ($CDCl_3$, 400 MHz) (mixture of diastereoisomers) δ: 2.98 (m, 1H), 3.35 (m, 1H), 3.66 (m, 1H), 3.73 (s, 3H), 3.96 (m, 1H), 4.40 (d, 1H), 4.54 (s, 1H), 4.60 (d, 1H), 5.21 (m, 1H), 6.79 (m, 3H), 7.08 (m, 6H), 7.15 (m, 2H), 7.26 (m, 9H), 7.37 (s, 1H). LRMS: m/z ($TSP^+$) 560.2 [$MH^+$]

Preparation 29

(6R)-2-[Hydroxy(1-trityl-1H-imidazol-4-yl)methyl]-4-(4-methoxybenzyl)-6-methyl-3-morpholinone

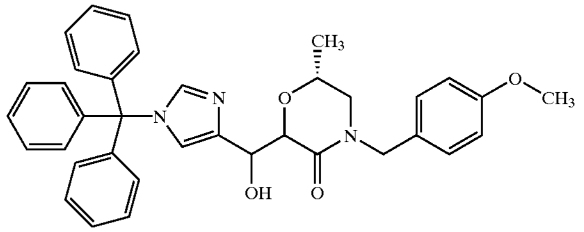

The title compound was obtained in 62% yield from the morpholinone of Preparation 12 and the imidazole of Preparation 5, following a similar procedure to that described in Preparation 28. $^1$H-NMR ($CDCl_3$, 400 MHz) (mixture of diastereoisomers) δ: 1.00, 1.06 (2×m, 3H), 2.87–3.04 (m, 2H), 3.76 (m, 3H), 3.80–4.74 (m, 4H), 4.98–5.21 (m, 1H), 6.78 (m, 3H), 7.05–7.20 (m, 8H), 7.23–7.40 (m, 10H). LRMS: m/z ($ES^+$) 574 [$MH^+$]

Preparation 30

(6S)-2-[Hydroxy(1-trityl-1H-imidazol-4-yl)methyl]-4-(4-methoxybenzyl)-6-methyl-3-morpholinone

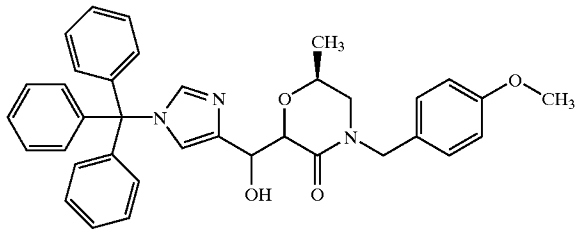

The title compound was obtained as a yellow foam in 53% yield from the morpholinone of Preparation 13 and the imidazole of Preparation 5, following a similar procedure to that described in Preparation 28. $^1$H-NMR ($CDCl_3$, 400 MHz) (mixture of diastereoisomers) δ: 1.00, 1.05 (2×m, 3H), 2.85–3.04 (m, 2H), 3.76 (m, 3H), 3.80–3.96 (m, 1H), 4.39–4.70 (m, 3H), 4.98–5.20 (m, 1H), 6.78 (m, 3H), 7.05–7.20 (m, 8H), 7.25 (m, 9H), 7.39 (m, 1H). LRMS: m/z ($ES^+$) 574 [$MH^+$]

Preparation 31

(5S)-2-[Hydroxy(1-trityl-1H-imidazol-4-yl)methyl]-4-(4-methoxybenzyl)-5-methyl-3-morpholinone

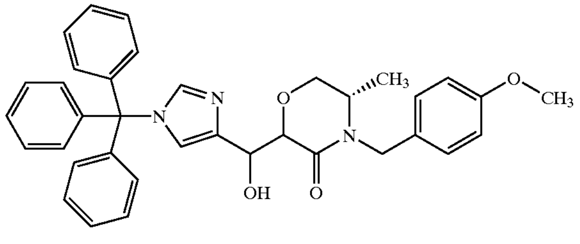

The title compound was obtained in 57% yield from the morpholinone of Preparation 14 and the imidazole of Preparation 5, following a similar procedure to that described in Preparation 28. $^1$H-NMR ($CDCl_3$, 400 MHz) (mixture of diastereoisomers) δ: 1.03–1.19 (m, 3H), 2.99–4.83 (m, 8H), 5.02–5.38 (m, 2H), 6.78–6.88 (m, 3H), 7.10–7.21 (m, 8H), 7.22–7.42 (m, 10H).

Preparation 32

(5R)-2-[Hydroxy(1-trityl-1H-imidazol-4-yl )methyl]-4-(4-methoxybenzyl)-5-methyl-3-morpholinone

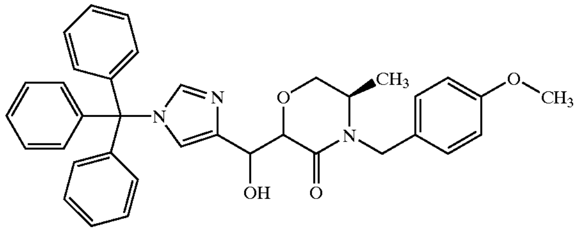

The title compound was obtained as a yellow foam in 80% yield from the morpholinone of Preparation 15 and the imidazole of Preparation 5, following a similar procedure to that described in Preparation 28. $^1$H-NMR ($CDCl_3$, 400 MHz) (mixture of diastereoisomers) δ: 1.00–1.16 (m, 3H), 3.16–4.94 (m, 8H), 5.00–5.37 (m, 2H), 6.72–6.83 (m, 3H), 7.04–7.19 (m, 8H), 7.21–7.40 (m, 10H).

Preparation 33 tert-Butyl 2-[2-(dimethylamino)ethoxy]-3-hydroxy-3-(1-propyl-1H-imidazol-4-yl)propanoate

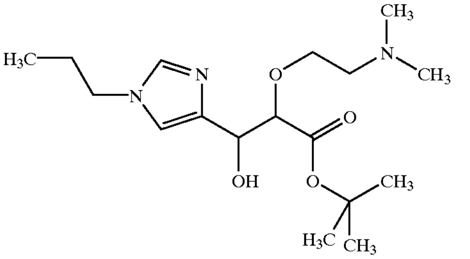

Lithium diisopropylamide (4.3 ml, 2M in heptane/tetrahydrofuran/ethylbenzene, 8.6 mmol) was added dropwise over 5 minutes to a solution of the amine of Preparation 17 (1.46 g, 7.2 mmol) in tetrahydrofuran (20 ml) and the solution was stirred at −78° C. for 20 minutes. The aldehyde of Preparation 1 (1.18 g, 8.6 mmol) was added and the mixture was stirred for 3 hours then allowed to warm to −20° C. Water was added, and the mixture pre-adsorbed onto silica gel. The product was purified by column chromatography on silica gel using an elution gradient of ethyl acetate:methanol:diethylamine (100:0:0 to 96:2:2) to afford the title compound, 1.36 g. $^1$H-NMR ($CDCl_3$, 400 MHz) (mixture of diastereoisomers) δ: 0.88 (m, 3H), 1.35 (2×s, 9H), 1.75 (m, 2H), 2.22 (s, 6H), 2.42 (m, 1H), 2.58 (m, 1H), 3.55 (m, 1H), 3.80 (m, 2H), 3.90 (m, 1H), 4.17 (m, 1H), 4.82, 5.00 (m, 1H), 6.90 (2×s, 1H), 7.35 (2×s, 1H). LRMS: m/z ($TSP^+$) 342.2 [$MH^+$]

Preparation 34 tert-Butyl (3S)-3-{1-tert-butoxycarbonyl-2-hydroxy-2-(1-propyl-1H-imidazol-4-yl)-ethoxy}pyrrolidine-1-carboxylate

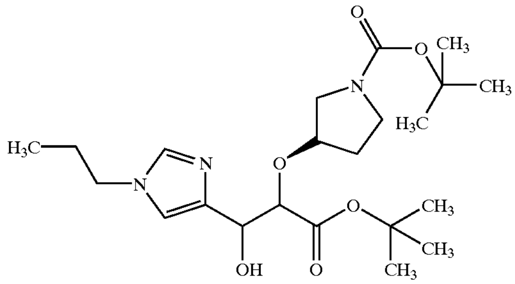

A solution of the compound of Preparation 18 (5.67 g, 18.8 mmol) in tetrahydrofuran (20 ml) was added dropwise to a solution of lithium diisopropylamide (11.3 ml, 2M in heptane/tetrahydrofuran/ethylbenzene, 22.6 mmol) at −78° C., and the solution was stirred at −78° C. for 20 minutes. The aldehyde of Preparation 1 (3.12 g, 22.6 mmol) was added portionwise, and the mixture was allowed to warm to room temperature then stirred for 18 hours. Ammonium chloride solution (50 ml) was added carefully and the mixture was extracted with tetrahydrofuran (2×200 ml). The combined organic solutions were dried ($MgSO_4$) and evaporated under reduced pressure. The residual orange oil was purified by column chromatography on silica gel using an elution gradient of dichloromethane:methanol:0.88 ammonia (100:0:0: to 90:10:1) to afford the title compound, 3.7 g. $^1$H-NMR ($CDCl_3$, 400 MHz) (mixture of diastereoisomers) δ: 0.92 (t, 3H), 1.42 (s, 18H), 1.79 (m, 2H), 1.94–2.14 (m, 1H), 2.75–3.50 (m, 5H), 3.84 (m, 2H), 4.03–4.35 (m, 2H), 4.81–5.08 (m, 2H), 6.88 (m, 1H), 7.39 (s, 1H). LRMS: m/z ($ES^+$) 440 [$MH^+$]

Preparation 35

(2EZ)-4-(4-Methoxybenzyl)-2-[(1-propyl-1H-imidazol-4-yl)methylidene]-3-morpholinone

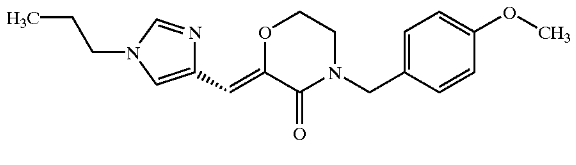

Triethylamine (9.19 ml, 65.9 mmol) was added to a solution of the alcohol of Preparation 23 (15.8 g, 44.0 mmol) in dichloromethane (300 ml). The solution was cooled in ice, methanesulphonyl chloride (5.1 ml, 65.9 mmol) was added, and the solution was stirred for 2 hours at room temperature. Additional triethylamine (3.06 ml, 22 mmol) was added, and the mixture was stirred at 40° C. for 18 hours then cooled. The mixture was diluted with dichloromethane (1000 ml) and washed with sodium bicarbonate solution (200 ml). The aqueous wash was extracted with dichloromethane (400 ml), and the combined organic solutions were dried ($MgSO_4$) and evaporated under reduced pressure. The residue was purified by column chromatography on silica gel using an elution gradient of ethyl acetate:dichloromethane:methanol:0.88 ammonia (100:0:0:0 to 0:95:5:0.5 to 0:90:10:1) to afford the title compound, 8.3 g. $^1$H-NMR ($CDCl_3$, 400 MHz) (mixture of geometric isomers) δ: 0.90 (t, 3H), 1.78 (m, 2H), 3.39 (t, 2H), 3.77 (s, 3H), 3.83 (t, 2H), 4.15 (t, 2H), 4.61 (s, 2H), 6.81 (d, 2H), 7.00 (s, 1H), 7.19 (d, 2H), 7.28 (s, 1H), 7.41 (s, 1H). LRMS: m/z ($ES^+$) 342 [$MH^+$]

Preparation 36

(2EZ)-4-(4-Methoxybenzyl)-2-[(1-trityl-1H-imidazol-4-yl)methylidene]-3-morpholinone

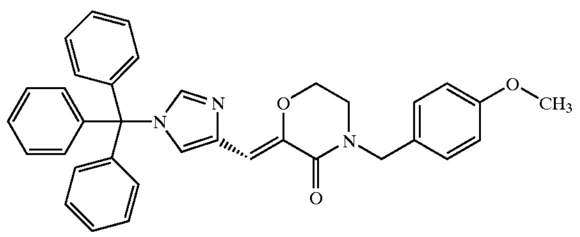

The title compound was obtained in 77% yield as a yellow foam from the alcohol of Preparation 28 following the procedure described in Preparation 35. $^1$H-NMR ($CDCl_3$, 400 MHz) (mixture of geometric isomers) δ: 3.34 (t, 2H), 3.78 (s, 3H), 4.00 (t, 2H), 4.59 (s, 2H), 6.80 (d, 2H), 6.98 (s, 1H), 7.10 (m, 6H), 7.17 (d, 2H), 7.28 (m, 10H), 7.39 (s, 1H). LRMS: m/z ($ES^+$) 542 [$MH^+$]

Preparation 37

(2EZ,6R)-4-(4-Methoxybenzyl)-6-methyl-2-[(1-trityl-1H-imidazol-4-yl)methylidene]-3-morpholinone

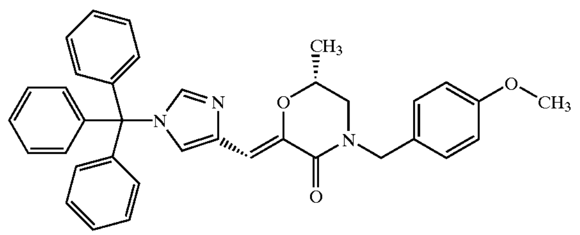

The title compound was obtained in 57% yield as a pale yellow foam, from the alcohol of Preparation 29, following the procedure described in Preparation 35. $^1$H-NMR ($CDCl_3$, 400 MHz) (mixture of geometric isomers) δ: 1.02 (d, 3H), 3.08 (dd, 1H), 3.20 (dd, 1H), 3.77 (s, 3H), 4.10 (m, 1H), 4.50 (d, 1H), 4.60 (d, 1H), 6.80 (d, 2H), 6.99 (s, 1H), 7.14 (m, 8H), 7.28 (m, 10H), 7.38 (s, 1H). LRMS: m/z ($ES^+$) 556 [$MH^+$]

Preparation 38

(2EZ,6S)-4-(4-Methoxybenzyl)-6-methyl-2-[(1-trityl-1H-imidazol-4-yl)methylidene]-3-morpholinone

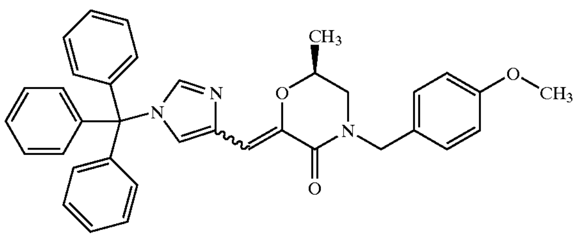

Methanesulphonyl chloride (911 μl, 11.78 mmol) was added dropwise to an ice-cooled solution of the alcohol of Preparation 30 (4.5 g, 7.85 mmol) in dichloromethane (40 ml) and triethylamine (1.64 ml, 11.78 mmol), and the solution was stirred at room temperature for 1 hour. Additional triethylamine (546 μl, 3.93 mmol) was added, and the mixture was stirred at 40° C. for 18 hours. The cooled mixture was partitioned between dichloromethane (50 ml) and water (50 ml) and the layers were separated. The organic phase was dried ($MgSO_4$) and concentrated under reduced pressure. The residual orange oil was purified by column chromatography on silica gel using an elution gradient of dichloromethane:methanol:0.88 ammonia (99:1:0.1 to 98:2:0.2) to afford the title compound as a yellow foam, 2.5 g. $^1$H-NMR ($CDCl_3$, 400 MHz) (mixture of geometric isomers) δ: 1.02 (d, 3H), 3.05 (m, 1H), 3.20 (m, 1H), 3.78 (s, 3H), 4.06 (m, 1H), 4.47–4.63 (m, 2H), 6.80 (d, 2H), 6.98 (s, 1H), 7.12 (m, 8H), 7.27 (m, 10H), 7.38 (s, 1H). LRMS: m/z ($ES^+$) 556 [$MH^+$]

Preparation 39

(2EZ,5S)-4-(4-Methoxybenzyl)-5-methyl-2-[(1-trityl-1H-imidazol-4-yl)methylidene]-3-morpholinone

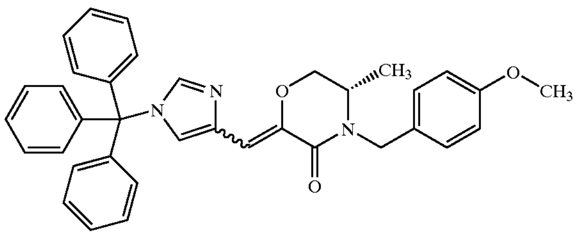

The title compound was obtained in 28% yield from the alcohol of Preparation 31 following a similar procedure to that described in Preparation 38. $^1$H-NMR ($CDCl_3$, 400 MHz) (mixture of geometric isomers) δ: 1.22 (d, 3H), 3.38 (m, 1H), 3.78 (s, 3H), 3.81 (d, 1H), 3.95 (m, 2H), 5.28 (d, 1H), 6.80 (d, 2H), 6.95 (s, 1H), 7.10–7.19 (m, 9H), 7.28 (m, 9H), 7.40 (s, 1H).

Preparation 40

(2EZ,5R)-4-(4-Methoxybenzyl)-5-methyl-2-[(1-trityl-1H-imidazol-4-yl)methylidene]-3-morpholinone

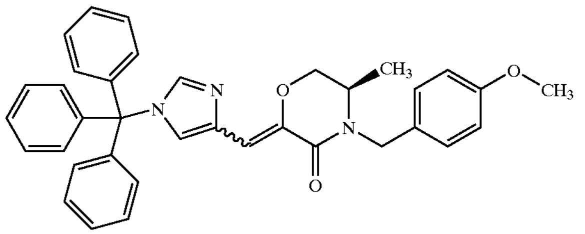

The title compound was obtained in 27% yield from the alcohol of Preparation 32 following a similar procedure to that described in Preparation 38. $^{1}$H-NMR ($CDCl_3$, 400 MHz) (mixture of geometric isomers) δ: 1.25 (d, 3H), 3.41 (m, 1H), 3.78 (s, 3H), 3.83 (dd, 1H), 3.98 (m, 2H), 5.30 (d, 1H), 6.82 (d, 2H), 6.98 (s, 1H), 7.18 (m, 9H), 7.32 (m, 9H), 7.41 (s, 1H).

Preparation 41

(2EZ)-2-[(1-Butyl-1H-imidazol-4-yl)methylidene]-4-(4-methoxybenzyl)-3-morpholinone

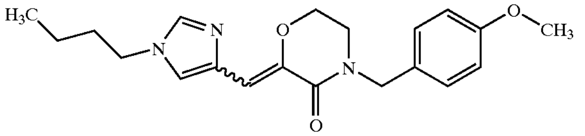

Triethylamine (1.78 ml, 12.8 mmol) was added to a solution of the alcohol of Preparation 25 (4.34 g, 11.6 mmol) in dichloromethane (50 ml). The solution was cooled in ice and methanesulphonyl chloride (990 μl, 12.8 mmol) was added. The solution was stirred for 30 minutes, additional triethylamine (1.78 ml, 12.8 mmol) added, and the mixture was stirred at room temperature for 18 hours. The mixture was concentrated under reduced pressure and the residue was purified by column chromatography on silica gel using an elution gradient of dichloromethane:ethyl acetate:methanol (100:0:0 to 0:90:10) to afford the title compound as a sticky gum, 1.12 g. $^{1}$H-NMR ($CDCl_3$, 400 MHz) (mixture of geometric isomers) □δ:0.95 (t, 3H), 1.34 (m, 2H), 1.78 (m, 2H), 3.42 (t, 2H), 3.80 (s, 3H), 3.94 (t, 2H), 4.19 (t, 2H), 4.63 (s, 2H), 6.84 (d, 2H), 7.02 (s, 1H), 7.22 (d, 2H), 7.32 (s, 1H), 7.44 (s, 1H). LRMS: m/z ($TSP^+$) 356.2 [$MH^+$]

Preparation 42

(2EZ)-2-{[1-(2-Cyclohexylethyl)-1H-imidazol-4-yl]methylidene}-4-(4-methoxybenzyl)-3-morpholinone

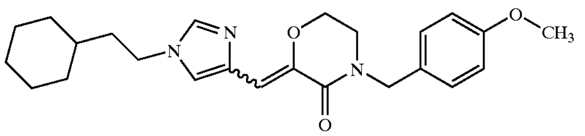

The title compound was obtained as a sticky gum in 57% yield from the alcohol of Preparation 26 following the procedure described in Preparation 41. $^{1}$H-NMR ($CDCl_3$, 400 MHz) (mixture of geometric isomers) δ: 0.94 (m, 2H), 1.18 (m, 4H), 1.64 (m, 7H), 3.40 (t, 2H), 3.78 (s, 3H), 3.90 (t, 2H), 4.17 (t, 2H), 4.61 (s, 2H), 6.81 (d, 2H), 6.99 (s, 1H), 7.20 (d, 2H), 7.25 (s, 1H), 7.40 (s, 1H). LRMS: m/z ($TSP^+$) 410.1 [$MH^+$]

Preparation 43

(2EZ)-4-(4-Methoxybenzyl)-2-{[1-(2-phenylethyl)-1H-imidazol-4-yl]methylidene}-3-morpholinone

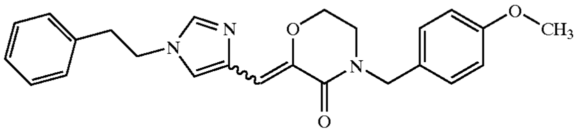

Triethylamine (0.98 ml, 7.03 mmol) was added to a solution of the alcohol of Preparation 27 (1.41 g, 3.35 mmol) in dichloromethane (15 ml). The solution was cooled in ice, methanesulphonyl chloride (311 μl, 4.02 mmol) was added, and the mixture was warmed to 40° C. and stirred for 18 hours, then concentrated under reduced pressure. The residue was purified by column chromatography on silica gel using an elution gradient of pentane:ethyl acetate:methanol (75:25:0 to 0:100:0 to 0:95:5) to afford the title compound as an orange oil, 449 mg. $^{1}$H-NMR ($CDCl_3$, 400 MHz) (mixture of geometric isomers) δ:3.03 (t, 2H), 3.42 (t, 2H), 3.80 (s, 3H), 4.18 (m, 4H), 4.63 (s, 2H), 6.85 (d, 2H), 7.02 (s, 1H), 7.06 (d, 2H), 7.25 (m, 7H). LRMS: m/z ($ES^+$) 404 [$MH^+$]

Preparation 44 tert-Butyl (2EZ)-2-[2-(dimethylamino)ethoxy]-3-(1-propyl-1H-imidazol-4-yl)-2-propenoate

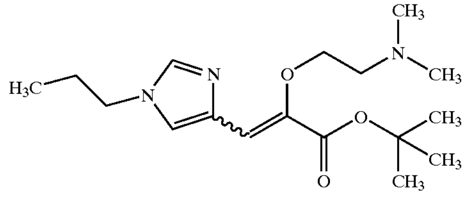

Methanesulphonyl chloride (340 μl, 4.4 mmol) was added dropwise to an ice-cooled solution of the alcohol of Preparation 33 (1.36 g, 4.0 mmol) and triethylamine (616 μl, 4.4 mmol) in dichloromethane (20 ml). The solution was stirred at room temperature for 1 hour, additional triethylamine (616 μl, 4.4 mmol) was added, and the solution was stirred at room temperature for 18 hours. TLC analysis showed starting material remaining, so the solution was heated to reflux and stirred for a further 3 hours. The cooled mixture was pre-adsorbed onto silica gel and purified by column chromatography on silica gel using an elution gradient of ethyl acetate:diethylamine:methanol (100:0:0 to 96:2:2) to afford the title compound, 650 mg. $^{1}$H-NMR ($CDCl_3$, 400 MHz) (mixture of geometric isomers) δ:0.98 (t, 3H), 1.56 (s, 9H), 1.84 (m, 2H), 2.34 (s, 6H), 2.65 (t, 2H), 3.94 (t, 2H), 4.04 (t, 2H), 7.08 (s, 1H), 7.44 (s, 1H), 7.98 (s, 1H). LRMS: m/z ($TSP^+$) 324.2 [$MH^+$]

Preparation 45 tert-Butyl (3S)-3-{[(EZ)-1-(tert-butoxycarbonyl)-2-(1-propyl-1H-imidazol-4-yl)ethenyl]oxy}pyrrolidine-1-carboxylate

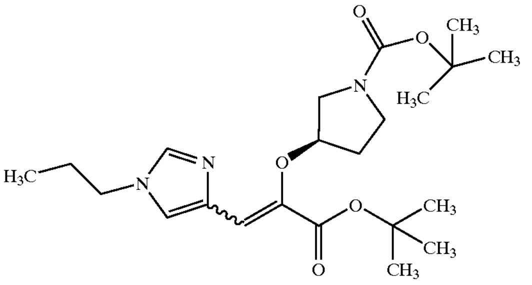

The title compound was obtained as an orange oil in 36% yield from the alcohol of Preparation 34 following the procedure described in Preparation 44. $^{1}$H-NMR ($CDCl_3$, 400MHz) (mixture of geometric isomers) δ:0.93 (t, 3H), 1.35–1.56 (m, 18H), 1.80 (m, 2H), 1.98 (m, 1H), 2.17 (m, 1H), 3.26–3.66 (m, 4H), 3.86 (m, 2H), 5.15 (m, 1H), 7.06, 7.15 (2×s, 1H), 7.35, 7.39 (2×s, 1H), 7.41 (s, 1H). LRMS: m/z ($ES^+$) 422 [$MH^+$]

Preparation 46

(2EZ)-4-Methyl-2-[(1-propyl-1H-imidazol-4-yl)methylidene]-3-morpholinone

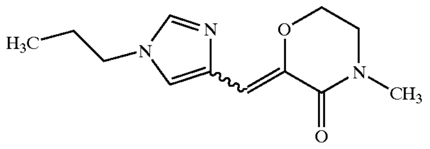

Triethylamine (3.32 ml, 23.8 mmol) was added to a solution of the alcohol of Preparation 24 (5.47 g, 21.6 mmol) in dichloromethane (80 ml), and the solution was cooled in ice. A solution of methanesulphonyl chloride (1.84 ml, 23.8 mmol) in dichloromethane (3 ml) was added over 5 minutes, and the solution was stirred at room temperature for 1 hour. The mixture was evaporated under reduced pressure, the residue was dissolved in N,N-dimethylformamide (15 ml), triethylamine (3.32 ml, 23.8 mmol) was added, and the solution was heated at reflux and stirred for 20 minutes. The cooled solution was concentrated under reduced pressure and the residue was dissolved in methanol (100 ml) then adsorbed onto silica gel and purified by column chromatography on silica gel using an elution gradient of ethyl acetate:methanol:diethylamine (100:0:0 to 95:5:0.5) to afford the title compound, 2.5 g. $^{1}$H-NMR ($CDCl_3$, 400 MHz) (mixture of geometric isomers) δ:0.98 (t, 3H), 1.82 (m, 2H), 3.14 (s, 3H), 3.59 (t, 2H), 3.90 (t, 2H), 4.26 (t, 2H), 7.00 (s, 1H), 7.35 (s, 1H), 7.45 (s, 1H). LRMS: m/z ($TSP^+$) 236.2 [$MH^+$]

Preparation 47

(−)-(2S)-4-(4-Methoxybenzyl)-2-[(1-propyl-1H-imidazol-4-yl)methyl]-3-morpholinone

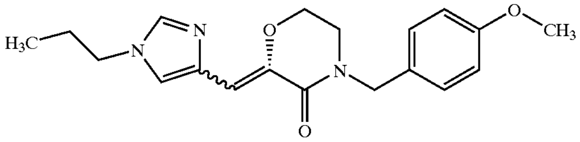

A mixture of the alkene of Preparation 35 (8.3 g, 24.3 mmol) and 10% Pd/C (Degussa® 101) (800 mg) in ethanol (240 ml) was hydrogenated at 100 psi (690 kPa) and 50° C. for 18 hours, then cooled and filtered through Arbocel®. The filtrate was evaporated under reduced pressure to give an orange oil. This product was purified by column chromatography on a Chiralcel® OJ column, using hexane: isopropyl alcohol:diethylamine (70:30:0.5) as eluant, to afford enantiomer 1, 1.65 g, followed by enantiomer 2, the title compound, 1.54 g. $^{1}$H-NMR ($CDCl_3$, 400 MHz) δ:0.92 (t, 3H), 1.78 (m, 2H), 3.07 (m, 2H), 3.38 (m, 2H), 3.74 (m, 1H), 3.79 (m, 5H), 3.98 (m, 1H), 4.52 (m, 3H), 6.72 (s, 1H), 6.82 (d, 2H), 7.18 (d, 2H), 7.38 (s, 1H). LRMS: m/z ($ES^+$) 344 [$MH^+$]. $[\alpha]_D$=−66.10, (c=0.368, methanol)

Preparation 48

(2RS)-2-[(1-Butyl-1H-imidazol-4-yl)methyl]-4-(4-methoxybenzyl)-3-morpholinone

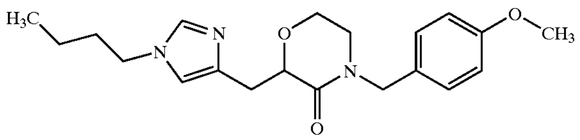

A mixture of the alkene of Preparation 41 (2.5 g, 6.96 mmol) and 10% Pd/C (Degussa® 101) (250 mg) in ethanol (100 ml) was hydrogenated at 50° C. and 60 psi (410 kPa) for 18 hours. The cooled mixture was filtered through Arbocel® and the filtrate was evaporated under reduced pressure to afford the title compound as an oil, 2.44 g. $^{1}$H-NMR ($CDCl_3$, 400 MHz) δ:0.95 (t, 3H), 1.32 (m, 2H), 1.73 (m, 2H), 3.04 (m, 2H), 3.34–3.42 (m, 2H), 3.73 (m, 1H), 3.78 (s, 3H), 3.82 (t, 2H), 3.98 (m, 1H), 4.45–4.60 (m, 3H), 6.74 (s, 1H), 6.82 (d, 2H), 7.18 (d, 2H), 7.38 (s, 1H). LRMS: m/z ($TSP^+$) 358.2 [$MH^+$].

Preparations 49 to 50

The compounds of the following general formula

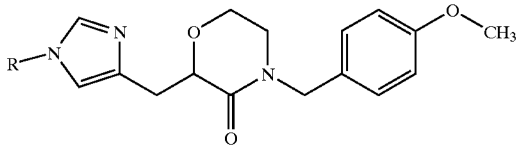

were prepared from the appropriate alkene (Preparations 42 and 43), following a similar procedure to that described in Preparation 48.

| Prep. No. | R | Yield (%) | Data |
|---|---|---|---|
| 49[1] | 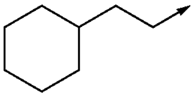 | 75, sticky gum | $^1$H-NMR($CDCl_3$, 400MHz) δ: 0.96(m, 2H), 1.20 (m, 4H), 1.68(m, 7H), 3.04(m, 2H), 3.40(m, 2H), 3.74(m, 1H), 3.80(s,3H), 3.86(s, 3H), 3.98(m, 1H), 4.55(m, 2H), 6.74(s, 1H), 6.84 (d, 2H), 7.18(d, 2H), 7.38(s, 1H). LRMS: m/z(TSP$^+$) 412.2[MH$^+$] |
| 50 | 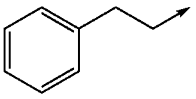 | 91 orange oil | $^1$H-NMR($CDCl_3$, 400MHz) δ: 3.00–3.10(m, 4H), 3.35(dd, 1H), 3.40(dd, 1H), 3.70(m, 1H), 3.79(s, 3H), 3.98(m, 1H), 4.08(t, 2H), 4.45(m, 1H), 4.55(m, 2H), 6.69(s, 1H), 6.68(d, 2H), 7.06(d, 2H), 7.18(d, 2H), 7.25(m, 4H). LRMS: m/z(ES$^+$) 406[MH$^+$] |

[1]purified by column chromatography on silica gel using an elution gradient of ethyl acetate:methanol(100:0 to 90:10)

Preparation 51

(2RS)-4-Methyl-2-[(1-propyl-1H-imidazol-4-yl)methyl]-3-morpholinone

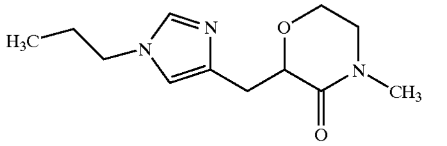

A mixture of the alkene of Preparation 46 (2.5 g, 1.06 mmol) and 10% Pd/C (Degussa® 101) (250 mg) in ethanol (50 ml) was hydrogenated at 50° C. and 60 psi (410 kPa) for 18 hours. The cooled mixture was filtered through Arbocel® and the filtrate was evaporated under reduced pressure. The residue was purified by column chromatography on silica gel using an elution gradient of ethyl acetate:methanol:diethylamine (100:0:0 to 96.5:1.75:1.75) to afford the title compound as a colourless oil, 2.08 g. $^1$H-NMR ($CDCl_3$, 400 MHz) δ:0.95 (t, 3H), 1.80 (m, 2H), 3.00 (m, 4H), 3.18 (m, 1H), 3.37 (m, 1H), 3.57 (m, 1H), 3.82 (m, 3H), 4.03 (m, 1H), 4.46 (dd, 1H), 6.78 (s, 1H), 7.39 (s, 1H). LRMS: m/z (ES$^+$) 238 [MH$^+$]

Preparation 52

(2RS)-2-[(1H-Imidazol-4-yl)methyl]-4-(4-methoxybenzyl)-3-morpholinone

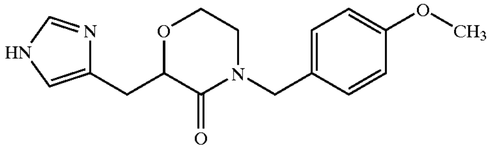

A mixture of the protected imidazole of Preparation 36 (25 g, 46 mmol) and Pd/C Degussa® 101 catalyst (2.5 g) in ethanol (500 ml) was hydrogenated at 50° C. and 60 psi (410 kPa) for 18 hours. TLC analysis showed starting material remaining, so the mixture was filtered through Arbocel® and the filtrate was hydrogenated using fresh catalyst (2.5 g) in ethanol (500 ml) at 50° C. and 60 psi (410 kPa) for a further 18 hours. The mixture was filtered through Arbocel® and the filtrate was evaporated under reduced pressure. The product was purified by column chromatography on silica gel using an elution gradient of dichloromethane:methanol:0.88 ammonia (98:2:0.2 to 95:5:0.5) to afford the title compound as a white foam, 9 g. $^1$H-NMR ($CDCl_3$, 400 MHz) δ:3.01 (m, 1H), 3.18 (m, 2H), 3.38 (m, 1H), 3.70 (dd, 1H), 3.78 (s, 3H), 3.97 (dd, 1H), 4.32 (m, 1H), 4.50 (dd, 2H), 6.81 (d, 2H), 6.86 (s, 1H), 7.02 (d, 2H), 7.46 (s, 1H). LRMS: m/z (ES$^+$) 302 [MH$^+$]

Preparation 53

(−)-(2S)-2-[(1H-Imidazol-4-yl)methyl]-4-(4-methoxybenzyl)-3-morpholinone and

Preparation 54

(+)-(2R)-2-[(1H-Imidazol-4-yl)methyl]-4-(4-methoxybenzyl)-3-morpholinone

The racemic compound of Preparation 52 was further purified by HPLC using a Chiralpak® OD column, and hexane:isopropyl alcohol (80:20) as eluant to afford the title compound of preparation 53, >99% ee. $^1$H-NMR ($CDCl_3$, 400 MHz) δ:3.01 (m, 1H), 3.18 (m, 2H), 3.38 (m, 1H), 3.70 (dd, 1H), 3.78 (s, 3H), 3.97 (dd, 1H), 4.32 (m, 1H), 4.50 (dd, 2H), 6.81 (d, 2H), 6.86 (s, 1H), 7.02 (d, 2H), 7.46 (s, 1H). LRMS: m/z (ES$^+$) 324 [MNa$^+$]. $[\alpha]_D$=−529.3 (c=0.05, methanol).

Further elution gave the title compound of preparation 54, >99% ee. $^1$H-NMR ($CDCl_3$, 400 MHz) δ: 3.01 (m, 1H), 3.18 (m, 2H), 3.38 (m, 1H), 3.66–3.79 (m, 4H), 3.97 (dd, 1H), 4.32 (t, 1H), 4.50 (dd, 2H), 6.81 (d, 2H), 6.86 (s, 1H), 7.02 (d, 2H), 7.46 (s, 1H). LRMS: m/z (ES$^+$) 324 [MNa$^+$]

Preparation 55a (2S,6R)-2-[(1H-Imidazol-4-yl)methyl]-4-(4-methoxybenzyl)-6-methyl-3-morpholinone and Preparation 55b (2R,6R)-2-[(1H-Imidazol-4-yl)methyl]-4-(4-methoxybenzyl)-6-methyl-3-morpholinone

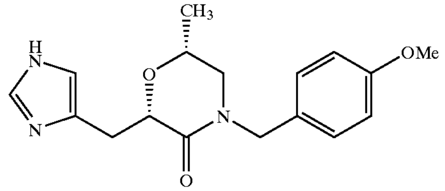

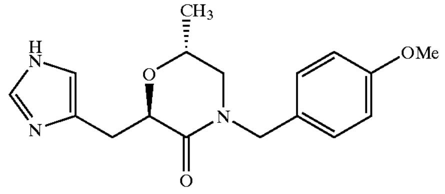

A mixture of the alkene of Preparation 154 (41 g, 131 mmol) and 10% palladium on carbon (Degussa type 101) (8 g) in ethanol (500 ml) was hydrogenated at 50 psi (345 kPa) and 60° C. for 24 hours. The mixture was filtered through Arbocel®, the filtrate was concentrated under reduced pressure and the residue was azeotroped with dichloromethane. The crude product was purified by column chromatography on silica gel using a Biotage column, eluting with a solvent gradient of dichloromethane:methanol:0.88 ammonia (97.5:2.5:0.1 to 90:10:1). The higher running, major product was repurified by column chromatography on silica gel using dichloromethane:methanol:0.88 ammonia (95:5:0.25) to afford the title compound of preparation 55a as a white foam. $^1$H-NMR ($CDCl_3$, 400 MHz) δ: 1.19 (d, 3H), 2.97–3.22 (m, 4H), 3.78 (s, 3H), 3.84 (m, 1H), 4.32 (t, 1H), 4.40 (d, 1H), 4.50 (d, 1H), 6.80 (d, 2H), 6.86 (s, 1H), 7.00 (d, 2H), 7.46 (s, 1H). LRMS: m/z ($ES^-$) 314 $[M-H]^-$ The lower running, minor product was further purified by column chromatography on silica gel using ether:methanol:0.88 ammonia (90:10:1) as eluant and the product was azeotroped with dichloromethane to afford the title compound of preparation 55b as a white foam, 220 mg. $^1$H-NMR ($CDCl_3$, 400 MHz) δ: 1.19 (d, 3H), 2.97–3.22 (m, 4H), 3.78 (s, 3H), 3.84 (m, 1H), 4.32 (t, 1H), 4.40 (d, 1H), 4.50 (d, 1H), 6.80 (d, 2H), 6.86 (s, 1H), 7.00 (d, 2H), 7.46 (s, 1H).

Preparation 56

(2R,6S)-2-[(1H-Imidazol-4-yl)methyl]-4-(4-methoxybenzyl)-6-methyl-3-morpholinone

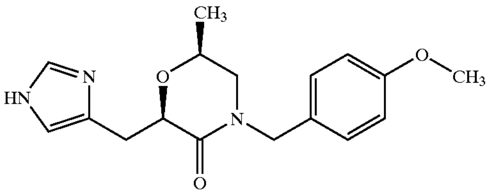

The title compound was obtained in 20% yield from the protected alkene of Preparation 38 following the procedure described in 52. $^1$H-NMR ($CDCl_3$, 400 MHz) δ: 1.19 (d, 3H), 2.99 (m, 2H), 3.17 (m, 2H), 3.78 (s, 3H), 3.83 (m, 1H), 4.30 (m, 1H), 4.44 (dd, 2H), 6.80 (d, 2H), 6.85 (s, 1H), 7.00 (d, 2H), 7.45 (s, 1H). LRMS: m/z ($ES^+$) 316 $[MH]^+$ Preparation 57

(2S,5S)-2-[(1H-Imidazol-4-yl)methyl]-4-(4-methoxybenzyl)-5-methyl-3-morpholinone

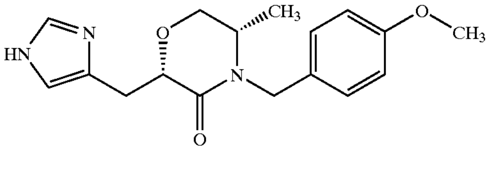

The title compound was obtained in 47% yield from the protected alkene of Preparation 39 following a similar procedure to that described in Preparation 52. $^1$H-NMR ($CDCl_3$, 400 MHz) (3:1 mixture of depicted C-2 stereoisomer) δ:1.15 (d, 3H), 3.22 (m, 3H), 3.48, 3.70–4.00 (2×m, 6H), 4.38 (m, 1H), 5.18–5.37 (m, 1H), 6.83 (d, 2H), 6.98 (m, 1H), 7.18 (d, 2H), 7.62 (s, 1H). LRMS: m/z ($ES^-$) 314 [M−H]

Preparation 58

(2R,5R)-2-[(1H-Imidazol-4-yl)methyl]-4-(4-methoxybenzyl)-5-methyl-3-morpholinone

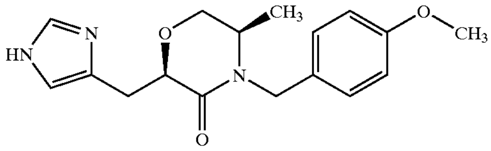

The title compound was obtained in 67% yield from the protected imidazole of Preparation 40 following a similar procedure to that described in Preparation 52. $^1$H-NMR ($CDCl_3$, 400 MHz) (3:1 mixture of depicted C-2 stereoisomer) δ:1.16 (d, 3H), 3.22 (m, 3H), 3.46, 3.70–3.98 (2×m, 6H), 4.35, 4.39 (2×m, 1H), 5.20, 5.30 (2×d, 1H), 6.82, 6.94 (2×m, 3H), 7.18 (d, 2H), 7.53 (2×s, 1H). LRMS: m/z ($ES^-$) 314 $[M-H^-]$ Preparation 59

(2RS)-({1-[2-(4-Bromophenyl)ethyl]-1H-imidazol-4-yl}methyl)-4-(4-methoxybenzyl)-3-morpholinone

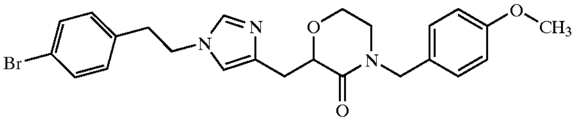

Sodium hydride (836 mg, 60% dispersion in mineral oil, 20.9 mmol) was added portionwise to an ice-cooled solution of the imidazole of Preparation 52 (5 g, 19.9 mol) in tetrahydrofuran (100 ml), and the solution was stirred for 15 minutes. 4-Bromophenylethyl methanesulphonate (*Bioorg. Med. Chem.* 1996; 4(5); 645) (6.1 g, 21.9 mmol) was then added, and the mixture was stirred at room temperature for 3 days. The reaction was quenched with water (50 ml), and the mixture was extracted with ethyl acetate (2×100 ml). The combined organic extracts were dried ($MgSO_4$) and evaporated under reduced pressure. The crude product was purified by column chromatography on silica gel using an elution gradient of dichloromethane:methanol:0.88 ammonia (99:1:0.1 to 95:5:0.5) to afford the title compound, 4.4 g. $^1$H-NMR ($CDCl_3$, 400 MHz) δ:2.97 (t, 2H), 3.04 (m, 2H), 3.36 (m, 2H), 3.70 (m, 1H), 3.78 (s, 3H), 3.97 (m, 1H), 4.03 (t, 2H), 4.45 (m, 1H), 4.54 (dd, 2H), 6.62 (s, 1H), 6.82 (d, 2H), 6.90 (d, 2H), 7.18 (d, 2H), 7.20 (s, 1H), 7.39 (d, 2H).

Preparation 60

(−)-(2S)-2-{[1-(2-Cyclohexylethyl)-1H-imidazol-4-yl]methyl}-4-(4-methoxybenzyl)-3-morpholinone

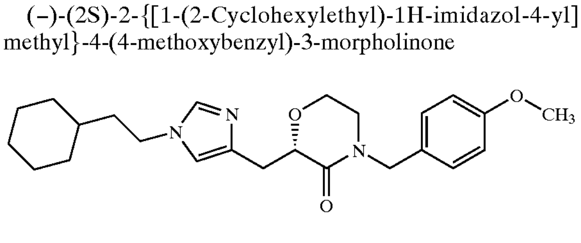

A mixture of the compound of Preparation 53 (400 mg, 1.32 mmol), cesium carbonate (472 mg, 1.45 mmol), and 2-cyclohexylethyl bromide (227 μl, 1.45 mmol) in N,N-dimethylformamide (4 ml) was stirred at 80° C. for 18 hours. The cooled mixture was partitioned between ethyl acetate (250 ml) and water (100 ml), and the layers were separated. The organic phase washed with water (3x100 ml), dried ($MgSO_4$) and evaporated under reduced pressure. The crude product was purified twice by column chromatography on silica gel using first an elution gradient of dichloromethane:methanol:0.88 ammonia (100:0:0 to 95:5:0.5), then using an elution gradient of ethyl acetate:diethylamine (100:0 to 95:5), to afford the title compound, as a colourless gum, 191 mg. $^1$H-NMR ($CDCl_3$, 400 MHz) δ: 0.90 (m, 2H), 1.04–1.24 (m, 4H), 1.60 (m, 7H), 3.02 (m, 2H), 3.26–3.40 (m, 2H), 3.70 (m, 1H), 3.78 (s, 3H), 3.81 (t, 2H), 3.97 (m, 1H), 4.42–4.58 (m, 3H), 6.68 (s, 1H), 6.80 (d, 2H), 7.14 (d, 2H), 7.35 (s, 1H). LRMS: m/z ($ES^+$) 412 [$MH^+$]. $[\alpha]_D$=−50.37, (c=0.112 in methanol)

Preparation 61

(2R,6S)-2-{[1-(2-Cyclohexylethyl)-1H-imidazol-4-yl]methyl}-4-(4-methoxybenzyl)-6-methyl-3-morpholinone

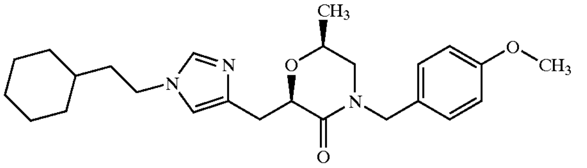

A mixture of the compound of Preparation 56 (200 mg, 0.635 mmol), cesium carbonate (248 mg, 0.762 mmol) and 2-cyclohexylethyl bromide (109 μl, 0.70 mmol) in N,N-dimethylformamide (8 ml) was stirred at 70° C. for 18 hours. The cooled mixture was partitioned between ethyl acetate (10 ml) and water (10 ml), and the layers were separated. The organic phase washed with water (2x20 ml) and brine (20 ml), then dried ($MgSO_4$) and evaporated under reduced pressure. The crude product was purified by column chromatography on silica gel using an elution gradient of dichloromethane:methanol:0.88 ammonia (99:1:0.1 to 98:2:0.2) to afford the title compound as a colourless gum, 120 mg. $^1$H-NMR ($CDCl_3$, 400 MHz) δ: 0.90 (m, 2H), 1.18 (m, 7H), 1.62 (m, 7H), 2.94–3.08 (m, 3H), 3.32 (dd, 1H), 3.78 (s, 3H), 3.80 (m, 3H), 4.43 (m, 3H), 6.66 (s, 1H), 6.80 (d, 2H), 7.14 (d, 2H), 7.32 (s, 1H). LRMS: m/z ($ES^+$) 426 [$MH^+$]

Preparation 62

(2S,6R)-2-{[1-(2-Cyclohexylethyl)-1H-imidazol-4-yl]methyl}-4-(4-methoxybenzyl)-6-methyl-3-morpholinone

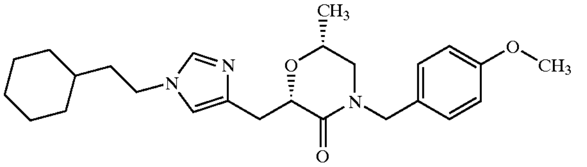

The title compound was obtained as a colourless oil in 38% yield from the imidazole of Preparation 55 and 2-cyclohexylethyl bromide following the procedure described in Preparation 61. $^1$H-NMR ($CDCl_3$, 400 MHz) δ: 0.90 (m, 2H), 1.17 (m, 7H), 1.61 (m, 7H), 2.94–3.08 (m, 3H), 3.32 (dd, 1H), 3.78 (s, 3H), 3.81 (m, 3H), 4.43 (m, 3H), 6.66 (s, 1H), 6.80 (d, 2H), 7.12 (d, 2H), 7.32 (s, 1H). LRMS: m/z ($ES^+$) 448 [$MNa^+$]

Preparation 63

(2S,5S)-2-{[1-(2-Cyclohexylethyl)-1H-imidazol-4-yl]methyl}-4-(4-methoxybenzyl)-5-methyl-3-morpholinone

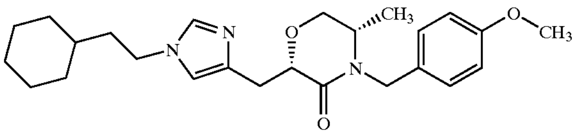

The title compound was obtained in 21% yield from the imidazole of Preparation 57 following a similar procedure to that described in Preparation 61, except that ethyl acetate:methanol:diethylamine (98:1:1) was used as the column eluant. $^1$H-NMR ($CDCl_3$, 400MHz) (mixture of C-2 diastereoisomers) δ: 0.98 (m, 2H), 1.20 (m, 7H), 1.68 (m, 7H), 3.05–3.98 (m, 11H), 4.50 (m, 1H), 5.22–5.40 (m, 1H), 6.76, 6.84 (s and m, 3H), 7.14, 7.20 (2xd, 2H), 7.39 (m, 1H). LRMS: m/z ($ES^+$) 426 [$MH^+$]

Preparation 64

(2R,5R)-2-{[1-(2-Cyclohexylethyl)-1H-imidazol-4-yl]methyl}-4-(4-methoxybenzyl)-5-methyl-3-morpholinone

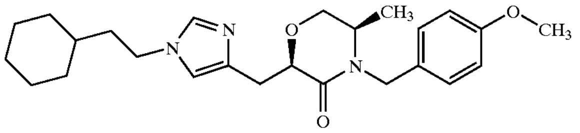

The title compound was obtained in 40% yield from the imidazole of Preparation 58 following a similar procedure to that described in Preparation 61. $^1$H-NMR ($CDCl_3$, 400 MHz) (mixture of C-2 diastereoisomers) δ: 0.90 (m, 2H), 1.18 (m, 7H), 1.63 (m, 7H), 3.01–3.33 (m, 3H), 3.61–3.90 (m, 8H), 4.42 (m, 1H), 5.22 (m, 1H), 6.72 (s, 1H), 6.80 (d, 2H), 7.16 (d, 2H), 7.35 (s, 1H). LRMS: m/z ($ES^+$) 426 [$MH^+$]

Preparation 65

(2S,6R)-2-{[1-(3-Cyclohexyl-3-methylbutyl)-1H-imidazol-4-yl]methyl}-4-(4-methoxybenzyl)-6-methyl-3-morpholinone

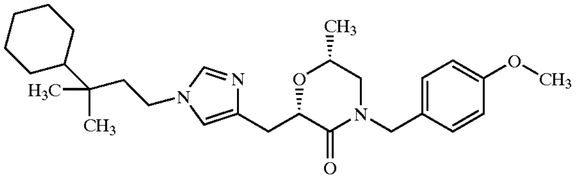

A mixture of the bromide of Preparation 21 (420 mg, 1.8 mmol), the imidazole of Preparation 55 (470 mg, 1.5 mmol) and cesium carbonate (586 mg, 1.8 mmol) in N,N-dimethylformamide (5mi) was stirred at 70° C. for 18 hours. The cooled mixture was concentrated under reduced pressure and partitioned between ethyl acetate (20 ml) and water (20 ml) and the layers were separated. The aqueous phase was extracted with ethyl acetate (3x15 ml), and the combined organic solutions were washed with brine (15 ml), dried ($MgSO_4$) and evaporated under reduced pressure. The crude product was purified by column chromatography using a Biotage® silica column and toluene:diethylamine (99:1 to 85:15) as eluant to afford the title compound, 60 mg. $^{1}$H-NMR ($CDCl_3$, 400 MHz) δ: 0.82 (s, 6H), 0.90–1.10 (m, 8H), 1.63 (m, 3H), 1.78 (m, 5H), 2.94–3.06 (m, 3H), 3.30 (dd, 1H), 3.79 (m, 6H), 4.40–4.55 (m, 3H), 6.68 (s, 1H), 6.80 (d, 2H), 7.10 (d, 2H), 7.32 (s, 1H). LRMS: m/z ($ES^+$) 468 [$MH^+$]

Preparation 66

(2S,6R)-2-({1-[2-(4,4-Dimethylcyclohexyl)ethyl]-1H-imidazol-4-yl}methyl)-4-(4-methoxybenzyl)-6-methyl-3-morpholinone

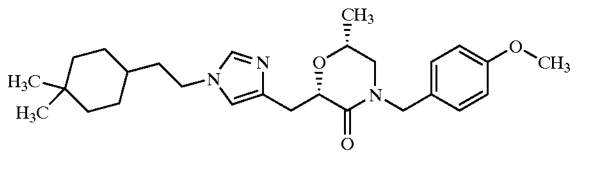

The title compound was obtained in 10% yield from the bromide of Preparation 22 and the imidazole of Preparation 55 following a similar procedure to that described in Preparation 65. $^{1}$H-NMR ($CDCl_3$, 400 MHz) δ: 0.84 (2×s, 6H), 1.16 (m, 8H), 1.37 (m, 2H), 1.50 (m, 2H), 1.63 (m, 2H), 2.97–3.10 (m, 3H), 3.35 (dd, 1H), 3.79 (s, 3H), 3.85 (m, 3H), 4.48 (m, 3H), 6.70 (s, 1H), 6.82 (d, 2H), 7.16 (d, 2H), 7.35 (s, 1H). LRMS: m/z ($ES^+$) 454 [$MH^+$]

Preparation 67

(2RS)-2-({1-[(2EZ)-3-Bromo-2-propenyl]-1H-imidazol-4-yl}methyl)-4-(4-methoxybenzyl)-3-morpholinone

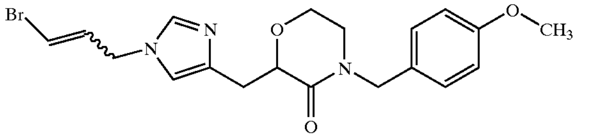

Sodium hydride (133 mg, 60% dispersion in mineral oil, 3.32 mmol) was added to an ice-cooled solution of the morpholinone of Preparation 52 (1 g, 3.32 mmol) in tetrahydrofuran (10 ml). 1,3-Dibromo-1-propene (mixture of cis and trans) (332 μl, 3.32 mmol) was added dropwise over 5 minutes then the mixture was allowed to warm to room temperature and stirred for 2 hours. The mixture was partitioned between water (50 ml) and ethyl acetate (50 ml), and the phases were separated. The aqueous layer was extracted with ethyl acetate (10 ml), and the combined organic solutions were dried ($Na_2SO_4$) and evaporated under reduced pressure. The crude product was purified by column chromatography on silica gel using dichloromethane:methanol:0.88 ammonia (98:2:0.2) as eluant to afford the title compound as a colourless oil, 1.1 g. $^{1}$H-NMR ($CDCl_3$, 400 MHz) (mixture of geometric isomers) δ: 3.02 (m, 2H), 3.26–3.40 (m, 2H), 3.68 (m, 1H), 3.78 (s, 3H), 3.96 (m, 1H), 4.40 (d, 1H), 4.42–4.55 (m, 3H), 4.60 (m, 1H), 6.22 (m, 1H), 6.70 (2×s, 1H), 6.80 (m, 3H), 7.15 (m, 2H), 7.38 (2×s, 1H). LRMS: m/z ($ES^+$) 420, 422 [$MH^+$]

Preparation 68

(2RS)-4-(4-Methoxybenzyl)-2-[(1-phenyl-1H-imidazol-4-yl)methyl]-3-morpholinone

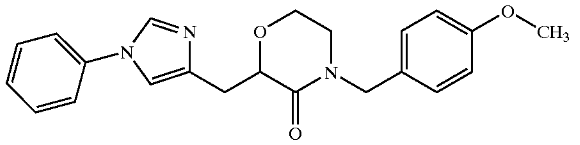

4 Å Molecular sieves, copper (II) acetate (452 mg, 2.49 mmol) and benzeneboronic acid (405 mg, 3.32 mmol) were added to a solution of the imidazole of Preparation 52 (500 mg, 1.66 mmol) and pyridine (269 μl, 3.32 mmol)in dichloromethane (20 ml), and the solution was stirred at room temperature for 18 hours. Compressed air was then bubbled through the solution for 10 hours. The solvent was retained by using a "cold finger". The solution was then stirred under a nitrogen atmosphere for a further 18 hours. A solution of ethylenediaminetetraacetic acid (800 mg) in saturated sodium bicarbonate solution (35 ml) was added and the mixture was stirred for 20 minutes, then extracted with dichloromethane (70 ml). The aqueous phase was further was extracted with dichloromethane (20 ml) and the combined organic solutions were washed with water (10 ml), dried ($MgSO_4$) and concentrated under reduced pressure. The residual black solid was purified by column chromatography on silica gel using an elution gradient of dichloromethane:methanol:0.88 ammonia (98:2:0.2 to 97:3:0.3) to afford the title compound as a pale yellow oil, 175 mg. $^{1}$H-NMR ($CDCl_3$, 400 MHz) δ: 3.02 (m, 1H), 3.18 (m, 1H), 3.38 (m, 2H), 3.70–3.79 (m, 4H), 3.99 (m, 1H), 4.42 (d, 1H), 4.50 (m, 1H), 4.60 (d, 1H), 6.77 (m, 2H), 7.10 (m, 3H), 7.32 (m, 3H), 7.41 (m, 2H), 7.78 (bs, 1H). LRMS: m/z ($ES^+$) 400 [$MNa^+$]

Preparation 69

(2RS)-2-{[1-(2-methylphenyl)-1H-imidazol-4-yl]methyl}-4-(4-Methoxybenzyl)-3-morpholinone

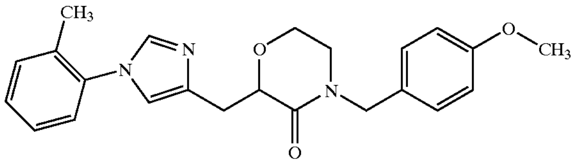

The title compound was obtained in 16% yield from the imidazole of Preparation 52 and 2-methylbenzeneboronic acid following the procedure described in Preparation 68. $^{1}$H-NMR ($CDCl_3$, 400 MHz) δ: 2.15 (s, 3H), 3.02 (m, 1H), 3.18 (m, 1H), 3.38 (m, 2H), 3.77 (m, 4H), 3.98 (m, 1H), 4.54 (m, 3H), 6.78 (d, 2H), 6.85 (bs, 1H), 7.15 (m, 3H), 7.21 (s, 1H), 7.25 (m, 2H), 7.45 (bs, 1H). LRMS: m/z ($TSP^+$) 470.2 [$MH^+$]

Preparation 70

(2RS)-2-{[1-(3-phenoxyphenyl)-1H-imidazol-4-yl]methyl}-4-(4-Methoxybenzyl)-3-morpholinone

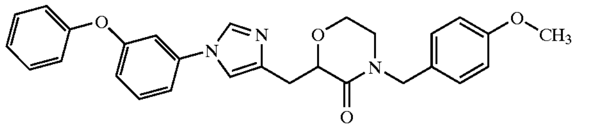

4Å Molecular sieves (50 mg), copper (II) acetate (174 mg, 0.96 mmol) and 3-phenoxyphenylboronic acid (*J. Chem. Soc.* 1970; 488) (350 mg, 1.6 mmol) were added to a solution of the imidazole of Preparation 52 (240 mg, 0.8 mmol) and pyridine (130 μl, 1.6 mmol) in dichloromethane (2 ml). Compressed air was then bubbled through the solution, maintained at 20–25° C. using a water bath, for 7 hours, and the solvent was retained by using a "cold finger". The solution was then stirred under a nitrogen atmosphere for a further 18 hours. The mixture was partitioned between dichloromethane (80 ml) and a solution of ethylenediaminetetraacetic acid tetrasodium salt (1 g) in saturated sodium bicarbonate solution (30 ml) and the phases were separated. The organic layer was dried ($MgSO_4$) and concentrated under reduced pressure. The residue was purified by column chromatography on silica gel using an elution gradient of ethyl acetate:diethylamine (100:0 to 95:5). The product was further purified by column chromatography using a Biotage® silica gel column, and an elution gradient of toluene:diethylamine (100:0 to 88:12) to afford the title compound as a pale yellow gum, 120 mg. $^1$H-NMR ($CDCl_3$, 400 MHz) δ: 3.01 (m, 1H), 3.15 (dd, 1H), 3.38 (m, 2H), 3.72 (m, 4H), 3.97 (m, 1H), 4.45 (d, 1H), 4.50 (m, 1H), 4.58 (d, 1H), 6.77 (d, 2H), 6.90 (m, 1H), 6.97 (m, 1H), 7.00–7.18 (m, 7H), 7.37 (m, 3H), 7.75 (s, 1H). LRMS m/z ($TSP^+$) 470.2 [$MH^+$]

Preparations 71 to 73

The following compounds of general structure

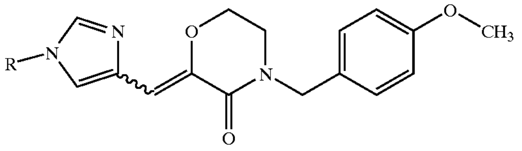

were prepared from the morpholinone of Preparation 52 and the appropriate boronic acids, following a similar procedure to that described in Preparation 70.

| Prep | R | Yield (%) | Data |
|---|---|---|---|
| 71 | 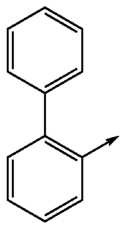 | 8 | $^1$H-NMR($CDCl_3$, 400MHz) δ: 3.00(m, 2H), 3.26(m, 2H), 3.62(m, 1H), 3.75(s, 3H), 3.90(m, 1H), 4.38(m, 1H), 4.48(s, 2H), 6.61(s, 1H), 6.78(d, 2H), 7.02(m, 2H), 7.14(d, 2H), 7.22(m, 4H), 7.30(m, 1H), 7.40(m, 3H). LRMS: m/z($ES^+$) 454[$MH^+$] |
| 72 | 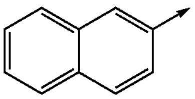 | 19 orange oil | $^1$H-NMR($CDCl_3$, 400MHz) δ: 3.06(m, 1H), 3.22(m, 1H), 3.41(m, 2H), 3.62(s, 3H), 3.79(m, 1H), 4.01(m, 1H), 4.46(d, 1H), 4.59(m, 1H), 4.62(d, 1H), 6.78(d, 2H), 7.15(d, 2H), 7.24(m, 1H), 7.50(m, 3H), 7.79(s, 1H), 7.84(dd, 1H), 7.95(m, 2H). LRMS: m/z($ES^+$) 450[$MNa^+$] |
| 73 | 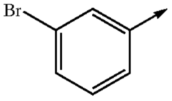 | 20 colourless oil | $^1$H-NMR($CDCl_3$, 400MHz) δ: 3.05(m, 1H), 3.18(dd, 1H), 3.40(m, 2H), 3.77(m, 4H), 4.00(m, 1H), 4.48(d, 1H), 4.55(m, 1H), 4.62(d, 1H), 6.80(d, 2H), 7.14(d, 2H), 7.21–7.37(m, 3H), 7.45(m, 1H), 7.54(s, 1H), 7.78(s, 1H). LRMS: m/z($TSP^+$) 457.7[$MH^+$] |

Preparations 74 to 76

The following compounds of general structure

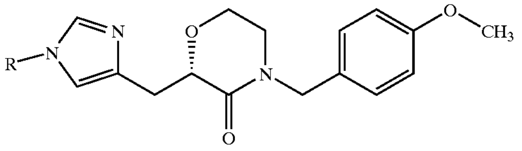

were prepared from the morpholinone of Preparation 53 and the appropriate boronic acids, following a similar procedure to that described in Preparation 70.

| Prep | R | Yield (%) | Data |
|---|---|---|---|
| 74 | 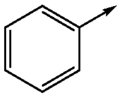 | 30 solid | $^1$H-NMR($CDCl_3$, 400MHz) δ: 3.02(m, 1H), 3.18(dd, 1H), 3.39(m, 2H), 3.72(m, 4H), 3.98(m, 1H), 4.43(d, 1H), 4.52(m, 1H), 4.60(d, 1H), 6.75(d, 2H), 7.10(m, 3H), 7.31(m, 3H), 7.42(dd, 2H), 7.78(s, 1H). LRMS: m/z(TSP$^+$) 378.1[MH$^+$]. $[\alpha]_D$ = −34.8, (c = 0.10, methanol) |
| 75 | 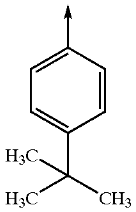 | 9 oil | $^1$H-NMR($CDCl_3$, 400MHz) δ: 1.37(s, 9H), 3.04(m, 1H), 3.19(dd, 1H), 3.40(m, 2H), 3.76(m, 4H), 4.00(m, 1H), 4.46(d, 1H), 4.58(m, 1H), 4.62(d, 1H), 6.78(d, 2H), 7.14(m, 3H), 7.26(d, 2H), 7.44(d, 2H), 7.77(s, 1H). LRMS: m/z(TSP$^+$) 434.2 [MH$^+$] |
| 76 | 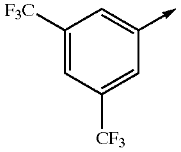 | 12 gum | $^1$H-NMR($CDCl_3$, 400MHz) δ: 3.10(m, 1H), 3.19(dd, 1H), 3.41(m, 2H), 3.78(m, 4H), 4.00(m, 1H), 4.58(m, 3H), 6.80(d, 2H), 7.17(d, 2H), 7.20(s, 1H), 7.80(s, 2H), 7.83(d, 2H). LRMS: m/z(TSP$^+$) 514.0[MH$^+$]. $[\alpha]_D$ = −28.96, (c = 0.096, methanol) |

Preparations 77 to 80

The following compounds of general structure

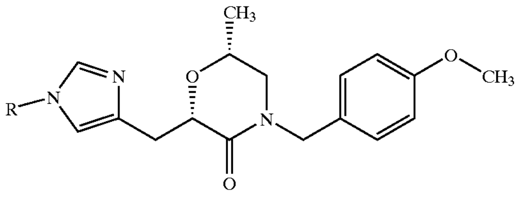

were prepared from the morpholinone of Preparation 55 and the appropriate boronic acids, following a similar procedure to that described in Preparation 70.

| Prep | R | Yield (%) | Data |
|---|---|---|---|
| 77 | 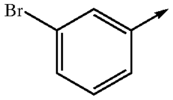 | 33 sticky gum | $^1$H-NMR($CDCl_3$, 400MHz) δ: 1.18(d, 3H), 2.98–3.18(m, 3H), 3.35, 3.38(2xd, 1H), 3.70(m, 3H), 3.85(m, 1H), 4.41(d, 1H), 4.52(m, 1H), 4.58(d, 1H), 6.77(d, 2H), 7.05(m, 4H), 7.20–7.34(m, 1H), 7.42(d, 1H), 7.47(s, 1H), 7.75(s, 1H). LRMS: m/z (TSP$^+$) 470.1, 472.0[MH$^+$] |
| 78 | 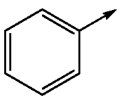 | 28 | $^1$H-NMR($CDCl_3$, 400MHz) δ: 1.19(d, 3H), 3.00(dd, 1H), 3.05–3.22(m, 2H), 3.40(dd, 1H), 3.75(s, 3H), 3.92(m, 1H), 4.42(d, 1H), 4.57(m, 1H), 4.60(d, 1H), 6.78(d, 2H), 7.10(m, 3H), 7.34(m, 3H), 7.43(m, 2H), 7.78(s, 1H). LRMS: m/z(ES$^+$) 392 [MH$^+$] |
| 79[1] | 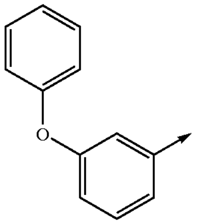 | 11 | $^1$H-NMR($CDCl_3$, 400MHz) δ: 1.18(d, 3H), 3.00(dd, 1H), 3.04–3.19(m, 2H), 3.38(dd, 1H), 3.76(s, 3H), 3.87(m, 1H), 4.42(d, 1H), 4.55(m, 1H), 4.58(d, 1H), 6.78(d, 2H), 6.96(m, 2H), 7.02–7.18(m, 7H), 7.38(m, 3H), 7.76(s, 1H). LRMS: m/z(ES$^+$) 484[MH$^+$] |

-continued

| Prep | R | Yield (%) | Data |
|---|---|---|---|
| 80 | 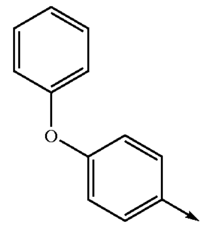 | 41 white foam | $^1$H-NMR($CDCl_3$, 400MHz) δ: 1.19(d, 3H), 3.00(dd, 1H), 3.07–3.20(m, 2H), 3.40(dd, 1H), 3.77(s, 3H), 3.90(m, 1H), 4.42(d, 1H), 4.55(m, 1H), 4.60(dd, 1H), 6.78(d, 2H), 7.01–7.18(m, 8H), 7.26(d, 2H), 7.38(dd, 2H), 7.72(s, 1H). LRMS: m/z(ES$^+$) 484[MH$^+$] |

[1] 3-phenoxyphenylboronic acid (J. Chem. Soc. 1970; 488) was used

Preparation 81

(2S,6R)-2-{[1-(4-Cyclohexylphenyl)-1H-imidazol-4-yl]methyl}-4-(4-methoxybenzyl)-6-methyl-3-morpholinone

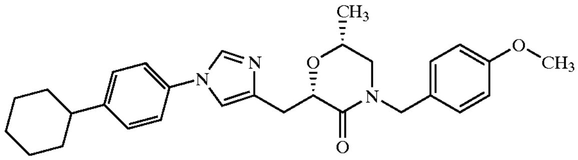

A mixture of copper (II) acetate (398 mg, 2.2 mmol), 4-cyclohexylbenzeneboronic acid (980 mg, 4.8 mmol), the imidazole of Preparation 55 (790 mg, 2.4 mmol) and pyridine (390 μl, 4.8 mmol) in dichloromethane (20 ml) was stirred at room temperature while compressed air was bubbled through the solution for 8 hours, and the solvent was retained by using a "cold finger". The solution was then stirred under a nitrogen atmosphere for a further 18 hours. The mixture was partitioned between dichloromethane (200 ml) and water (200 ml) containing ethylenediaminetetraacetic acid tetrasodium salt (1 g) and aqueous sodium bicarbonate solution (35 ml) and the layers were separated. The organic phase was dried ($MgSO_4$) and concentrated under reduced pressure. The residue was purified by column chromatography using a Biotage® silica gel column and an elution gradient of toluene:diethylamine (95:5 to 92:8 ) to afford the title compound, 140 mg. $^1$H-NMR ($CDCl_3$, 400 MHz) δ: 1.15–1.47 (m, 9H), 1.72–1.94 (m, 4H), 2.55 (m, 1H), 2.99 (dd, 1H), 3.03–3.20 (m, 2H), 3.39 (dd, 1H), 3.73 (s, 3H), 3.90 (m, 1H), 4.42 (d, 1H), 4.56 (m, 2H), 6.78 (d, 2H), 7.02–7.19 (m, 5H), 7.20 (m, 2H), 7.74 (s, 1H). LRMS: m/z (ES$^+$) 474 [MH$^+$]

Preparation 82

4-(Cyclohexyloxy)phenylboronic acid

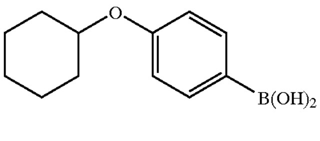

A solution of 4-(cyclohexyloxy)phenylbromide (*J. Am. Chem. Soc.* 1978; 3559) in tetrahydrofuran (40 ml) was degassed then cooled to −78° C. n-Butyl lithium (13.47 ml, 1.45M in hexanes, 19.5 mmol) was added dropwise, and the mixture was stirred for 30 minutes. Triisopropyl borate (5.01 ml, 26.6 mmol) was added dropwise over 10 minutes, and the mixture was allowed to warm slowly, with stirring, to room temperature, then poured into sodium hydroxide solution (0.25M, 300 ml). This mixture was stirred for 15 minutes then extracted with diethyl ether (2×150 ml). The aqueous layer was acidified to pH 1 using concentrated hydrochloric acid and extracted with dichloromethane (2×150 ml). These combined organic extracts were dried ($MgSO_4$) and evaporated under reduced pressure to give the title compound as a white solid, 3.1 g. $^1$H-NMR ($CDCl_3$, 400 MHz) δ: 0.88–1.62 (m, 7H), 1.80 (m, 2H), 2.00 (m, 2H), 4.39 (m, 1H), 6.98 (d, 2H), 8.17 (d, 2H).

Preparation 83

(2S,6R)-2-({1-[4-(Cyclohexyloxy)phenyl]-1H-imidazol-4-yl}methyl)-4-(4-methoxybenzyl)-6-methyl-3-morpholinone

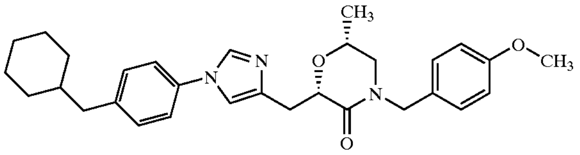

The title compound was obtained in 41% yield from the imidazole of Preparation 55 and the boronic acid of Preparation 82 following a similar procedure to that described in Preparation 81. $^1$H-NMR ($CDCl_3$, 400 MHz) δ: 1.19 (d, 3H), 1.38 (m, 3H), 1.57 (m, 3H), 1.80 (m, 2H), 1.99 (m, 2H), 2.99 (dd, 1H), 3.04–3.20 (m, 2H), 3.39 (dd, 1H), 3.77 (s, 3H), 3.88 (m, 1H), 4.22 (m, 1H), 4.42 (d, 1H), 4.56 (m, 1H), 4.60 (d, 1H), 6.79 (d, 2H), 6.96 (d, 2H), 7.02 (s, 1H), 7.10–7.28 (m, 4H), 7.65 (s, 1H). LRMS: m/z (ES$^+$) 490 [MH$^+$]

Preparation 84

(2RS)2-{[1-(4'-Chloro[1,1'-biphenyl]-3-yl)-1H-imidazol-4-yl]methyl}-4-(4-methoxybenzyl)-3-morpholinone

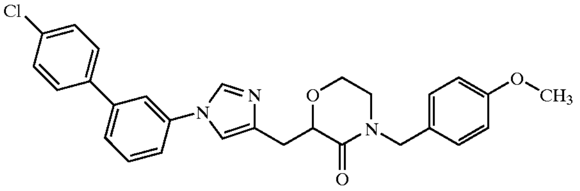

A mixture of the bromide of Preparation 73 (200 mg, 0.44 mmol), 4-chlorophenyl-boronic acid (207 mg, 1.32 mmol), lithium chloride (56 mg, 1.32 mmol), cesium carbonate (433 mg, 1.32 mmol) and tetrakis(triphenylphosphine)palladium (0) (51 mg, 0.044 mmol) in water (2 ml) and tetrahydrofuran (5 ml) was stirred at 75° C. for 18 hours. The cooled mixture was partitioned between dichloromethane and 2M sodium carbonate solution containing 6% v/v 0.88 ammonia. The organic phase was separated, dried ($MgSO_4$) and concentrated under reduced pressure. The residue was purified by column chromatography on silica gel using an elution gradient of toluene:diethylamine (95:5 to 93:7) to afford the title compound as a pale yellow oil, 150 mg. $^1$H-NMR ($CDCl_3$, 400 MHz) δ: 3.05 (m, 1H), 3.20 (dd, 1H), 3.42 (m, 2H), 3.72 (s, 3H), 3.78 (m, 1H), 4.00 (m, 1H), 4.48 (d, 1H), 4.58 (dd, 1H), 4.62 (d, 1H), 6.78 (d, 2H), 7.14 (d, 2H), 7.20 (s, 1H), 7.35–7.59 (m, 8H), 7.82 (s, 1H).

Preparation 85

(2S,6R)-2-{[1-(3'-Chloro[1,1'-biphenyl]-3-yl)-1H-imidazol-4-yl]methyl}-4-(4-methoxybenzyl)-6-methyl-3-morpholinone

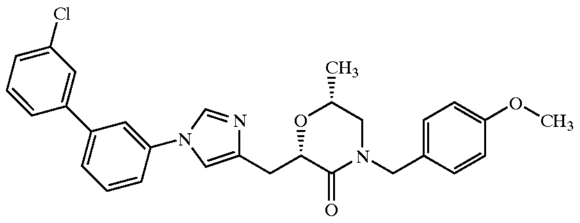

The title compound was obtained as a white solid in 63% yield from the bromide of Preparation 77 and 3-chlorobenzeneboronic acid following a similar procedure to that described in Preparation 84. $^1$H-NMR ($CDCl_3$, 400 MHz) δ: 1.20 (d, 3H), 3.00 (dd, 1H), 3.07–3.21 (m, 2H), 3.41 (dd, 1H), 3.72 (s, 3H), 3.90 (m, 1H), 4.44 (d, 1H), 4.58 (m, 2H), 6.78 (d, 2H), 7.13 (d, 2H), 7.20–7.58 (m, 9H), 7.82 (s, 1H). LRMS: m/z (ES$^+$) 502, 504 [MH$^+$]

Preparation 86

(2RS)-2-{[1-(3',4'-Dichloro[1,1'-biphenyl]-3-yl)-1H-imidazol-4-yl]methyl}-4-(4-methoxybenzyl)-3-morpholinone

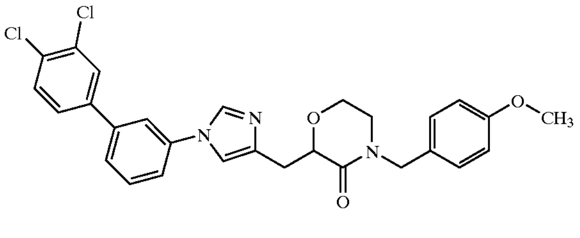

A mixture of the bromide of Preparation 73 (200 mg, 0.44 mmol), 3,4-dichlorobenzene-boronic acid (102 mg, 0.53 mmol), lithium chloride (56 mg, 1.32 mmol), cesium carbonate (433 mg, 1.32 mmol) and tetrakis(triphenylphosphine)palladium(0) (26 mg, 0.022 mmol) in water (2 ml) and tetrahydrofuran (5 ml), was stirred at 75° C. for 2.5 hours. TLC analysis showed starting material remaining, so additional 3,4-dichlorobenzeneboronic acid (204 mg, 1.06 mmol) and tetrakis(triphenylphosphine) palladium(0) (26 mg, 0.022 mmol) were added and the mixture was heated for a further 18 hours at reflux. The cooled mixture was partitioned between dichloromethane and 2M sodium carbonate solution containing 6% v/v 0.88 ammonia. The organic phase was separated, dried ($MgSO_4$) and concentrated under reduced pressure. The residue was purified by column chromatography on silica gel using an elution gradient of toluene:diethylamine (95:5 to 93:7) to afford the title compound as a crystalline solid, 165 mg. $^1$H-NMR ($CDCl_3$, 400 MHz) δ: 3.06 (m, 1H), 3.20 (dd, 1H), 3.41 (m, 2H), 3.75 (m, 4H), 4.00 (m, 1H), 4.48 (d, 1H), 4.58 (m, 1H), 4.62 (d, 1H), 6.58 (2×s, 2H), 7.18 (m, 3H), 7.40 (m, 2H), 7.52 (m, 4H), 7.65 (s, 1H), 7.82 (s, 1H). LRMS: m/z (ES$^+$) 522, 524 [MH$^+$]

Preparation 87

(2S,6R)-2-{[1-(3',4'-Dichloro[1,1'-biphenyl]-3-yl)-1H-imidazol-4-yl]methyl}-4-(4-methoxybenzyl)-6-methyl-3-morpholinone

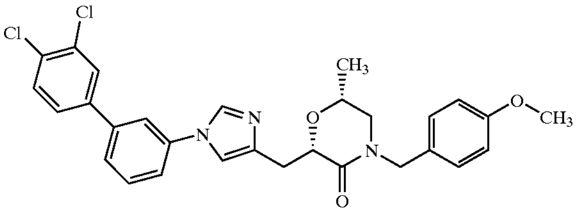

A mixture of the bromide of Preparation 77 (200 mg, 0.425 mmol), 3,4-dichlorobenzeneboronic acid (243 mg, 1.27 mmol), lithium chloride (54 mg, 1.27 mmol), cesium carbonate (416 mg, 1.32 mmol) and tetrakis (triphenylphosphine)palladium(0) (23 mg, 0.02 mmol) in water (2 ml) and tetrahydrofuran (5 ml) was stirred at 75° C. for 3 hours. The cooled mixture was partitioned between ethyl acetate (100 ml) and water (50 ml). The organic phase was separated, dried ($MgSO_4$) and concentrated under reduced pressure. The residue was purified by column chromatography on silica gel using an elution gradient of pentane:ethyl acetate:methanol (50:50:0 to 0:100:0 to 0:95:5) to give a white foam. This was further purified by column chromatography using a Biotage® silica gel column, and an elution gradient of ethyl acetate:methanol (100:0 to 93:7) to afford the title compound as a white foam, 140 mg. $^1$H-NMR ($CDCl_3$, 400 MHz) δ: 1.20 (d, 3H), 3.00–3.21 (m, 3H), 3.40 (m, 1H), 3.75 (s, 3H), 3.90 (m, 1H), 4.42 (m, 1H), 4.59 (m, 2H), 6.78 (d, 2H), 7.13 (d, 2H), 7.19 (s, 1H), 7.38 (m, 1H), 7.40 (m, 1H), 7.50 (m, 4H), 7.65 (s, 1H), 7.81 (s, 1H). LRMS: m/z (ES$^+$) 536, 538 [MH$^+$]

Preparation 88

(2S)-2-[(1-Propyl-1H-imidazol-4-yl)methyl]-3-morpholinone

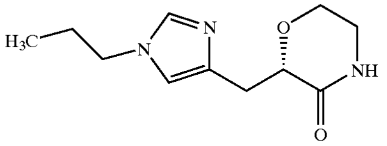

Ammonium cerium (IV) nitrate (4.55 g, 8.30 mmol) was added to a solution of the compound of Preparation 47 (1.43 g, 4.15 mmol) in acetonitrile (9 ml) and water (9 ml) and the mixture was stirred at room temperature for 18 hours then concentrated under reduced pressure and the residue was dissolved in methanol. This solution was purified by column chromatography on silica gel using an elution gradient of dichloromethane:methanol:0.88 ammonia (95:5:0.5 to 90:10:1) to afford an orange oil. This was further purified by column chromatography on Dowex® 50WX8-200 ion exchange resin, using an elution gradient of water:0.88 ammonia (100:0 to 98:2) to afford the title compound, 522 mg. $^1$H-NMR ($CDCl_3$, 400 MHz) δ:0.88 (t, 3H), 1.75 (m, 2H), 3.00 (dd, 1H), 3.23 (m, 2H), 3.50 (m, 1H), 3.74 (m, 1H), 3.79 (t, 2H), 4.00 (m, 1H), 4.43 (dd, 1H), 5.94 (bs, 1H), 6.73 (s, 1H), 7.36 (s, 1H). LRMS: m/z ($ES^+$) 224 [$MH^+$]

Preparation 89

(2RS)-2-[(1-Butyl-1H-imidazol-4-yl)methyl]-3-morpholinone

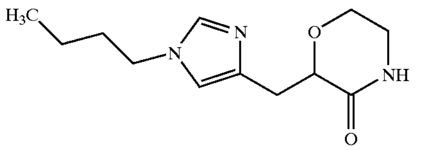

Ammonium cerium (IV) nitrate (5.7 g, 10.4 mmol) was added to a solution of the compound of Preparation 48 (1.87 g, 5.2 mmol) in acetonitrile (50 ml) and water (50 ml), and the mixture was stirred at room temperature for 18 hours. The solvents were evaporated under reduced pressure and the residue was purified using a Dowex® 50WX8-200 ion-exchange column and 5% 0.88 ammonia as eluant. This product was further purified by column chromatography on silica gel using an elution gradient of dichloromethane:methanol:0.88 ammonia (100:0:0 to 90:10:1) to afford the title compound, 300 mg. $^1$H-NMR ($CDCl_3$, 400 MHz) δ:0.96 (t, 3H), 1.34 (m, 2H), 1.75 (m, 2H), 3.02 (dd, 1H), 3.28 (m, 2H), 3.56 (m, 1H), 3.78 (m, 1H), 3.82 (t, 2H), 4.02 (m, 1H), 4.48 (dd, 1H), 5.98 (bs, 1H), 6.77 (s, 1H), 7.38 (s, 1H). LRMS: m/z ($ES^+$) 238 [$MH^+$]

Preparation 90

(2RS)-2-{[1-(2-Cyclohexylethyl)-1H-imidazol-4-yl]methyl}-3-morpholinone

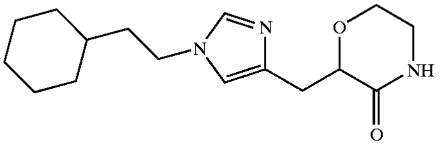

Ammonium cerium (IV) nitrate (1.1 g, 2.0 mmol) was added to a solution of the compound of Preparation 49 (411 mg, 1.0 mmol) in acetonitrile (5 ml) and water (5 ml), and the mixture was stirred at room temperature for 18 hours then concentrated under reduced pressure. The residue was pre-adsorbed onto silica gel and purified by column chromatography on silica gel using an elution gradient of ethyl acetate:dichloromethane:methanol:0.88 ammonia (100:0:0:0 to 75:0:25:0 to 0:90:10:1). The product was further purified by column chromatography on reverse phase polystyrene gel, using an elution gradient of water:methanol (100:0 to 0:100) to afford the title compound, 522 mg. $^1$H-NMR ($CD_3OD$, 400 MHz) δ:1.01 (m, 2H), 1.24 (m, 4H), 1.76 (m, 7H), 3.22 (m, 3H), 3.40 (m, 1H), 3.80 (m, 1H), 4.02 (m, 1H), 4.22 (m, 2H), 4.38 (m, 1H), 7.43 (s, 1H), 8.85 (s, 1H). LRMS: m/z ($TSP^+$) 292.2 [$MH^+$]

Preparation 91

(2R,6S)-2-{[1-(2-Cyclohexylethyl)-1H-imidazol-4-yl]methyl}-6-methyl-3-morpholinone

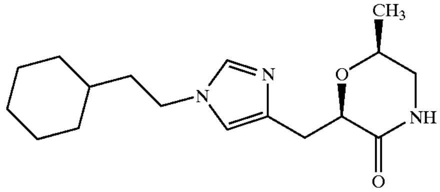

Ammonium cerium (IV) nitrate (387 mg, 0.758 mmol) was added to a solution of the compound of Preparation 61 (120 mg, 0.283 mmol) in acetonitrile (8 ml) and water (5 ml) and the mixture was stirred at 40° C. for 18 hours then concentrated under reduced pressure. The residue was pre-adsorbed onto silica gel and purified by column chromatography on silica gel using an elution gradient of dichloromethane:methanol:0.88 ammonia (98:2:0.2 to 95:.5:0.5) to afford the title compound as a colourless oil, 66 mg. $^1$H-NMR ($CDCl_3$, 400 MHz) δ:0.92 (m, 2H), 1.18 (m, 7H), 1.62 (m, 7H), 2.98 (dd, 1H), 3.18 (m, 2H), 3.23 (dd, 1H), 3.83 (m, 3H), 4.41 (m, 1H), 6.19 (bs, 1H), 6.70 (s, 1H), 7.30 (s, 1H). LRMS: m/z ($ES^+$) 328 [$MNa^+$]

Preparation 92

(2S,6R)-2-{[1-(2-Cyclohexylethyl)-1H-imidazol-4-yl]methyl}-6-methyl-3-morpholinone

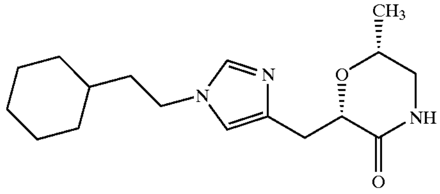

The title compound was obtained as a pale yellow solid in 63% yield from the protected morpholinone of Preparation 62 following the procedure described in Preparation 91. $^1$H-NMR ($CDCl_3$, 400 MHz) δ:0.92 (m, 2H), 1.18 (m, 7H), 1.62 (m, 7H), 2.98 (dd, 1H), 3.19 (m, 2H), 3.23 (dd, 1H), 3.83 (m, 3H), 4.41 (m, 1H), 6.03 (bs, 1H), 6.70 (s, 1H), 7.34 (s, 1H). LRMS: m/z ($ES^+$) 328 [$MNa^+$]

Preparation 93

(2S,6R)-2-({1-[2-(4,4-Dimethylcyclohexyl)ethyl]-1H-imidazol-4-yl}methyl)-6-methyl-3-morpholinone

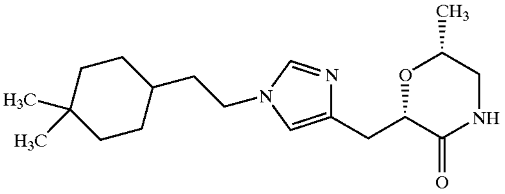

The title compound was obtained in 53% yield from the protected morpholinone of Preparation 66 following a similar procedure to that described in Preparation 91, except that ethyl acetate:methanol:diethylamine (99:0.5:0.5 to 95:2.5:2.5) was used as the column eluant. $^1$H-NMR ($CDCl_3$, 400 MHz) δ:0.82 (2×s, 6H), 1.10 (d, 3H), 1.18–1.38 (m, 8H), 1.48 (m, 1H), 1.63 (m, 2H), 2.98 (m, 1H), 3.19 (m, 2H), 3.23 (dd, 1H), 3.84 (m, 3H), 4.41 (m, 1H), 6.97 (bs, 1H), 7.21 (s, 1H), 7.34 (s, 1H). LRMS: m/z ($ES^+$) 334 [$MH^+$]

Preparation 94

(2S,6R)-2-{[1-(3-Cyclohexyl-3-methylbutyl)-1H-imidazol-4-yl]methyl}-6-methyl-3-morpholinone

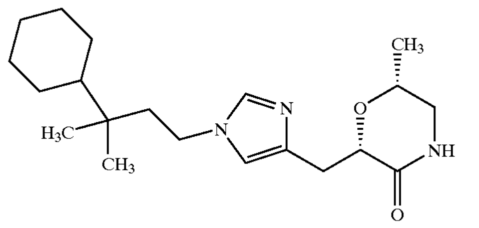

The title compound was obtained in 52% yield from the protected morpholinone of Preparation 65 following a similar procedure to that described in Preparation 91, except that dichloromethane:methanol:0.88 ammonia (99:1:0.1 to 93:7:0.7) was used as the column eluant. $^1$H-NMR ($CD_3OD$, 400 MHz) δ:0.86 (s, 6H), 1.00 (m, 2H), 1.03–1.28 (m, 7H), 1.70 (m, 7H), 2.90 (m, 1H), 3.03 (ml 1H), 3.18 (m, 2H), 3.82 (m, 1H), 3.95 (m, 2H), 4.36 (m, 1H), 5.42 (s, 1H), 6.86 (s, 1H), 7.50 (s, 1H). LRMS: m/z ($ES^+$) 348 [$MH^+$]

Preparation 95

(2S,5S)-2-{[1-(2-Cyclohexylethyl)-1H-imidazol-4-yl]methyl}-5-methyl-3-morpholinone

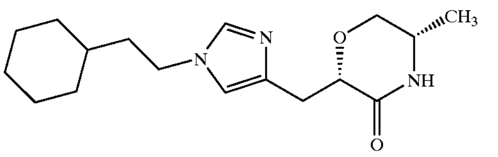

A mixture of the protected morpholinone of Preparation 63 (170 mg, 0.4 mmol) and ammonium cerium (IV) nitrate (550 mg, 1.0 mmol) in water (1 ml) and acetonitrile (1 ml) was stirred at 40° C. for 18 hours then concentrated under reduced pressure. The residue was purified by column chromatography using a Biotage® silica gel column and an elution gradient of ethyl acetate:diethylamine (95:5 to 80:20) to afford the title compound, 18 mg. $^1$H-NMR ($CDCl_3$, 400 MHz) δ:0.97 (m, 2H), 1.20 (m, 7H), 1.66 (m, 7H), 3.06 (dd, 1H), 3.25 (dd, 1H), 3.58 (m, 1H), 3.65 (dd, 1H), 3.83 (m, 3H), 4.43 (dd, 1H), 6.15 (bs, 1H), 6.78 (s, 1H), 7.38 (s, 1H).

Preparation 96

(2R,5R)-2-{[1-(2-Cyclohexylethyl)-1H-imidazol-4-yl]methyl}-5-methyl-3-morpholinone

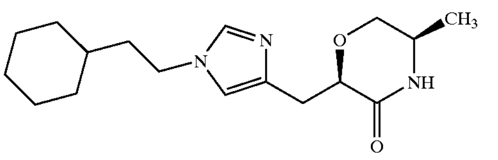

The title compound was obtained in 34% from the protected morpholinone of Preparation 64 following the procedure described in Preparation 95. $^1$H-NMR ($CDCl_3$, 400 MHz) δ:0.78–0.98 (m, 2H), 1.03–1.22 (m, 7H), 1.62 (m, 7H), 3.02 (m, 1H), 3.18 (dd, 1H), 3.55 (m, 1H), 3.61 (dd, 1H), 3.77 (dd, 1H), 3.82 (t, 2H), 4.38 (m, 1H), 6.24 (bs, 1H), 6.73 (s, 1H), 7.37 (s, 1H).

Preparation 97

(2RS)-2-{[1-(2-Phenylethyl)-1H-imidazol-4-yl]methyl}-3-morpholinone

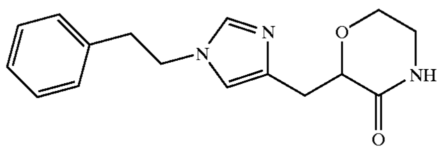

Ammonium cerium (IV) nitrate (883 mg, 1.6 mmol) was added to a solution of the compound of Preparation 50 (326 mg, 0.81 mmol) in acetonitrile (2.4 ml) and water (2.4 ml) and the mixture was stirred at room temperature for 5 days, then concentrated under reduced pressure. The residue was dissolved in methanol and adsorbed onto silica gel, then purified by column chromatography on silica gel using an elution gradient of dichloromethane:methanol:0.88 ammonia (100:0:0 to 90:10:1) to afford the title compound as an orange oil, 97 mg. $^1$H-NMR ($CDCl_3$, 400 MHz) δ:3.02 (m, 3H), 3.26 (m, 2H), 3.52 (m, 1H), 3.77 (m, 1H), 4.00 (m, 1H), 4.10 (t, 2H), 4.43 (dd, 1H), 5.99 (bs, 1H), 6.70 (s, 1H), 7.05 (d, 2H), 7.24 (m, 4H). LRMS: m/z ($ES^+$) 286 [$MH^+$]

Preparation 98

(2RS)-2-({1-[2-(4-Bromophenyl)ethyl]-1H-imidazol-4-yl}methyl)-3-morpholinone

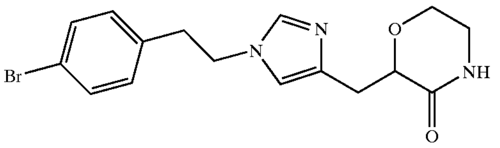

A solution of ammonium cerium (IV) nitrate (1.35 g, 2.48 mmol) in water (5 ml) was added to a solution of the bromide of Preparation 59 (600 mg, 1.24 mmol) in acetonitrile (10 ml) and the mixture was stirred at 40° C. for 18 hours. TLC analysis showed starting material remaining, so additional ammonium cerium (IV) nitrate (308 mg, 0.56 mmol) was added and the mixture was stirred at 40° C. for a further 2 hours. The cooled mixture was concentrated under reduced pressure and the residue was purified by column chromatography on silica gel using an elution gradient of dichloromethane:methanol:0.88 ammonia (98:2:0.2 to 95:5:0.5) to afford the title compound, 250 mg. $^1$H-NMR ($CDCl_3$, 400 MHz) δ:2.98 (t, 2H), 3.03 (m, 1H), 3.25 (m, 2H), 3.52 (m, 1H), 3.77 (m, 1H), 4.00 (m, 1H), 4.05 (t, 2H), 4.42 (m, 1H), 5.99 (bs, 1H), 6.65 (s, 1H), 6.93 (d, 2H), 7.22 (s, 1H), 7.40 (d, 2H□□

Preparations 99 to 101

The following compounds of general structure

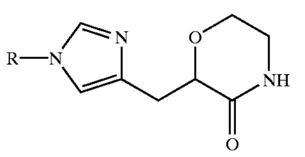

were prepared from the corresponding protected morpholinones following a similar procedure to that described in Preparation 98.

| Ex | R | Yield (%) | Data |
|---|---|---|---|
| 99 | 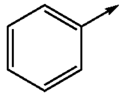 | 58 | $^1$H-NMR($CDCl_3$, 400MHz) δ: 3.10(dd, 1H), 3.25(m, 1H), 3.37(m, 1H), 3.58(m, 1H), 3.78(m, 1H), 4.02(m, 1H), 4.54(m, 1H), 5.83(bs, 1H), 7.15(s, 1H), 7.33(m, 3H), 7.42(m, 2H), 7.78(s, 1H). LRMS: m/z($ES^+$) 280[$MNa^+$] |
| 100 | 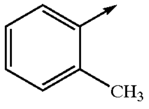 | 74 | $^1$H-NMR($CDCl_3$, 400MHz) δ: 2.20(s, 3H), □3.16(dd, 1H), 3.30(m, 1H), 3.38(dd, 1H), 3.58(m, 1H), 3.80(m, 1H), 4.04(m, 1H), 4.56(dd, 1H), 6.18(bs, 1H), 6.90(s, 1H), 7.20–7.35(m, 4H), 7.50(s, 1H). HRMS: m/z 272.1394[$MH^+$] |
| 101[1] | 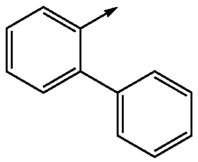 | | $^1$H-NMR($CD_3OD$, 400MHz) δ: 2.92(dd, 1H), 3.05(m, 1H), 3.19(m, 1H), 3.63(m, 1H), 3.86(m, 1H), 4.22(m, 1H), 6.82(s, 1H), 7.10(m, 2H), 7.30(m, 3H), 7.40(m, 1H), 7.50(m, 4H). LRMS m/z ($ES^+$) 356[$MNa^+$] |

[1]ethyl acetate:methanol:diethylamine (100:0:0 to 90:5:5) used as the column eluant

Preparation 102

(2RS)-2-{[1-(3-Phenoxyphenyl)-1H-imidazol-4-yl]methyl}-3-morpholinone

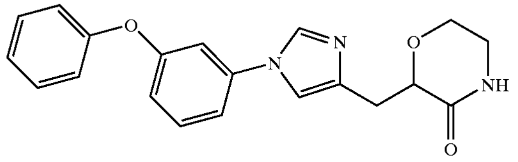

A solution of ammonium cerium (IV) nitrate (350 mg, 063 mmol) in water (2 ml) was added to a solution of the protected morpholine of Preparation (120 mg, 0.256 mmol) in acetonitrile (2 ml), and the mixture was stirred at 40° C. for 18 hours. TLC analysis showed starting material remaining, so additional ammonium cerium (IV) nitrate (500 mg, 0.91 mmol) was added, and the mixture was stirred at 40° C. for a further 8 hours. The mixture was evaporated under reduced pressure and the residue was partitioned between dichloromethane (50 ml) and a solution of ethylenediaminetetraacetic acid (1 g) in saturated sodium bicarbonate solution (50 ml). The phases were separated and the organic layer was dried ($MgSO_4$) and evaporated under reduced pressure. The crude product was purified by column chromatography on silica gel using an elution gradient of ethyl acetate:methanol:diethylamine (100:0:0 to 96:2:2) to afford the title compound, 25 mg. $^1$H-NMR ($CDCl_3$, 400 MHz) δ: 3.05 (dd, 1H), 3.21–3.18 (m, 2H), 3.57 (m, 1H), 3.77 (m, 1H), 400 (m, 1H), 4.48 (dd, 1H), 6.15 (bs, 1H), 6.90 (d, 1H), 6.98 (s, 1H), 7.02 (m, 3H), 7.14 (m, 2H), 7.37 (m, 3H), 7.74 (s, 1H). LRMS: m/z ($TSP^+$) 350.0 [$MH^+$]

Preparation 103

(2RS)-2-{[1-(2-Naphthyl)-1H-imidazol-4-yl]methyl}-3-morpholinone

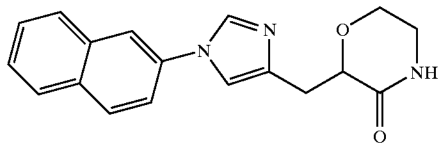

The title compound was obtained as a yellow gum in 56% yield from the protected morpholinone of Preparation 72, following a similar procedure to that described in Preparation 102, except that dichloromethane:methanol:0.88 ammonia (100:0:0 to 90:10:1) was used as the column eluant. $^1$H-NMR ($CDCl_3$, 400 MHz) δ: □3.15 (dd, 1H), 3.23 (m, 1H), 3.38 (dd, 1H), 3.58 (m, 1H), 3.78 (m, 1H), 4.02 (m, 1H), 4.53 (dd, 1H), 6.01 (bs, 1H), 7.22 (d, 2H), 7.48 (m, 3H), 7.75–7.94 (m, 4H). LRMS: m/z ($ES^+$) 308 [$MH^+$]

Preparation 104

(−)-(2S)-2-{[1-Phenyl-1H-imidazol-4-yl]methyl}-3-morpholinone

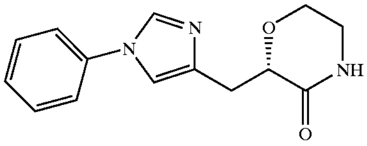

Ammonium cerium (IV) nitrate (1.43 g, 2.61 mmol) was added to a solution of the protected morpholinone of Preparation 74 (330 mg, 0.87 mmol) in water (2 ml) and acetonitrile (2 ml), and the mixture was stirred at 40° C. for 4 hours. TLC analysis showed starting material remaining, so additional ammonium cerium (IV) nitrate (1.43 g, 2.61 mmol) was added, and the mixture was stirred at 40° C. for a further 2 hours. The mixture was partitioned between dichloromethane (200 ml) and a solution of ethylenediaminetetraacetic acid (1 g) in saturated sodium bicarbonate solution (50 ml). The phases were separated and the organic layer was dried ($MgSO_4$) and evaporated under reduced pressure. The crude product was purified by column chromatography on silica gel using an elution gradient of ethyl acetate:methanol:diethylamine (100:0:0 to 96:2:2). The product was azeotroped with toluene and dichloromethane to afford the title compound as an oil, 173 mg. $^1$H-NMR ($CDCl_3$, 400 MHz) δ: □3.14 (dd, 1H), 3.28 (m, 1H), 3.38 (dd, 1H), 3.58 (m, 1H), 3.80 (m, 1H), 4.05 (m, 1H), 4.56 (dd, 1H), 5.98 (bs, 1H), 7.17 (s, 1H), 7.37 (m, 3H), 7.45 (m, 2H), 7.79 (s, 1H). LRMS: m/z (TSP$^+$) 258.1 [MH$^+$][α]$_D$=−70.59, (c=0.104, methanol)

Preparation 105

(2S)-2-{[1-(4-tert-Butylphenyl)-1H-imidazol-4-yl]methyl}-3-morpholinone

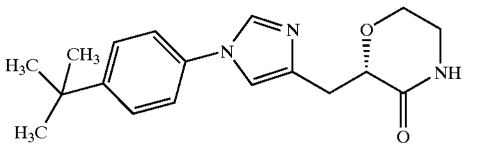

Ammonium cerium (IV) nitrate (297 mg, 0.55 mmol) was added to a solution of the protected morpholinone of Preparation 75 (94 mg, 0.22 mmol) in water (2 ml) and acetonitrile (2 ml), and the mixture was stirred at 40° C. for 15 hours. Ethylenediaminetetraacetic acid (0.5 g) in saturated sodium bicarbonate solution (5 ml) was added and the mixture was extracted with dichloromethane (2×50 ml). The combined organic extracts were dried ($MgSO_4$) and evaporated under reduced pressure. The crude product was purified by column chromatography on silica gel using an elution gradient of ethyl acetate:methanol:diethylamine (98:1:1 to 94:3:3), to afford the title compound as an oil, 22 mg. $^1$H-NMR ($CDCl_3$, 400 MHz) δ: 1.37 (s, 9H), 3.12 (dd, 1H), 3.26 (m, 1H), 3.38 (dd, 1H), 3.58 (m, 1H), 3.79 (m, 1H), 4.04 (m, 1H), 4.55 (m, 1H), 6.22 (bs, 1H), 7.10 (s, 1H), 7.25 (d, 2H), 7.42 (d, 2H), 7.77 (s, 1H). LRMS: m/z (TSP$^+$) 314.1 [MH$^+$]

Preparation 106

(−)-(2S)-2-({1-[3,5-Bis(trifluoromethyl)phenyl]-1H-imidazol-4-yl}methyl)-3-morpholinone

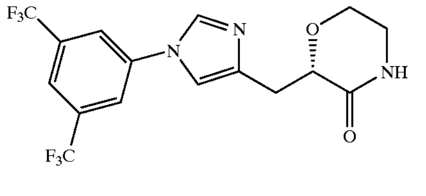

The title compound was obtained as a solid in 81% yield from the protected morpholinone of Preparation 76 following the procedure described in Preparation 105. $^1$H-NMR ($CDCl_3$, 400 MHz) δ: □3.18 (dd, 1H), 3.30 (m, 1H), 3.39 (dd, 1H), 3.60 (m, 1H), 3.80 (m, 1H), 4.06 (m, 1H), 4.55 (m, 1H), 5.88 (bs, 1H), 7.20 (s, 1H), 7.81 (s, 2H), 7.84 (s, 1H), 7.87 (s, 1H). LRMS: m/z (TSP$^+$) 394.0 [MH$^+$]. [α]$_D$=−40.35, (c=0.116, methanol)

Preparation 107

(2RS)-2-{[1-(4'-Chloro[1,1'-biphenyl]-3-yl)-1H-imidazol-4-yl]methyl}-3-morpholinone

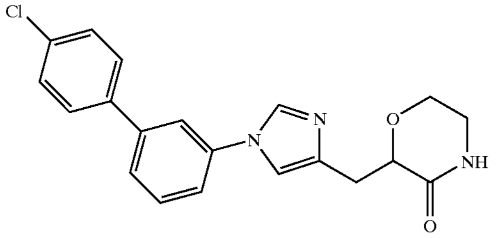

The title compound was obtained as a solid in 91% yield from the protected morpholinone of Preparation 84 following the procedure described in Preparation 105. $^1$H-NMR ($CDCl_3$, 400 MHz) δ: □3.10 (dd, 1H), 3.25 (m, 1H), 3.38 (dd, 1H), 3.57 (m, 1H), 3.78 (m, 1H), 4.02 (m, 1H), 4.52 (dd, 1H), 5.96 (bs, 1H), 7.17 (s, 1H), 7.37 (m, 3H), 7.42 (m, 1H), 7.50 (m, 3H), 7.57 (s, 1H), 7.80 (s, 1H). LRMS: m/z (ES$^-$) 366 (M−H$^-$)

Preparation 108

(2RS)-2-{[1-(3',4'-Dichloro[1,1'-biphenyl]-3-yl)-1H-imidazol-4-yl]methyl}-3-morpholinone

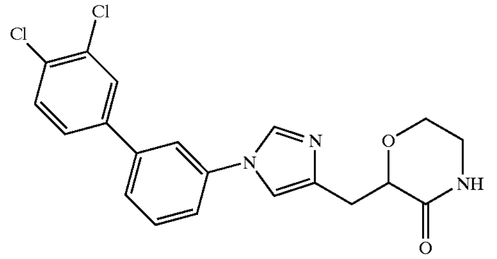

The title compound was obtained in 49% yield from the protected morpholinone of Preparation 86 following the procedure described in Preparation 105. $^1$H-NMR ($CDCl_3$, 400 MHz) □□□3.10 (dd, 1H), 3.25 (m, 1H), 3.38 (dd, 1H), 3.57 (m, 1H), 3.78 (m, 1H), 4.02 (m, 1H), 4.52 (dd, 1H), 5.86 (bs, 1H), 7.18 (s, 1H), 7.37 (m, 2H), 7.50 (m, 4H), 7.62 (s, 1H), 7.80 (s, 1H). LRMS: m/z (ES$^+$) 402, 404 (MH$^+$)

Preparations 109 to 114

The following compounds of the general structure

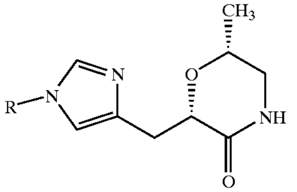

were prepared from the appropriate protected morpholinones, following a similar procedure to that described in Preparation 105.

| Prep | R | Yield (%) | Data |
|---|---|---|---|
| 109 | 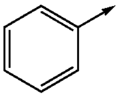 | 50 | $^1$H-NMR($CDCl_3$, 400MHz)δ: □1.22(d, 3H), 3.08 (dd, 1H), 3.22(m, 2H), 3.38(dd, 1H), 3.92(m, 1H), 4.50(m, 1H), 6.62(bs, 1H), 7.16(s, 1H), 7.37(m, 3H), 7.42(m, 2H), 7.78(s, 1H). |
| 110 | 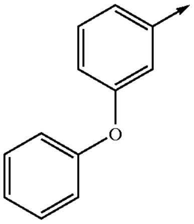 | 25 | $^1$H-NMR($CDCl_3$, 400MHz)δ: □1.20(d, 3H), 3.02 (dd, 1H), 3.20(m, 2H), 3.34(dd, 1H), 3.88(m, 1H), 4.44(m, 1H), 6.05(bs, 1H), 6.90(d, 1H), 6.98(s, 1H), 7.02(m, 4H), 7.14(m, 1H), 7.36(m, 3H), 7.70(s, 1H). LRMS: m/z($ES^+$)364[$MH^+$] |
| 111 | 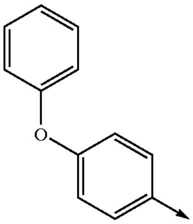 | 44 sticky gum | $^1$H-NMR($CDCl_3$, 400MHz)δ: 1.24(d, 3H), 3.09 (dd, 1H), 3.22(m, 2H), 3.39(dd, 1H), 3.95(m, 1H), 4.50(m, 1H), 5.86(bs, 1H), 7.03(m, 4H), 7.18(m, 2H), 7.36(m, 4H), 7.70(s, 1H). LRMS: m/z($ES^+$)364[$MH^+$] |
| 112[1] | 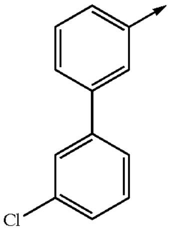 | 44 | $^1$H-NMR($CDCl_3$, 400MHz)δ: 1.23(d, 3H), 3.10 (dd, 1H), 3.22(m, 2H), 3.39(dd, 1H), 3.94(m, 1H), 4.55(m, 1H), 5.84(bs, 1H), 7.20(s, 1H), 7.39(m, 3H), 7.42–7.60(m, 5H), 7.80(s, 1H). |
| 113[1] | 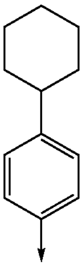 | 40 solid | $^1$H-NMR($CDCl_3$, 400MHz)δ: □1.22(m, 5H), 1.40 (m, 4H), 1.70–1.90(m, 4H), 2.55(m, 1H), 3.09 (dd, 1H), 3.21(m, 2H), 3.38(dd, 1H), 3.92(m, 1H), 4.50(m, 1H), 6.00(bs, 1H), 7.10(s, 1H), 7.27(m, 4H), 7.74(s, 1H). LRMS: m/z($ES^+$)354[$MH^+$] |
| 114[2] | 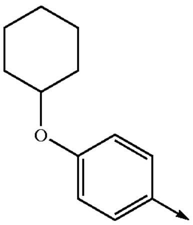 | 34 | $^1$H-NMR($CDCl_3$, 400MHz)δ: □0.88–1.15(m, 2H), 1.22(d, 3H), 1.38(m, 3H), 1.58(m, 1H)1.80(m, 2H), 1.99(m, 2H), 3.06(dd, 1H), 3.22(m, 2H), 3.39(dd, 1H), 3.92(m, 1H), 4.22(m, 1H), 4.50 (m, 1H), 5.84(bs, 1H), 6.97(d, 2H), 7.05(s, 1H), 7.22(d, 2H), 7.64(s, 1H). |

[1]Acetonitrile:water (3:1, by volume) was used as the reaction solvent

[2]Acetonitrile:water (2:1, by volume) was used as the reaction solvent

Preparation 115

(2S,6R)-2-{[1-(3',4'-Dichloro[1,1'-biphenyl]-3-yl)-1H-imidazol-4-yl]methyl}-6-methyl-3-morpholinone

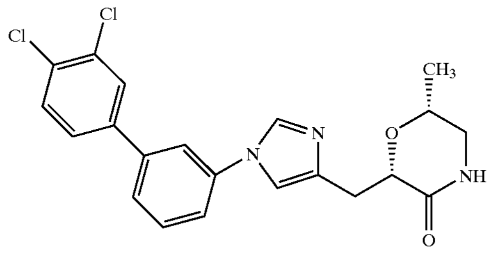

The title compound was obtained as a white foam in 63% yield from the protected morpholinone of Preparation 87 following a similar procedure to that described in Preparation 105. $^1$H-NMR ($CDCl_3$, 400 MHz) δ: □1.24 (d, 3H), 3.14 (dd, 1H), 3.23 (m, 2H), 3.40 (dd, 1H), 3.97 (m, 1H), 4.56 (dd, 1H), 5.80 (bs, 1H), 7.10 (s, 1H), 7.40 (m, 2H), 7.55 (m, 4H), 7.68 (s, 1H), 7.81 (s, 1H). LRMS: m/z ($TSP^+$) 416.1, 420.1 [$MH^+$]

Preparation 116

(2S)-2-(1H-Imidazol-4-ylmethyl)-3-morpholinone

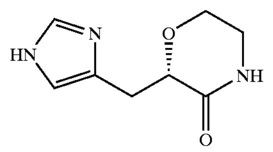

A mixture of the protected morpholinone of Preparation 53 (500 mg, 1.66 mmol), and ammonium cerium (IV) nitrate (2.5 g, 4.5 mmol) in water (6 ml) and acetonitrile (6 ml) was stirred at 40° C. for 18 hours. Potassium carbonate (1.5 g) was added and the mixture was stirred for 10 minutes then adsorbed onto silica gel. The product was isolated by column chromatography on silica gel using ethyl acetate: methanol:diethylamine (96:2:2 to 80:10:10) and was further purified by column chromatography on silica gel using dichloromethane:methanol (90:10 to 85:15) to afford the title compound, 240 mg. $^1$H-NMR ($CD_3OD$, 400 MHz) δ: □3.02–3.42 (m, 4H), 3.78 (m, 1H0, 4.00 (m, 1H), 4.38 (m, 1H), 6.75 (s, 1H), 7.78 (s, 1H). HRMS: m/z ($ES^+$) 182.0924 [$MH^+$]

Preparation 117

(−)-(2S,6R)-2-(1H-imidazol-4-ylmethyl)-6-methyl-3-morpholinone

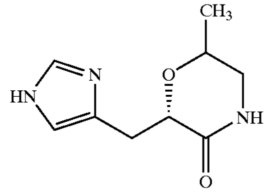

A mixture of the protected morpholinone of Preparation 55 (1 g, 3.2 mmol) and ammonium cerium (IV) nitrate (5.2 g, 9.6 mmol) in water (20 ml) and acetonitrile (30 ml) was stirred at 40° C. for 18 hours. The solvent was evaporated under reduced pressure. The residue was suspended in a mixture of dichloromethane:methanol:0.88 ammonia (99:1:0.1 by volume) and purified twice by column chromatography on silica gel using an elution gradient of dichloromethane:methanol:0.88 ammonia (90:10:1). The resulting oil was azeotroped with diethyl ether to afford the title compound as a colourless foam, 380 mg. $^1$H-NMR ($CD_3OD$, 400 MHz) δ: □1.21 (d, 3H), 3.02 (m, 2H), 3.19 (m, 2H), 3.90 (m, 1H), 4.36 (m, 1H), 6.81 (s, 1H), 7.54 (s, 1H). LRMS: m/z ($ES^+$) 196 [$MH^+$]. $[\alpha]_D$=−104.56 (c=0.19, methanol)

Preparation 118 tert-Butyl (2S)-2-{[1-(tert-butoxycarbonyl)-1H-imidazol-4-yl]methyl}-3-oxo-4-morpholinecarboxylate

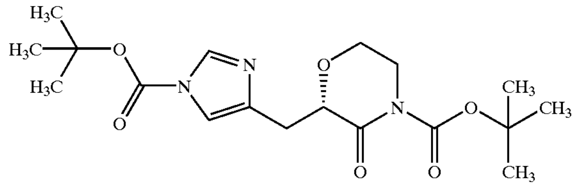

A solution of the morpholinone of Preparation 116 (70 mg, 0.39 mmol), dimethylaminopyridine (3 mg) and di-tert-butyl dicarbonate (354 mg, 1.62 mmol) in acetonitrile (5 ml) was stirred at room temperature for 42 hours. The mixture was concentrated under reduced pressure and the residue was purified by column chromatography on silica gel using an elution gradient of dichloromethane:methanol: 0.88 ammonia (99:1:0.1 to 95:5:0.5) to afford the title compound, 96 mg. $^1$H-NMR ($CDCl_3$, 400 MHz) δ: □1.58 (s, 9H), 1.61 (s, 9H), 3.04 (dd, 1H), 3.35 (dd, 1H), 3.78 (m, 3H), 4.05 (m, 1H), 4.50 (m, 1H), 7.20 (s, 1H), 8.00 (s, 1H). HRMS: m/z ($ES^+$) 382.1972 [$MH^+$]

Preparation 119 tert-Butyl (2S,6R)-2-({1-[4-(cyclohexyloxy)phenyl]-1H-imidazol-4-yl}methyl)-6-methyl-3-oxomorpholine-4-carboxylate

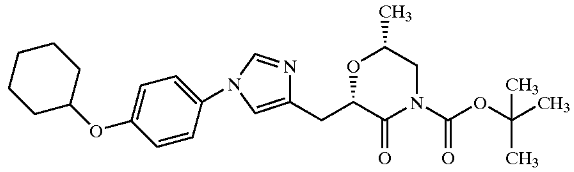

4-Dimethylaminopyridine (49 mg, 0.4 mmol) and di-tert-butyl dicarbonate (174 mg, 0.8 mmol) were added to a solution of the morpholinone of Preparation 114 (135 mg, 0.37 mmol) in acetonitrile (5 ml), and the mixture was stirred at room temperature for 5 hours. TLC analysis showed starting material remaining, so additional di-tert-butyl dicarbonate (87 mg, 0.4 mmol) was added, and the mixture was stirred at room temperature for a further 18 hours. The reaction mixture was concentrated under reduced pressure and the residue was purified by column chromatography on silica gel using ethyl acetate as eluant, to give the title compound, 95 mg. LRMS: m/z ($ES^+$) 470 [$MH^+$]

Preparation 120

Lithium (2S)-2-({(1R)-2-[(tert-butoxycarbonyl)amino]-1-methylethyl}oxy)-3-{1-[4-(cyclohexyloxy)phenyl]-1H-imidazol-4-yl}propanoate

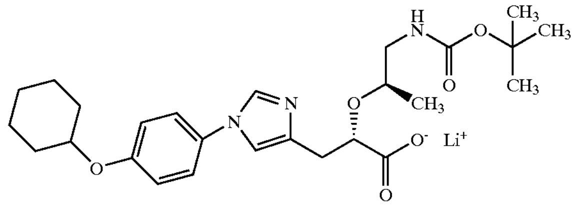

A mixture of the protected morpholinone of Preparation 119 (87 mg, 0.19 mmol) and lithium hydroxide (24 mg, 0.56 mmol) in tetrahydrofuran (0.5 ml) and water (1 ml) was stirred at room temperature for 18 hours. The reaction mixture was evaporated under reduced pressure to afford the title compound. $^{1}$H-NMR ($D_2O$, 400 MHz) δ: 0.60 (m, 2H), 1.00–1.38 (m, 16H), 1.50 (m, 2H), 1.70 (m, 2H), 2.58 (m, 1H), 2.80 (m, 2H), 2.94 (m, 1H), 3.30 (m, 1H), 3.82 (m, 1H), 4.00 (m, 1H), 6.63 (d, 2H), 6.82 (s, 1H), 7.00 (d, 2H), 7.56 (s, 1H). LRMS: m/z ($ES^-$) 486 $[M-H]^-$ Preparation 121

(2RS)-2-({1-[2-(4'-Ethyl[1,1'-biphenyl]-4-yl)ethyl]-1H-imidazol-4-yl}methyl)-3-morpholinone

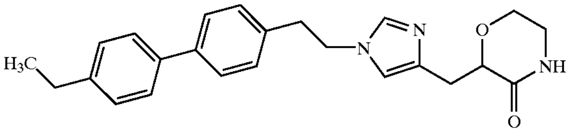

A mixture of the bromo compound of Preparation 98 (250 mg, 0.69 mmol), 4-ethylbenzeneboronic acid (154 mg, 1.03 mmol), tetrakis(triphenylphosphine)palladium(0) 78 mg, 0.068 mmol) and sodium carbonate solution (411 μl, 2M, 0.823 mmol) in water (1 ml) and dioxan (5 ml) was heated at 100° C. for 3 hours. The cooled reaction mixture was diluted with water (10 ml), and the mixture was extracted with ethyl acetate (3x15 ml). The combined organic extracts were dried ($MgSO_4$) and evaporated under reduced pressure. The crude product was purified by column chromatography on silica gel using an elution gradient of dichloromethane:methanol:0.88 ammonia (99:1:0.1 to 95:5:0.5) to afford the title compound, 170 mg. $^{1}$H-NMR ($CDCl_3$, 400 MHz) δ: 1.22 (t, 3H), 2.64 (q, 2H), 3.02 (m, 3H), 3.22 (m, 2H), 3.44 (m, 1H), 3.72 (m, 1H), 3.98 (m, 1H), 4.10 (t, 2H), 4.42 (m, 1H), 5.90 (bs, 1H), 6.70 (s, 1H), 7.08 (d, 2H), 7.22 (m, 3H), 7.44 (m, 4H).

Preparations 122 to 131

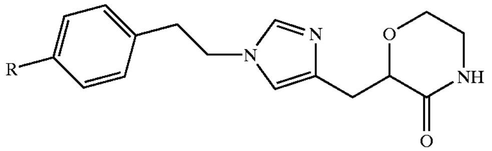

Aryl boronic acids (R—B(OH)$_2$), (0.74 mmol) were added to solutions of the bromo compound of Preparation 98 (180 mg, 0.49 mmol) tetrakis(triphenylphosphine)palladium (0) (56 mg, 0.051 mmol) and sodium carbonate solution (295 μl, 2M, 0.593 mmol) in water (1 ml) and dioxan (5 ml). The reaction mixtures were heated to 100° C. for 4 hours, then allowed to cool. Water (15 ml) was added, and the mixtures were extracted with ethyl acetate (3x15 ml). The combined organic extracts were dried ($MgSO_4$) and evaporated under reduced pressure. The crude products were purified by column chromatography on silica gel using an elution gradient of dichloromethane:methanol:0.88 ammonia (97:3:0.3 to 95:5:0.5) to afford the desired products, shown in the following table.

| Prep | R | Yield (%) | Data |
|---|---|---|---|
| 122 | 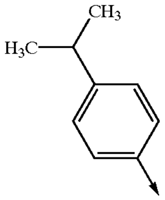 | 63 | $^{1}$H-NMR($CDCl_3$, 400MHz)δ: □1.28(d, 6H), 2.95 (m, 1H), 3.02(m, 3H), 3.24(m, 2H), 3.52(m, 1H), 3.75(m, 1H), 4.00(m, 1H), 4.12(t, 2H), 4.44(m, 1H), 5.92(bs, 1H), 6.75(bs, 1H), 7.14(d, 2H), 7.28(m, 3H), 7.50(m, 4H). LRMS: m/z($ES^+$) 404[$MH^+$]□ |
| 123 | 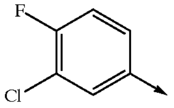 | 78 | $^{1}$H-NMR($CDCl_3$, 400MHz)δ: □□3.04(m, 3H), 3.26(m, 2H), 3.54(m, 1H), 3.76(m, 1H), 4.00 (m, 1H), 4.15(t, 2H), 4.44(m, 1H), 6.06(bs, 1H), 6.75(s, 1H), 7.14(d, 2H), 7.19(dd, 1H), 7.24(s, 1H), 7.40(m, 3H), 7.59(d, 1H). |
| 124 | 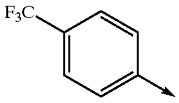 | 61 | $^{1}$H-NMR($CDCl_3$, 400MHz)δ: □3.06(m, 3H), 3.25 (m, 2H), 3.54(m, 1H), 3.77(m, 1H), 4.01(m, 1H), 4.15(t, 2H), 4.44(m, 1H), 5.83(bs, 1H), 6.77(s, 1H), 7.17(d, 2H), 7.24(s, 1H), 7.55(d, 2H), 7.66 (m, 4H). LRMS: m/z($ES^+$)452[$MNa^+$] |

-continued

| Prep | R | Yield (%) | Data |
|---|---|---|---|
| 125 | 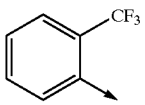 | 66 | $^1$H-NMR($CDCl_3$, 400MHz)δ: □3.05(m, 3H), 3.26 (m, 2H), 3.55(m, 1H), 3.77(m, 1H), 4.00(m, 1H), 4.17(t, 2H), 4.45(m, 1H), 5.96(bs, 1H), 6.74(s, 1H), 7.09(d, 2H), 7.20–7.34(m, 4H), 7.42(dd, 1H), 7.57(dd, 1H), 7.75(d, 1H). Microanalysis found: C, 62.77; H, 5.21; N, 9.46. $C_{23}H_{22}N_3O_2F_3$:0.5$H_2O$ requires C, 63.01; H, 5.29; N, 9.58%. |
| 126 | 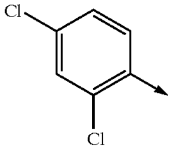 | 56 | $^1$H-NMR($CDCl_3$, 400MHz)δ: 3.02(m, 3H), 3.22 (m, 2H), 3.50(m, 1H), 3.74(m, 1H), 4.00(m, 1H), 4.14(t, 2H), 4.42(dd, 1H), 5.95(s, 1H), 6.74(s, 1H), 7.08(d, 2H), 7.19–7.35(m, 5H), 7.42(s, 1H). LRMS: m/z(ES$^+$)430, 432[MH$^+$] |
| 127 | 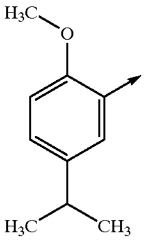 | 70 | $^1$H-NMR($CDCl_3$, 400MHz)δ: □1.25(d, 6H), 2.90 (m, 1H), 3.05(m, 3H), 3.22(m, 2H), 3.44(m, 1H), 3.75(m, 4H), 4.00(m, 1H), 4.15(t, 2H), 4.44(m, 1H), 5.86(s, 1H), 6.78(s, 1H), 6.92(d, 1H), 7.15 (m, 4H), 7.35(s, 1H), 7.44(d, 2H). LRMS: m/z (ES$^+$)456[MNa$^+$] |
| 128 | 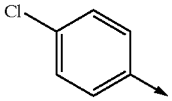 | | $^1$H-NMR($CDCl_3$, 400MHz)δ: □3.02(m, 3H), 3.22 (m, 2H), 3.47(m, 1H), 3.70(m, 1H), 3.98(m, 1H), 4.09(t, 2H), 4.42(dd, 1H), 5.82(s, 1H), 6.74(s, 1H), 7.10(d, 2H), 7.22(s, 1H), 7.38(d, 2H), 7.44 (m, 4H). HRMS: m/z 396.147[MH$^+$] |
| 129 | 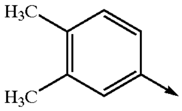 | 36 | $^1$H-NMR($CDCl_3$, 400MHz)δ: □2.35(2xs, 6H), 3.06(m, 3H), 3.30(m, 2H), 3.55(m, 1H), 3.78 (m, 1H), 4.02(m, 1H), 4.17(t, 2H), 4.46(dd, 1H), 5.83(bs, 1H), 6.78(s, 1H), 7.15(d, 2H), 7.21(d, 1H), 7.30(m, 3H), 7.53(d, 2H). LRMS: m/z (ES$^+$)391[MH$^+$] |
| 130 | 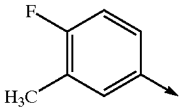 | 62 | $^1$H-NMR($CDCl_3$, 400MHz)δ: 2.20(s, 3H), 3.02 (m, 3H), 3.22(m, 2H), 3.50(m, 1H), 3.75(m, 1H), 4.00(m, 1H), 4.10(m, 2H), 4.42(m, 1H), 5.81(s, 1H), 6.72(m, 2H), 7.02–7.25(m, 7H). LRMS: m/z (ES$^+$)395[MH$^+$] |
| 131 | 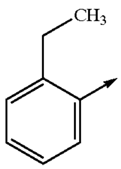 | 52 | $^1$H-NMR($CDCl_3$, 400MHz)δ: □1.04(t, 3H), 2.55 (q, 2H), 3.01(m, 3H), 3.22(m, 2H), 3.48(m, 1H), 3.72(m, 1H), 3.98(m, 1H), 4.10(t, 2H), 4.42(dd, 1H), 6.10(s, 1H), 6.74(s, 1H), 7.06(d, 2H), 7.10 (d, 1H), 7.19(m, 3H), 7.25(m, 3H). Microanalysis found: C, 70.93; H, 7.15; N, 10.39. $C_{24}H_{27}N_3O_2$; $H_2O$ requires C, 70.74; H, 7.17; N, 10.31%. |

Preparation 132

(2RS)-2-({1-[(2EZ)-3-Bromo-2-propenyl]-1H-imidazol-4-yl}methyl)-3-morpholinone

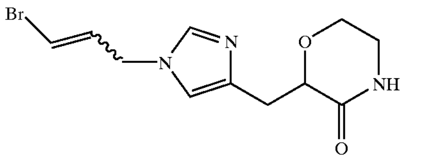

A mixture of ammonium cerium (IV) nitrate (2.6 g, 4.75 mmol) and the compound of Preparation 67 (1 g, 2.38 mmol) in acetonitrile (10 ml) and water (5 ml) was stirred at 40° C. for 18 hours. TLC analysis showed starting material remaining, so additional ammonium cerium (IV) nitrate (650 mg, 1.19 mmol) was added and the mixture was stirred for a further 3 hours at 40° C. The mixture was concentrated under reduced pressure and azeotroped with methanol. The crude product was pre-adsorbed onto silica gel and purified twice by column chromatography on silica gel using an elution gradient of dichloromethane:methanol:0.88 ammonia (99:1:0.1 to 95:5:0.5) to afford the title compound, 370 mg. $^1$H-NMR ($CDCl_3$, 400 MHz) (mixture of geometric isomers) δ: 3.00 (m, 1H), 3.23 (m, 2H), 3.50 (m, 1H), 3.74 (m, 1H), 4.00 (m, 1H), 4.42 (m, 2H), 4.62 (d, 1H), 5.98 (bs, 1H), 6.26 (m, 1.5H), 6.42 (d, 0.5H), 6.75 (2×s, 1H), 7.40 (2×s, 1H). LRMS: m/z ($ES^+$) 300, 302 [$MH^+$]

Preparation 133

(−)-(2S)-2-{[1-(2-Cyclohexylethyl)-1H-imidazol-4-yl]methyl}-3-morpholinone

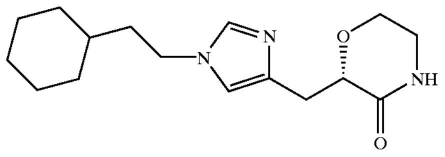

Ammonium cerium (IV) nitrate (482 mg, 0.88 mmol) and water (1 ml) were added to a solution of the compound of Preparation 60 (181 mg, 0.44 mmol) in acetonitrile (1 ml) and the mixture was stirred at 40° C. for 18 hours. TLC analysis showed starting material remaining, so additional ammonium cerium (IV) nitrate was added (250 mg, 0.46 mmol) and the mixture was stirred at 40° C. for a further 5 hours. The mixture was partitioned between dichloromethane (75 ml) and a solution of ethylenediaminetetraacetic acid (1 g) in aqueous sodium bicarbonate (30 ml), and the phases were separated. The organic layer was dried ($MgSO_4$) and evaporated under reduced pressure. The crude product was purified by column chromatography on silica gel using an elution gradient of dichloromethane:methanol:0.88 ammonia (100:0:0 to 94:6:0.6) to afford the title compound as a sticky gum, 80 mg. $^1$H-NMR ($CDCl_3$, 400 MHz) δ: 0.97 (m, 2H), 1.20 (m, 4H), 1.63 (m, 7H), 3.02 (dd, 1H), 3.26 (m, 2H), 3.56 (m, 1H), 3.78 (m, 1H), 3.86 (t, 2H), 4.02 (m, 1H), 4.45 (m, 1H), 5.83 (bs, 1H), 6.76 (s, 1H), 7.38 (s, 1H). LRMS: m/z ($TSP^+$) 292.1 [$MH^+$]. $[\alpha]_D$=−60.01, (c=0.05, methanol)

Preparation 134

(2RS)-2-({1-[(2EZ)-3-[1,1'-Biphenyl]-4-yl-2-propenyl]-1H-imidazol-4-yl}methyl)-3-morpholinone

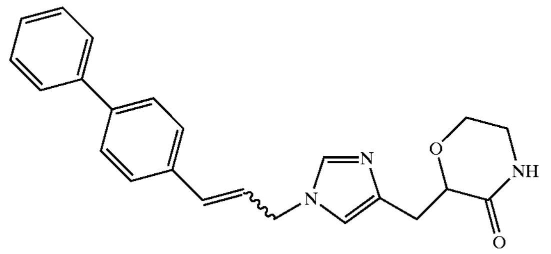

A mixture of the bromo compound of Preparation 132 (185 mg, 0.62 mmol), 4-biphenylboronic acid (183 mg, 0.925 mmol), tetrakis(triphenylphosphine)palladium(0) (72 mg, 0.062 mmol) and sodium carbonate (78 mg, 0.74 mmol) in water (3 ml) and dioxan (6 ml) was heated at 100° C. for 3 hours, then cooled and partitioned between water (20 ml) and ethyl acetate (20 ml). The layers were separated and the aqueous phase was extracted with ethyl acetate (10 ml). The combined organic extracts were dried ($MgSO_4$) and evaporated under reduced pressure. The crude product was purified by column chromatography on silica gel using an elution gradient of dichloromethane:methanol:0.88 ammonia (99:1:0.1 to 98:2:0.2) to afford the title compound as a white foam, 100 mg. $^1$H-NMR ($CDCl_3$, 400 MHz) (mixture of geometric isomers) δ: 3.00 (m, 1H), 3.22 (m, 2H), 3.54 (m, 1H), 3.75 (m, 1H), 4.00 (m, 1H), 4.44 (m, 1H), 4.62 (m, 1H), 4.78 (m, 1H), 5.80, 6.26 (2×m, 1H), 5.93 (bs, 1H), 6.54, 6.66–6.80 (2×m, 2H), 7.23–7.60 (m, 10H). LRMS: m/z ($ES^+$) 374 [$MH^+$]

Preparations 135 to 137

The following compounds of general structure

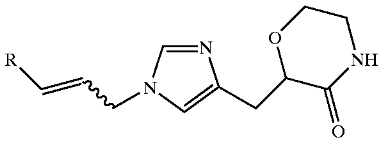

were prepared from the bromide of Preparation 132 and the appropriate boronic acid, following similar procedures to that described in Preparation 134.

| Prep | R | Yield (%) | Data |
|---|---|---|---|
| 135 | 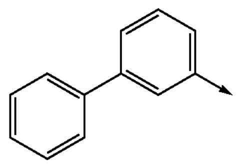 | 36 white foam | $^1$H-NMR($CDCl_3$, 400MHz)(mixture of geometric isomers)δ: 3.00(m, 1H), 3.20–3.35(m, 2H), 3.50(m, 1H), 3.62(m, 1H), 3.98(m, 1H), 4.42(m, 1H), 4.62(m, 1H), 4.78(m, 1H), 5.75(bs, 1H), 5.82, 6.30(2xm, 1H), 6.57, 6.78(2xm, 2H), 7.18–7.58(m, 10H). LRMS; m/z ($ES^+$)374[$MH^+$] |

-continued

| Prep | R | Yield (%) | Data |
|---|---|---|---|
| 136[1] | 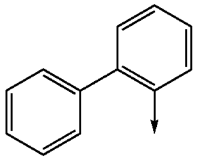 | 41 white foam | $^1$H-NMR($CDCl_3$, 400MHz)(mixture of geometric isomers)δ: 2.98(dd, 1H), 3.22(m, 2H), 3.50(m, 1H), 3.74(m, 1H), 4.00(m, 1H), 4.42(m, 1H), 4.54(m, 2H), 5.66, 6.18(2xm, 1H), 5.82(bs, 1H), 6.50–6.72(m, 2H), 7.22–7.42(m, 10H). LRMS: m/z(ES$^+$)396[MNa$^+$] |
| 137 | 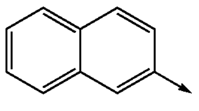 | 51 white foam | $^1$H-NMR($CDCl_3$, 400MHz)(mixture of geometric isomers)δ: 3.00(m, 1H), 3.20–3.35(m, 2H), 3.50(m, 1H), 3.75(m, 1H), 4.00(m, 1H), 4.44(m, 1H), 4.64(m, 1H), 4.80(m, 1H), 5.78(bs, 1H), 5.84, 6.38(2xm, 1H), 6.62–6.85(m, 2H), 7.30–7.82(m, 8H). LRMS: m/z (ES$^+$)348[MH$^+$] |

[1]isolated without column chromatography

Preparation 138

(2RS)-2-({1-[(2EZ)-3-(4-Bromophenyl)-2-propehyl]-1H-imidazol-4-yl}methyl)-3-morpholinone

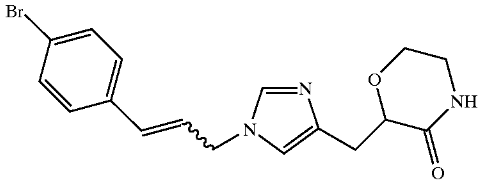

The title compound was obtained in 42% yield from the compound of Preparation 67 and 4-bromobenzeneboronic acid following the procedure described in Preparation 134. $^1$H-NMR ($CDCl_3$, 400 MHz) (mixture of geometric isomers) δ: 3.00 (m, 1H), 3.25 (m, 2H), 3.54 (m, 1H), 3.76 (m, 1H), 4.00 (m, 1H), 4.43 (m, 1H), 4.59–4.79 (m, 2H), 5.80, 6.22 (2×m, 2H), 6.40, 6.62 (2×m, 1H), 6.72, 6.78 (2×s, 1H), 7.06 (d, 1H), 7.19 (d, 1H), 7.38–7.58 (m, 3H). LRMS: m/z (TSP$^+$) 376.1, 378.1 [MH$^+$]

Preparation 139

(2RS)-2-({1-[(2EZ)-3-(4'-Methyl[1,1'-biphenyl]-4-yl)-2-propenyl]-1H-imidazol-4-yl}methyl)-3-morpholinone

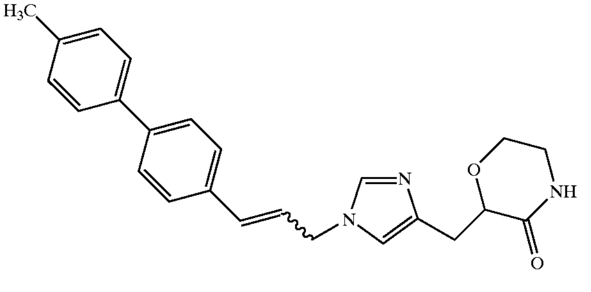

A mixture of the bromo compound of Preparation 138 (132 mg, 0.35 mmol), 4-methylbenzeneboronic acid (72 mg, 0.53 mmol), tetrakis(triphenylphosphine)palladium(0) (50 mg, 0.04 mmol) and sodium carbonate (270 μl, 2M, 0.53 mmol) in dioxan (6 ml) was heated at 100° C. for 1.5 hours. The cooled reaction mixture was partitioned between water (20 ml) and ethyl acetate (20 ml) and the layers were separated. The aqueous phase was extracted with ethyl acetate (10 ml) and the combined organic extracts were dried ($MgSO_4$) and evaporated under reduced pressure. The residual yellow oil was purified by column chromatography on silica gel using an elution gradient of dichloromethane:methanol:0.88 ammonia (99:1:0.1 to 98:2:0.2) to afford the title compound as a white foam, 77 mg. $^1$H-NMR ($CDCl_3$, 400 MHz) (mixture of geometric isomers) δ: 2.38 (2×s, 3H), 3.00 (m, 1H), 3.25 (m, 2H), 3.54 (m, 1H), 3.75 (m, 1H), 4.00 (m, 1H), 4.43 (m, 1H), 4.62 (m, 1H), 4.78 (m, 1H), 5.78, 6.28 (2×m, 2H), 6.55, 6.68–6.80 (2×m, 2H), 7.22 (m, 3H), 7.38–7.63 (m, 6H). LRMS: m/z (ES$^+$) 388 [MH$^+$]

Preparation 140

(2RS)-2-({1-[(2EZ)-3-(4'-Chloro[1,1'-biphenyl]-4-yl)-2-propenyl]-1H-imidazol-4-yl}-methyl)-3-morpholinone

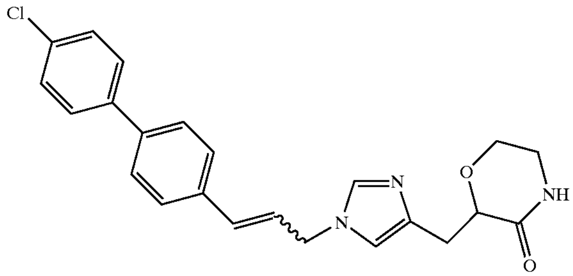

A mixture of the bromo compound of Preparation 138 (100 mg, 0.27 mmol), 4-chlorobenzeneboronic acid (63 mg, 0.4 mmol), tetrakis(triphenylphosphine)palladium(0) (31 mg, 0.027 mmol) and sodium carbonate solution (400 μl, 2M, 0.79 mmol) in ethanol (1 ml) and toluene (4 ml) was heated at 100° C. for 3 hours. TLC analysis showed starting material remaining, so dioxan (3 ml), additional 4-chlorobenzeneboronic acid (21 mg, 0.13 mmol) and tetrakis(triphenylphosphine)palladium(0) (15 mg, 0.013 mmol) were added, and the mixture was stirred at 100° C. for a further 6 hours. The cooled reaction mixture was partitioned between water (10 ml) and ethyl acetate (20 ml) and the layers were separated. The aqueous phase was extracted with ethyl acetate (10 ml) and the combined organic extracts were dried ($MgSO_4$) and evaporated under reduced pressure. The crude product was purified by column chromatography on silica gel using dichloromethane:methanol:0.88 ammonia (98:2:0.2) as eluant to afford the title compound as a white solid, 60 mg. $^{1}$H-NMR ($CDCl_3$, 400 MHz) (mixture of geometric isomers) δ: 3.02 (m, 1H), 3.27 (m, 2H), 3.57 (m, 1H), 3.78 (m, 1H), 4.02 (m 1H), 4.47 (m, 1H), 4.65, 4.79 (2×d, 2H), 5.82, 6.32 (m, 1H), 6.18 (bs, 1H), 6.57, 6.82 (2×m, 2H), 7.30 (d, 1H), 7.39–7.79 (m, 8H). LRMS: m/z ($ES^+$) 430 [$MNa^+$]

Preparation 141

(2RS)-2-({1-[(2EZ)-3-(2',5'-Difluoro[1,1'-biphenyl]-4-yl)-2-propenyl]-1H-imidazol-4-yl}methyl)-3-morpholinone

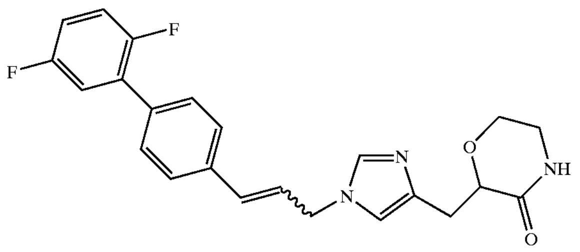

The title compound was obtained from the compound of Preparation 138 and 2,5-difluorobenzeneboronic acid following the procedure described in Preparation 140. $^{1}$H-NMR ($CDCl_3$, 400 MHz) (mixture of geometric isomers) δ: 3.02 (m, 1H), 3.28 (m, 2H), 3.57 (m, 1H), 3.78 (m, 1H), 4.00 (m, 1H), 4.45 (m, 1H), 4.63 (d, 1H), 4.79 (d, 1H), 5.82, 6.36 (m, 1H), 6.14 (bs, 1H), 6.58, 6.79 (2×m, 2H), 7.00 (m, 1H), 7.14 (m, 2H), 7.32 (d, 1H), 7.40–7.70 (m, 4H). LRMS: m/z ($ES^+$) 432 [$MNa^+$]

Preparation 142 tert-Butyl (2RS)-2-[2-(dimethylamino)ethoxy]-3-(1-propyl-1H-imidazol-4-yl)propanoate

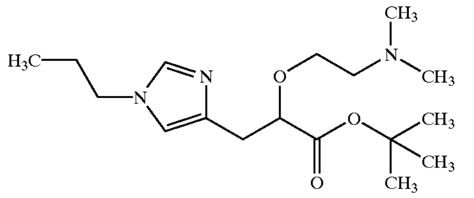

A mixture of the alkene of Preparation 44 (650 mg, 2.01 mmol) and 10% palladium on charcoal (Degussa® 101) (60 mg) in ethanol (20 ml) was hydrogenated at 50° C. and 60 psi (410 kPa) for 18 hours. The cooled mixture was filtered through Arbocel® and the filtrate was evaporated under reduced pressure. The residue was purified by column chromatography on silica gel using an elution gradient of ethyl acetate:diethylamine:methanol (100:0:0 to 97:1.5:1.5) to afford the title compound, 502 mg. $^{1}$H-NMR ($CDCl_3$, 400 MHz) δ: 0.92 (t, 3H), 1.42 (s, 9H), 1.77 (m, 2H), 2.21 (s, 6H), 2.48 (t, 2H), 2.90–3.03 (m, 2H), 3.42 (m, 1H), 3.70 (m, 1H), 3.80 (t, 2H), 4.08 (m, 1H), 6.79 (s, 1H), 7.37 (s, 1H). LRMS: m/z ($TSP^+$) 326.2 [$MH^+$]

Preparation 143 tert-Butyl (3S)-3-{(1RS)-2-tert-butoxy-2-oxo-1-[(1-propyl-1H-imidazol-4-yl)methyl]ethoxy}-1-pyrrolidinecarboxylate

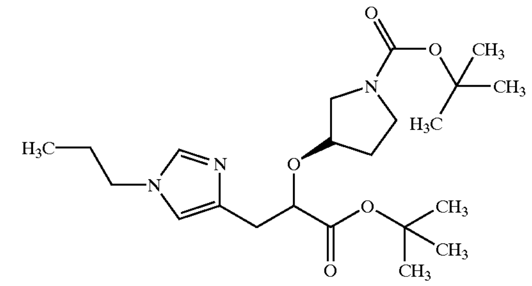

A mixture of the alkene of Preparation 45 (1.19 g, 2.83 mmol) and Degussa® 101 catalyst (120 mg) in ethanol (12 ml) was hydrogenated at 50° C. and 60 psi (410 kPa) for 18 hours. TLC analysis showed starting material remaining, so additional catalyst (120 mg) was added and the mixture was hydrogenated at 50° C. and 60 psi (410 kPa) for a further 48 hours. The mixture was filtered through Arbocel®, the catalyst was washed with ethanol, and the combined filtrates were evaporated under reduced pressure. The residual oil was purified by column chromatography on silica gel using ethyl acetate as the eluant to afford the title compound as a colourless oil, 227 mg. $^{1}$H-NMR ($CDCl_3$, 400 MHz) δ: 00.92 (t, 3H), 1.42 (m, 18H), 1.79 (m, 2H), 2.00–2.30 (m, 2H), 2.80–2.95 (m, 1H), 3.00–3.48 (m, 5H), 3.84 (t, 2H), 4.05–4.20 (m, 2H), 6.75 (m, 1H), 7.50 (m, 1H). LRMS: m/z ($ES^+$) 424 [$MH^+$]

Preparation 144

(2RS)-2-{[1-(3-[1,1'-Biphenyl]-4-ylpropyl)-1H-imidazol-4-yl]methyl}-3-morpholinone

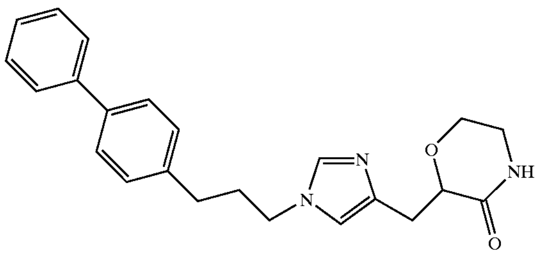

A mixture of the alkene of Preparation 134 (100 mg, 0.268 mmol) and Degussa® 101 catalyst (15 mg) in ethanol (12 ml) was hydrogenated at 50° C. and 60 psi (410 kPa) for 6 hours. TLC analysis showed starting material remaining, so additional Degussa® 101 catalyst (20 mg) was added and the mixture was hydrogenated for a further 18 hours. The reaction mixture was filtered through Arbocel®, the catalyst was washed with ethanol, and the combined filtrates were evaporated under reduced pressure. The residue was purified by column chromatography on silica gel using an elution gradient of dichloromethane:methanol:0.88 ammonia (99:1:0.1 to 98:2:0.2) to afford the title compound as a colourless oil, 70 mg. $^{1}$H-NMR ($CDCl_3$, 400 MHz) δ: 2.10 (m, 2H), 2.61 (t, 2H), 3.02 (dd, 1H), 3.23 (m, 2H), 3.49 (m, 1H), 3.74 (m, 1H), 3.86 (t, 2H), 4.00 (m, 1H), 4.42 (m, 1H), 6.20 (bs, 1H), 7.20 (d, 2H), 7.29 (m, 1H), 7.39 (m, 4H), 7.50 (d, 2H), 7.54 (d, 2H). LRMS: m/z ($ES^+$) 398 [$MNa^+$]

Preparations 145 to 150

The following compounds of general structure

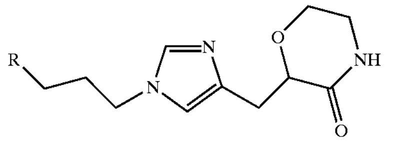

were prepared from the appropriate alkenes, following similar procedures to that described in Preparation 144.

| Prep | R | Yield (%) | Data |
|---|---|---|---|
| 145[1] | 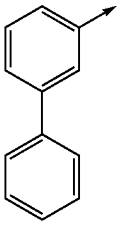 | 70 | $^1$H-NMR(CDCl$_3$, 400MHz)δ: □2.17(m, 2H), 2.68(t, 2H), 3.02(m, 1H), 3.24(m, 2H), 3.50(m, 1H), 3.74(m, 1H), 3.90(t, 2H), 4.00(m, 1H), 4.43(m, 1H), 6.50(bs, 1H), 6.78(s, 1H), 7.16(d, 1H), 7.32–7.48(m, 7H), 7.58(d, 2H). LRMS: m/z (ES$^+$)377[MH$^+$] |
| 146 | 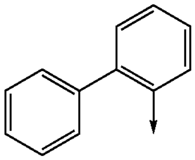 | 71 | $^1$H-NMR(CDCl$_3$, 400MHz)δ: □1.82(m, 2H), 2.58(t, 2H), 2.97(dd, 1H), 3.22(m, 1H), 3.50 (m, 1H), 3.60–3.77(m, 3H), 3.99(m, 1H), 4.40 (m, 1H), 5.82(bs, 1H), 6.55(s, 1H), 7.20(m, 7H), 7.38(m, 3H). LRMS: m/z(ES$^+$)398[MH$^+$] |
| 147 | 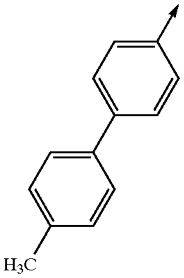 | 65 | $^1$H-NMR(CDCl$_3$, 400MHz)δ: □2.10(m, 2H), 2.38(s, 3H), 2.61(t, 2H), 3.02(dd, 1H), 3.23(m, 2H), 3.50(m, 1H), 3.75(m, 1H), 3.83(t, 2H) 4.00(m, 1H), 4.42(m, 1H), 5.82(bs, 1H), 6.77 (s, 1H), 7.19(m, 4H), 7.38(s, 1H), 7.45(m, 4H). LRMS: m/z(ES$^+$)412[MNa$^+$] |
| 148 | 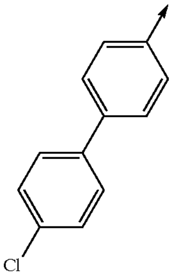 | 57 | $^1$H-NMR(CDCl$_3$, 400MHz)δ: □2.10(m, 2H), 2.60(t, 2H), 3.02(dd, 1H), 3.25(m, 2H), 3.50 (m, 1H), 3.74(m, 1H), 3.85(t, 2H), 4.00(m, 1H), 4.42(m, 1H), 6.05(bs, 1H), 6.77(s, 1H), 7.19(d, 2H), 7.38(m, 3H), 7.45(m, 4H). LRMS: m/z (ES$^+$)432[MNa$^+$] |

-continued

| Prep | R | Yield (%) | Data |
|---|---|---|---|
| 149 | 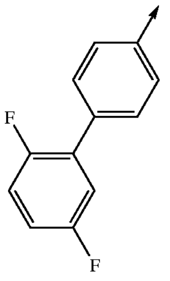 | 76 | $^{1}$H-NMR($CDCl_3$, 400MHz)δ: 2.08(m, 2H), 2.60 (t, 2H), 3.02(dd, 1H), 3.23(m, 2H), 3.50(m, 1H), 3.74(m, 1H), 3.85(t, 2H), 4.00(m, 1H), 4.42(m, 1H), 6.00(bs, 1H), 6.75(s, 1H), 6.96(m, 1H), 7.05(m, 2H), 7.20(d, 2H), 7.38(s, 1H), 7.42(d, 2H). LRMS: m/z($ES^+$)434[$MNa^+$] |
| 150 | 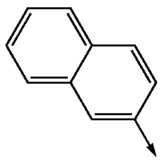 | 70 | $^{1}$H-NMR($CDCl_3$, 400MHz)δ: □□2.20(m, 2H), 2.78(t, 2H), 3.06(dd, 1H), 3.30(m, 2H), 3.54 (m, 1H), 3.75(m, 1H), 3.90(t, 2H), 4.03(m, 1H), 4.48(m, 1H), 5.89(bs, 1H), 6.78(s, 1H), 7.28(d, 1H), 7.39(s, 1H), 7.45(m, 2H), 7.59(s, 1H), 7.80(m, 3H). LRMS: m/z($ES^+$)372[$MNa^+$] |

[1]isolated without column chromatography

Preparation 151

(2S,6R)-4-(4-Methoxybenzyl)-6-methyl-2-{[1-(2-pyridinyl)-1H-imidazol-4-yl]methyl}-3-morpholinone

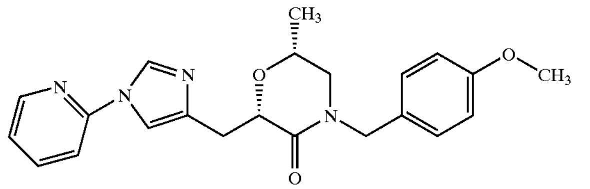

A mixture of the imidazole of Preparation 55 (566 mg, 1.8 mmol), copper (I) oxide (20 mg, 0.14 mmol) and potassium carbonate (372 mg, 2.7 mmol) in 2-bromopyridine (1 ml) was heated at 100° C. for 18 hours. The cooled mixture was purified by Biotage® column chromatography on silica gel using an elution gradient of toluene:diethylamine (93:7 to 86:14) to afford the title compound as a foam, 482 mg. $^{1}$H-NMR ($CDCl_3$, 400 MHz) (5:1 mixture of regioisomers) δ:0.94, 1.20 (2×d, 3H), 2.83–3.23 (m, 4H), 3.63, 3.78 (2×s, 3H), 3.97 (m, 1H), 4.16, 4.22 (2×d, 1H), 4.50–4.82 (m, 2H), 6.64, 6.82 (2×d, 2H), 7.00, 7.18 (2×d, 2H), 7.35, 7.44 (2×m, 1H), 7.59 (m, 2H), 7.96 (m, 1H), 8.40–8.57 (m, 2H). HRMS: m/z ($ES^+$) 393.1926 [$MH^+$]

Preparation 152

(2S,6R)-6-Methyl-2-{[1-(2-pyridinyl)-1H-imidazol-4-yl] methyl}-3-morpholinone

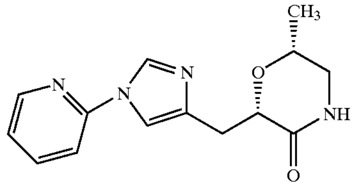

A mixture of the protected morpholinone of Preparation 151 (454 mg, 1.16 mmol) and ammonium cerium (IV) nitrate (1.585 g, 2.9 mmol) in water (8 ml) and acetonitrile (16 ml) was heated at 40° C. for 6 hours. The cooled mixture was diluted with methanol (100 ml), and the solution was adsorbed onto silica gel. The product was isolated by column chromatography on silica gel using dichloromethane:methanol:0.88 ammonia (95:5:1) as eluant and further purified by Biotage® column chromatography on silica gel using toluene:diethylamine (92:8) then dichloromethane:methanol:0.88 ammonia (95:5:1) as eluant to afford the title compound, 204 mg. $^{1}$H-NMR ($CD_3OD$, 400 MHz) (7:1 mixture of regioisomers) δ:1.01, 1.21 (2×d, 3H), 2.92–336 (m, 4H), 3.78, 3.93 (2×m, 1H), 4.27, 4.46 (2×m, 1H), 7.37, 7.45 (2×m, 1H), 7.58–7.70 (m, 2H), 7.96, 8.00 (2×m, 1H), 8.40–8.18 (m, 2H).

Preparation 153

(6R)-2-[Hydroxy(1-propyl-1H-imidazol-4-yl)methyl]-4-(4-methoxybenzyl)-6-methyl-3-morpholinone

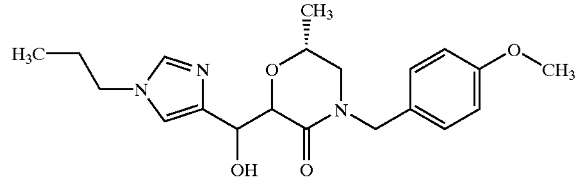

A solution of the compound of Preparation 12 (6.81 g, 29.0 mmol) in tetrahydrofuran was added dropwise to a solution of lithium diisopropylamide (23.2 ml, 1.5M in cyclohexanes, 34.8 mmol) at −78° C., and the solution was stirred for a further 20 minutes at −78° C. A solution of the aldehyde of Preparation 1 (4 g, 29.0 mmol) in tetrahydrofuran (80 ml total volume) was then added dropwise, and the mixture was allowed to warm slowly to room temperature. Saturated ammonium chloride solution (50 ml) was added, followed by water (100 ml), and the mixture was extracted with ethyl acetate. The combined organic extracts were dried ($MgSO_4$) and concentrated under reduced pressure. The residual orange oil was purified by column chromatography on silica gel using an elution gradient of ethyl acetate:methanol (98:2 to 95:5) to afford the title compound as an orange oil, 5.71 g. $^1$H-NMR ($CDCl_3$, 400 MHz) (mixture of diastereoisomers) δ: 0.92 (m, 3H), 1.14 (m, 3H), 1.58 (m, 2H), 2.96–3.18 (m, 2H), 3.78–4.00 (m, 6H), 4.22–4.76 (m, 3H), 5.06–5.30 (m, 1H), 6.81–6.95 (m, 3H), 7.18 (m, 2H), 7.42 (d, 1H). LRMS: m/z ($ES^+$) 374 [$MH^+$]

Preparation 154

(2EZ,6R)-4-(4-Methoxybenzyl)-6-methyl-2-[(1H-imidazol-4-yl)methylidene]-3-morpholinone

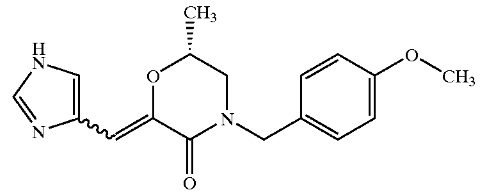

A mixture of the compound of Preparation 37 (91 g, 164 mmol) and water (90 ml) in glacial acetic acid (900 ml) was heated at 40° C. for 1 hour. The cooled mixture was concentrated under reduced pressure, diluted with water (400 ml) and the resulting precipitate filtered off. The filtrate was washed with ether (2×400 ml), then neutralised using sodium bicarbonate and extracted with ethyl acetate (1000 ml). This organic solution washed with water, dried ($Na_2SO_4$) and evaporated under reduced pressure to afford the title compound as a gum, 46.4 g. $^1$H-NMR ($CDCl_3$, 400 MHz) δ: 1.41 (d, 3H), 3.24 (dd, 1H), 3.38 (dd, 1H), 3.80 (s, 3H), 4.34 (m, 1H), 4.58 (d, 1H), 4.68 (d, 1H), 6.84 (d, 2H), 6.97 (s, 1H), 7.20 (d, 2H), 7.30 (s, 1H).

Preparation 155

(2EZ,6R)-4-(4-Methoxybenzyl)-6-methyl-2-[(1-propyl-1H-imidazol-4-yl)methylidene]-3-morpholinone

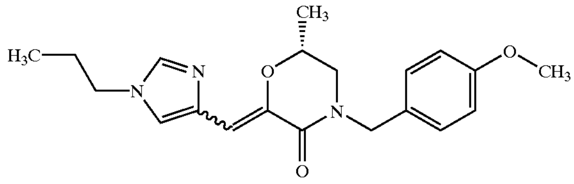

Triethylamine (3 ml, 21.75 mmol) was added dropwise to a solution of the alcohol of Preparation 153 (5.41 g, 14.50 mmol) in dichloromethane (60 ml), and the solution was cooled to 0° C. Methanesulphonyl chloride (1.68 ml, 21.75 mmol) was added, and the mixture was allowed to warm to room temperature, then stirred for a further 2 hours. Additional triethylamine (2 ml, 14.50 mmol) was added, and the mixture was warmed to 35° C., then stirred for 18 hours. The solution was washed with water (100 ml), sodium bicarbonate solution (100 ml) and brine (50ml), then dried ($MgSO_4$) and concentrated under reduced pressure. The residue was purified by column chromatography on silica gel using an elution gradient of dichloromethane:methanol:0.88 ammonia (99:1:0.1 to 98:2:0.2) to afford one isomer of the title compound as an orange oil, 1.8 g, and the second isomer, 260 mg. $^1$H-NMR ($CDCl_3$, 400 MHz, major isomer) δ: 0.96 (t, 3H), 1.38 (d, 3H), 1.80 (m, 2H), 3.20 (dd, 1H), 3.32 (dd, 1H), 3.78 (s, 3H), 3.86 (t, 2H), 4.25 (m, 1H), 4.57 (d, 1H), 4.65 (d, 1H), 6.84 (d, 2H), 7.02 (s, 1H), 7.20 (d, 2H), 7.35 (s, 1H), 7.46 (s, 1H). LRMS: m/z ($ES^+$) 356 [$MH^+$]. Microanalysis found: C, 63.99; H, 6.88; N, 11.00 $C_{20}H_{25}N_3O_3$;$H_2O$ requires C, 64.32; H, 7.29; N, 11.25%.

Preparation 156

(2S,6R)-4-(4-Methoxybenzyl)-6-methyl-2-[(1-propyl-1H-imidazol-4-yl )methyl]-3-morpholinone

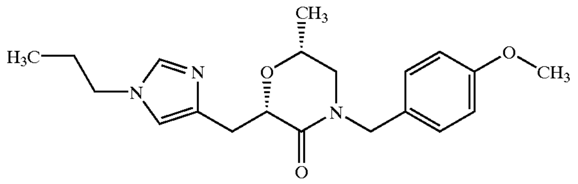

A mixture of the alkene of Preparation 155 (1.8 g, 5.07 mmol) and 10% palladium on charcoal (Degussa type 101) (200 mg) in ethanol (50 ml) was hydrogenated at 60 psi (410 kPa) and 50° C. for 18 hours. TLC analysis showed starting material remaining. The mixture was filtered, the filtrate was evaporated under reduced pressure, and the residue was re-dissolved in ethanol (50 ml). 10% Palladium on charcoal (Degussa type 101) (200 mg) was added and the mixture was hydrogenated at 60 psi (410 kPa) and 50° C. for 18 hours, then filtered. The filtrate was evaporated under reduced pressure and the residue was purified by column chromatography on silica gel using dichloromethane:methanol:0.88 ammonia (98:2:0.2) to afford the title compound as a colourless oil, 1.35 g. $^1$H-NMR ($CDCl_3$, 400 MHz) δ: 0.92 (t, 3H), 1.19 (d, 3H), 1.78 (m, 2H), 2.98–3.16 (m, 3H), 3.58 (dd, 1H), 3.82 (m, 6H), 4.50 (m, 3H), 6.75 (s, 1H), 6.82 (d, 2H), 7.18 (d, 2H), 7.58 (s, 1H). LRMS: m/z ($ES^+$) 358 [$MH^+$]. Microanalysis found: C, 62.12; H, 7.58; N, 10.89 $C_{20}H_{27}N_3O_3$; 1.5$H_2O$ requires C, 62.48; H, 7.86: N, 10.93%.

Preparation 157

(2S,6R)-6-Methyl-2-[(1-propyl-1H-imidazol-4-yl) methyl]-3-morpholinone

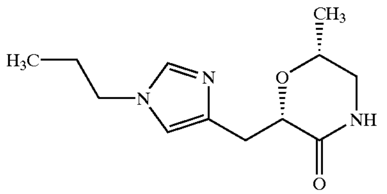

A solution of the compound of Preparation 156 (1.2 g, 3.36 mmol) in methanesulphonic acid (5 ml) was stirred at 70° C. for 2 hours. The cooled mixture was washed with ether (2×20 ml) by decantation. Water (20 ml) was added and the mixture was basified using 0.88 ammonia, then washed with ethyl acetate (20 ml). The aqueous phase was evaporated under reduced pressure, the residue was suspended in acetonitrile, and this mixture was heated to 50° C. The acetonitrile solution was separated by decantation and evaporated under reduced pressure to give an oil. This was purified by column chromatography on silica gel using an elution gradient of dichloromethane:methanol:0.88 ammonia (98:2:0.2 to 96:4:0.4) to afford the title compound as a colourless oil, 560 mg. $^1$H-NMR ($CDCl_3$, 400 MHz) δ: 0.94 (t, 3H), 1.22 (d, 3H), 1.59 (m, 2H), 3.04 (dd, 1H), 3.18–3.37 (m, 3H), 3.85 (m, 3H), 4.42 (m, 1H), 6.50 (s, 1H), 6.79 (s, 1H), 7.68 (s, 1H). LRMS: m/z ($ES^+$) 238 [$MH^+$]

Preparation 158

(2R,6R)-2-[(1H-Imidazol-4-yl)methyl]-6-methyl-3-morpholinone

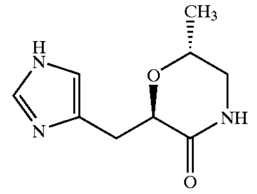

Ammonium cerium (IV) nitrate (1.1 g, 2 mmol) was added to a solution of the protected lactam of Preparation 55b (200 mg, 0.63 mmol) in water (4 ml) and acetonitrile (4 ml) and the mixture was stirred at room temperature for 3 hours. The solution was diluted with acetonitrile (5 ml) and 0.88 ammonia (4 ml), and the mixture was filtered through Arbocel®, washing through with a solution of acetonitrile-:water (50:50, 10 ml). The filtrate was concentrated under reduced pressure and the aqueous residue was washed with ether, then evaporated under reduced pressure. The crude product was purified by column chromatography on silica gel using an elution gradient of dichloromethane:methanol:0.88 ammonia (95:5:0.25 to 92:8:0.4) to afford the title compound as a foam, 88 mg. $^1$H-NMR ($D_2O$, 400 MHz) δ: 1.20 (d, 3H), 3.02–3.30 (m, 6H), 4.01 (m, 1H), 4.40 (dd, 1H), 6.86 (s, 1H), 7.58 (s, 1H).

The compounds of the present invention may be tested using the following assay, which is based on that disclosed in Boffa et al., *J. Biol. Chem.* 1998, 273, 2127. The compounds are incubated with activated TAFI and a standard substrate for TAFIa, the rate of hydrolysis of the substrate is determined and compared to the rate of hydrolysis in the absence of the compounds, and the amount of inhibition expressed in terms of $K_i$.

Assay for TAFIa Inhibition i) TAFI Activation

Human TAFI (recombinant or purified) was activated by incubating 20 μl of stock solution (360 μg/ml) with 10 μl of human thrombin (10NIH units/ml), 10 μl of rabbit thrombomodulin (30 μg/ml), 6 μl calcium chloride (50 mM) in 50 μl of 20 mM HEPES (N-[2-hydroxyethyl]piperazine-N-[2-ethanesulfonic acid]) buffer containing 150 mM sodium chloride and 0.01% TWEEN 80 (polyoxyethylene-sorbitan monooleate) pH 7.6 for 20 minutes at 22° C. At the end of the incubation period, thrombin was neutralised by the addition of 10 μL of PPACK (D-Phe-Pro-Arg chloromethyl ketone) (100 nM). The resulting TAFIa solution was stored on ice for 5 minutes and finally diluted with 175 μl of HEPES buffer.

ii) $K_i$ Determination (TAFIa)

Calculated $K_i$

A number of different dilutions of the test compound in water were made up. To 20 μl of each dilution was added 150 μl of HEPES buffer and 10 μl of TAFIa, which was then pre-incubated for 15 minutes at 24° C. To each dilution was then added 20 μl furylacryloyl-alanyl-lysine (FAAL) at a standard concentration. Substrate turnover was measured by reading the absorbance of the reaction mixture at 330 nm every 15 seconds for 30 minutes. The reaction was performed at 24° C. and samples were mixed for 3 seconds prior to each absorbance reading.

A graph of % inhibition against test compound concentration was then plotted; from which was calculated the $IC_{50}$ value. The $K_i$ value was then calculated using the Cheng-Prusoff equation.

Two controls, positive and negative, were used to check the accuracy of the results in each case. For the first control, the assay was performed as above, but with 20 μl of water rather than a dilution of the test compound. This showed minimal inhibition. For the second control, the assay was performed as above, but with an effective amount of a non specific carboxypeptidase inhibitor rather than a dilution of the test compound. This showed maximal inhibition. When the two controls did not demonstrate minimal and maximal inhibition respectively then the results were discounted and the test compound was reanalysed.

Using the above assay the compounds of the Examples were found to be potent and selective inhibitors of TAFIa. All the compounds tested had a $K_i$ value less than 20 μM. The specific $K_i$ values of certain compounds are detailed below:

| Compound of Example: | $K_i$(TAFla) |
|---|---|
| 4 | 10 nM |
| 5 | 10 nM |
| 40 | 14 nM |
| 49 | 9 nM |
| 51 | 26 nM |

The selectivity of the compounds of the present invention for TAFIa over CPN was determined by calculating the $K_i$ of the compounds of the present invention for CPN, then comparing it to the $K_i$ for TAFIa. The $K_i$ was calculated using the assay for the calculation of TAFIa $K_i$, but substituting 10 μl of human CPN for 10 μl of TAFIa. Those compounds of the present invention tested exhibited a strong selectivity for TAFIa over CPN of the order of >50:1. The specific $K_i$ values and calculated selectivities of certain compounds are detailed below:

| Compound of Example: | $K_i$(CPN) | Selectivity |
|---|---|---|
| 5 | >10 μM | >1000 |
| 51 | >10 μM | >380 |

What is claimed is:

1. A compound according to formula (I)

(I)

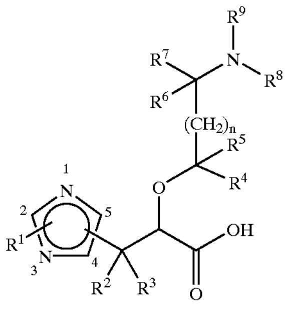

wherein:

n is 0, 1, 2 or 3;

$R^1$ is selected from a. an optionally substituted straight chain or branched chain $C_{1-6}$ alkyl group, b. an optionally substituted straight chain or branched chain $C_{2-6}$ alkenyl group, c. an optionally substituted straight chain or branched chain $C_{2-6}$ alkynyl group, d. Aryl, e. Aromatic heterocycle, f. Heterocycle, and g. hydrogen;

where the optional substituents in groups (a), (b) and (c) above are selected from: $C_{3-7}$ cycloalkyl, Aryl, Aromatic heterocycle, Heterocycle, $OR^{10}$, $NR^{10}R^{11}$, $S(O)_pR^{10}$, $OC(O)R^{11}$, $CO_2R^{10}$, $CONR^{10}R^{11}$, $SO_2NR^{10}R^{11}$, halo and $NHSO_2R^{10}$, and where p is 0, 1 or 2;

$R^2$, $R^3$, $R^4$, $R^6$, $R^7$ and $R^9$ are each independently selected from hydrogen and straight chain or branched chain $C_{1-6}$ alkyl optionally substituted by $OR^{10}$ or halo;

$R^5$ and $R^8$ are each independently selected from hydrogen and straight chain or branched chain $C_{1-6}$ alkyl optionally substituted by $OR^{10}$ or halo, or together are a $C_{2-6}$ alkylene chain;

$R^{10}$ and $R^{11}$ are each independently selected from hydrogen and straight chain or branched chain $C_{1-6}$ alkyl;

Aryl is a 6–14 membered aromatic monocyclic or fused polycyclic carbocyclic group optionally substituted with one or more groups selected from $R^{12}$, halo, $OR^{13}$, $NR^{13}R^{14}$, $NR^{13}CO_2R^{12}$, $CO_2R^{13}$, $NR^{13}SO_2R^{12}$, CN, haloalkyl, O(haloalkyl), $SR^{13}$, $S(O)R^{12}$, $SO_2R^{12}$, $OC(O)R^{13}$, $SO_2NR^{13}R^{14}$, $C(O)NR^{13}R^{14}$, $C_{3-7}$ cycloakyl, O($C_{3-7}$ cycloalkyl), $R^{15}$ and $OR^{15}$, where $R^{12}$ is straight chain or branched chain $C_{1-6}$ alkyl, $R^{13}$ and $R^{14}$ are each independently selected from hydrogen and straight chain or branched chain $C_{1-6}$ alkyl, and $R^{15}$ is phenyl optionally substituted by $R^{12}$, $OR^{13}$, halo or haloalkyl;

Aromatic heterocycle is a 5 to 7 membered aromatic ring containing from 1 to 3 heteroatoms, each independently selected from O, S and N, said ring being optionally substituted with one or more groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{13}$, $NR^{13}R^{14}$, $CO_2R^{13}$, $NR^{13}CO_2R^{14}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$, or a tautomer thereof, or a pharmaceutically acceptable salt of said compound or said tautomer.

2. A compound according to claim 1 wherein the substitution pattern of the imidazole is as depicted in formula ($ID^1$).

($ID^1$)

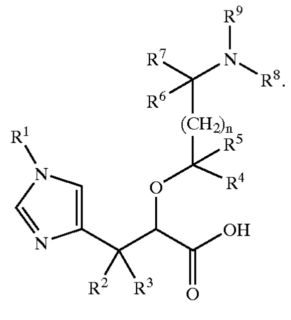

3. A compound according to claim 1 wherein the stereochemistry is as depicted in formula (IA)

(IA)

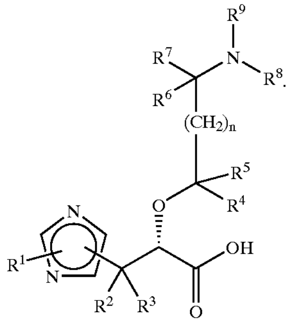

4. A compound according to any preceding claim wherein n is 0 or 1.

5. A compound according to claim 4 wherein n is 0.

6. A compound according to claim 1 wherein $R^1$ is hydrogen, Aryl, $C_{2-6}$ alkenyl or a $C_{1-6}$ alkyl group optionally substituted by one or more groups selected from $C_{3-7}$ cycloalkyl, Aryl, Aromatic heterocycle, $OR^{10}$, $CO_2R^{10}$, halo and $NHSO_2R^{10}$.

7. A compound according to claim 6 wherein $R^1$ is hydrogen, Aryl or a $C_{1-6}$ alkyl group optionally substituted by a group selected from cyclohexyl and Aryl.

8. A compound according to claim 7 wherein $R^1$ is hydrogen or $C_{1-3}$ alkyl.

9. A compound according to claim 8 wherein $R^1$ is hydrogen.

10. A compound according to claim 1 wherein $R^2$ and $R^3$ are each independently hydrogen or $C_{1-6}$ alkyl.

11. A compound according to claim 10 wherein $R^2$ and $R^3$ are both hydrogen.

12. A compound according to claim 1, wherein $R^4$ is hydrogen or $C_{1-6}$ alkyl.

13. A compound according to claim 12 wherein $R^4$ is hydrogen.

14. A compound according to claim 1, wherein $R^6$, $R^7$ and $R^9$ are each independently hydrogen or $C_{1-3}$ alkyl.

15. A compound according to claim 14 wherein $R^6$, $R^7$ and $R^9$ are each independently hydrogen or methyl.

16. A compound according to claim 15 wherein $R^6$, $R^7$ and $R^9$ are all hydrogen.

17. A compound according to claim 1 wherein $R^5$ is hydrogen or $C_{1-3}$ alkyl.

18. A compound according to claim 17 wherein $R^5$ is hydrogen or methyl.

19. A compound according to claim 18 wherein $R^5$ is methyl.

20. A compound according to any one of claims 17, 18 and 19 wherein $R^8$ is hydrogen or methyl.

21. A compound according to claim 20 wherein $R^8$ is hydrogen.

22. A compound according to claim 1, selected from:

(2S)-(−)-2-(2-aminoethoxy)-3-(1-phenyl-1H-imidazol-4-yl)propanoic acid;

(2S)-2-{[(1R)-2-amino-1-methylethyl]oxy}-3-[1-(2-cyclohexylethyl)-1H-imidazol-4-yl]-propanoic acid;

(2S)-2-{[(1R)-2-amino-1-methylethyl]oxy}-3-(1-phenyl-1H-imidazol-4-yl)propanoic acid;

(2S)-2-{[(2S)-2-aminopropyl]oxy}-3-[1-(2-cyclohexylethyl)-1H-imidazol-4-yl]propanoic acid;

(2S)-2-(2-aminoethoxy)-3-(1H-imidazol-4-yl)propanoic acid;

(2S)-2-{[(1R)-2-amino-1-methylethyl]oxy}-3-(1H-imidazol-4-yl)propanoic acid; and (2S)-2-{[(1R)-2-amino-1-methylethyl]oxy}-3-[1-(2-pyridinyl)-1H-imidazol-4-yl]propanoic acid, and pharmaceutically acceptable salts thereof.

23. A pharmaceutical composition comprising a compound according to any one of claim 1, 2 or 3 and a pharmaceutically acceptable carrier.

24. A method of treatment of a condition selected from thrombotic conditions, atherosclerosis, adhesions, dermal scarring, cancer, fibrotic conditions, inflammatory diseases and those conditions which benefit from maintaining or enhancing bradykinin levels in the body, comprising administration of a compound according to any of claim 1, 2 or 3 to subject in need of such treatment.

25. A process for the preparation of a compound according to formula (I)

(I)

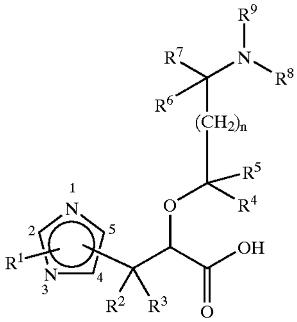

wherein:

n is 0, 1, 2 or 3;

$R^1$ is selected from a. an optionally substituted straight chain or branched chain $C_{1-6}$ alkyl group, b. an optionally substituted straight chain or branched chain $C_{2-6}$ alkenyl group, c. an optionally substituted straight chain or branched chain $C_{2-6}$ alkynyl group, d. Aryl, e. Aromatic heterocycle, f. Heterocycle, and g. hydrogen;

where the optional substituents in groups (a), (b) and (c) above are selected from: $C_{3-7}$ cycloalkyl, Aryl, Aromatic heterocycle, Heterocycle, $OR^{10}$, $NR^{10}R^{11}$, $S(O)_pR^{10}$, $OC(O)R^{11}$, $CO_2R^{10}$, $CONR^{10}R^{11}$, $SO_2NR^{10}R^{11}$, halo and $NHSO_2R^{10}$, and where p is 0, 1 or 2;

$R^2$, $R^3$, $R^4$, $R^6$, $R^7$ and $R^9$ are each independently selected from hydrogen and straight chain or branched chain $C_{1-6}$ alkyl optionally substituted by $OR^{10}$ or halo;

$R^5$ and $R^8$ are each independently selected from hydrogen and straight chain or branched chain $C_{1-6}$ alkyl optionally substituted by $OR^{10}$ or halo, or together are a $C_{2-6}$ alkylene chain;

$R^{10}$ and $R^{11}$ are each independently selected from hydrogen and straight chain or branched chain $C_{1-6}$ alkyl;

Aryl is a 6–14 membered aromatic monocyclic or fused polycyclic carbocyclic group optionally substituted with one or more groups selected from $R^{12}$, halo, $OR^{13}$, $NR^{13}R^{14}$, $NR^{13}CO_2R^{12}$, $CO_2R^{13}$, $NR^{13}SO_2R^{12}$, CN, haloalkyl, O(haloalkyl), $SR^{13}$, $S(O)R^{12}$, $SO_2R^{12}$, $OC(O)R^{13}$, $SO_2NR^{13}R^{14}$, $C(O)NR^{13}R^{14}$, $C_{3-7}$ cycloakyl, O($C_{3-7}$ cycloalkyl), $R^{15}$ and $OR^{15}$, where $R^{12}$ is straight chain or branched chain $C_{1-6}$ alkyl, $R^{13}$ and $R^{14}$ are each independently selected from hydrogen and straight chain or branched chain $C_{1-6}$ alkyl, and $R^{15}$ is phenyl optionally substituted by $R^{12}$, $OR^{13}$, halo or haloalkyl;

Aromatic heterocycle is a 5 to 7 membered aromatic ring containing from 1 to 3 heteroatoms, each independently selected from O, S and N, said ring being optionally substituted with one or more groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{13}$, $NR^{13}R^{14}$, $CO_2R^{13}$, $NR^{13}CO_2R^{14}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$, or a tautomer thereof, comprising the steps of:

(i) preparing a compound according to formula (II)

(II)

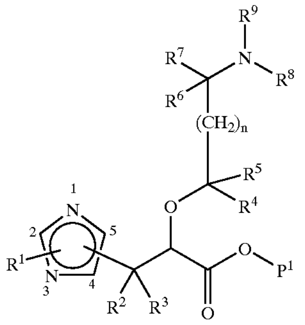

wherein:

$P^1$ is an optionally substituted $C_{1-6}$ alkyl group, an optionally substituted $C_{4-7}$ cycloalkyl group, an optionally substituted benzyl group or a tri($C_{1-6}$ alkyl)silyl group; and $R^1$, $R^2$, $R^3$, $R^4$, $R^5$, $R^6$, $R^7$, $R^8$, $R^9$ and n are as defined for formula (I); and (ii) treating said compound of formula (II) with a reagent or combination of reagents suitable for removing the $P^1$ group.

26. A process for the preparation of a compound according to formula (I)

(I)

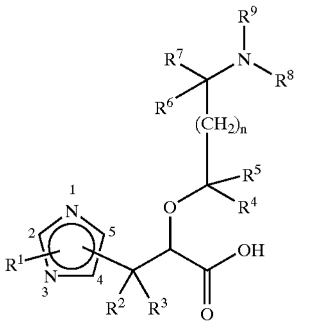

wherein:

n is 0, 1, 2 or 3;

$R^1$ is selected from a. an optionally substituted straight chain or branched chain $C_{1-6}$ alkyl group, b. an optionally substituted straight chain or branched chain $C_{2-6}$ alkenyl group, c. an optionally substituted straight chain or branched chain $C_{2-6}$ alkynyl group, d. Aryl, e. Aromatic heterocycle, f. Heterocycle, and g. hydrogen;

where the optional substituents in groups (a), (b) and (c) above are selected from: $C_{3-7}$ cycloalkyl, Aryl, Aromatic heterocycle, Heterocycle, $OR^{10}$, $NR^{10}R^{11}$, $S(O)_pR^{10}$, $OC(O)R^{11}$, $CO_2R^{10}$, $CONR^{10}R^{11}$, $SO_2NR^{10}R^{11}$, halo and $NHSO_2R^{10}$, and where p is 0, 1 or 2;

$R^2$, $R^3$, $R^4$, $R^6$ and $R^7$ are each independently selected from hydrogen and straight chain or branched chain $C_{1-6}$ alkyl optionally substituted by $OR^{10}$ or halo;

$R^5$ and $R^8$ are each independently selected from hydrogen and straight chain or branched chain $C_{1-6}$ alkyl optionally substituted by $OR^{10}$ or halo, or together are a $C_{2-6}$ alkylene chain;

$R^9$ is hydrogen;

$R^{10}$ and $R^{11}$ are each independently selected from hydrogen and straight chain or branched chain $C_{1-6}$ alkyl;

Aryl is a 6–14 membered aromatic monocyclic or fused polycyclic carbocyclic group optionally substituted with one or more groups selected from $R^{12}$, halo, $OR^{13}$, $NR^{13}R^{14}$, $NR^{13}CO_2R^{12}$, $CO_2R^{13}$, $NR^{13}SO_2R^{12}$, CN, haloalkyl, O(haloalkyl), $SR^{13}$, $S(O)R^{12}$, $SO_2R^{12}$, $OC(O)R^{13}$, $SO_2NR^{13}R^{14}$, $C(O)NR^{13}R^{14}$, $C_{3-7}$ cycloakyl, O($C_{3-7}$ cycloalkyl), $R^{15}$ and $OR^{15}$, where $R^{12}$ is straight chain or branched chain $C_{1-6}$ alkyl, $R^{13}$ and $R^{14}$ are each independently selected from hydrogen and straight chain or branched chain $C_{1-6}$ alkyl, and $R^{15}$ is phenyl optionally substituted by $R^{12}$, $OR^{13}$, halo or haloalkyl;

Aromatic heterocycle is a 5 to 7 membered aromatic ring containing from 1 to 3 heteroatoms, each independently selected from O, S and N, said ring being optionally substituted with one or more groups selected from $OR^{13}$, $NR^{13}R^{14}$, $CO_2R^{13}$, $NR^{13}CO_2R^{12}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$; and Heterocycle is a 3 to 8 membered ring containing from 1 to 3 heteroatoms, each independently selected from O, S and N, said ring being saturated or partially saturated, said ring further being optionally substituted with one or more groups selected from $OR^{13}$, $NR^{13}R^{14}$, $CO_2R^{13}$, $NR^{13}CO_2R^{14}$, $R^{12}$, halo, CN, haloalkyl, O(haloalkyl), $SR^{13}$, $S(O)R^{12}$, $SO_2R^{12}$, $OC(O)R^{13}$, $NR^{13}SO_2R^{12}$, $SO_2NR^{13}R^{14}$ and $C(O)NR^{13}R^{14}$, or a tautomer thereof, comprising the steps of:

(i) preparing a compound according to formula (XIV)

(XIV)

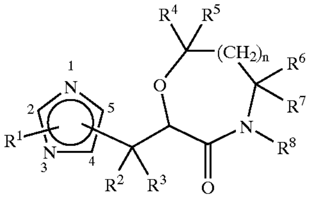

wherein:

$R^1$, $R^2$, $R^3$, $R^4$, $R^5$, $R^6$, $R^7$, $R^8$ and n are as defined for formula (I); and (ii) treating said compound of formula (II) with a reagent or combination of reagents suitable for hydrolyzing the amide bond of the lactam ring.

* * * * *